US009765374B2

(12) United States Patent
Hua et al.

(10) Patent No.: US 9,765,374 B2
(45) Date of Patent: *Sep. 19, 2017

(54) METHOD OF USING α-AMYLASE FROM *ASPERGILLUS FUMIGATUS* AND ISOAMYLASE FOR SACCHARIFICATION

(71) Applicant: Danisco US Inc., Palo Alto, CA (US)

(72) Inventors: Ling Hua, Hockessin, DE (US); Martijn Scheffers, Leiden (NL); Marco Van Brussel, Zoetermeer (NL); Casper Vroemen, Palo Alto, CA (US); Bo Zhang, Shanghai (CN); Zhengong Zhang, Shanghai (CN)

(73) Assignee: DANISCO US INC CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/649,173

(22) PCT Filed: Dec. 5, 2013

(86) PCT No.: PCT/US2013/073317

§ 371 (c)(1),
(2) Date: Jun. 2, 2015

(87) PCT Pub. No.: WO2014/093125

PCT Pub. Date: Jun. 19, 2014

(65) Prior Publication Data

US 2016/0032338 A1 Feb. 4, 2016

(30) Foreign Application Priority Data

Dec. 14, 2012 (WO) ................ PCT/CN2012/086654

(51) Int. Cl.

| | |
|---|---|
| ***C12P 7/06*** | (2006.01) |
| ***C12P 19/14*** | (2006.01) |
| ***A21D 8/04*** | (2006.01) |
| ***C11D 3/386*** | (2006.01) |
| ***D06L 1/06*** | (2006.01) |
| ***C12C 5/00*** | (2006.01) |
| ***C12N 9/30*** | (2006.01) |
| ***C12N 9/44*** | (2006.01) |
| ***C12C 11/00*** | (2006.01) |
| ***C12P 19/02*** | (2006.01) |
| ***A23L 7/104*** | (2016.01) |

(52) U.S. Cl.

CPC .............. *C12P 19/14* (2013.01); *A21D 8/042* (2013.01); *A23L 7/107* (2016.08); *C11D 3/386* (2013.01); *C12C 5/004* (2013.01); *C12C 11/003* (2013.01); *C12N 9/242* (2013.01); *C12N 9/246* (2013.01); *C12P 7/06* (2013.01); *C12P 19/02* (2013.01); *D06L 1/06* (2013.01); *A23V 2002/00* (2013.01); *C12Y 302/01001* (2013.01); *C12Y 302/01068* (2013.01); *Y02E 50/17* (2013.01)

(58) Field of Classification Search

CPC ............... C12P 19/14; C12P 7/06; C12C 7/04

See application file for complete search history.

(56) References Cited

U.S. PATENT DOCUMENTS

| | | | | |
|---|---|---|---|---|
| 5,352,602 | A | 10/1994 | Yamada et al. | |
| 5,422,267 | A | 6/1995 | Yocum et al. | |
| 8,058,033 | B2 | 11/2011 | Aehle et al. | |
| 9,365,871 | B2 * | 6/2016 | Ge | C12C 7/04 |
| 2003/0082595 | A1 * | 5/2003 | Jiang | C12N 9/0006 435/6.13 |

FOREIGN PATENT DOCUMENTS

| | | |
|---|---|---|
| GB | 1230406 | 5/1971 |
| WO | WO03/012071 | 2/2003 |
| WO | WO2005/121305 | 12/2005 |
| WO | WO2008/112459 | 9/2008 |
| WO | WO2009/099783 | 8/2009 |
| WO | WO2011/153516 | 12/2011 |
| WO | WO2013/169645 | 11/2013 |

OTHER PUBLICATIONS

Domingues, C. M., et al., "Production of amylase by soil fungi and partial biochemical characterization of amylase of a selected strain." *Can. J. Microbiol.* 39(7): 681-685, 1993.

Goto, C. E., et al., "Production of Amylase by *Aspergillus fumigatus* Utilizing α-methyl-d-glycoside, a synthetic analogue of maltose, as substrate." *FEMS Microbiology Letters* 167(2): 139-143, 1998.

Planchot, V., et al., "Extensive degradation of native starch granules by *Alpha*-amylase from *Aspergillus fumigatus.*" *J. Cereal Science* 21(2): 163-171, 1995.

Planchot, V., et al., "Purification and characterization of extracellular alpha-amylase from *Aspergillus fumigatus.*" *Carbohydrate Research* 272(1): 97-109, 1995.

Sorimachi, K., et al. "Solution structure of the granular starch binding domain of *Aspergillus niger* glucoamylase bound to beta-cyclodextrin." *Structure* 5(5): 647-61, 1997.

Vujicić-Zagar, A., et al., "Monoclinic crystal form of *Aspergillus niger* α-amylase in complex with maltose at 1.8 Å resolution," *Acta Crystallogr. Sect. F: Struct. Biol. Cryst. Commun.* 62(8): 716-21, 2006.

(Continued)

*Primary Examiner* — Maryam Monshipouri

(57) ABSTRACT

A fungal alpha-amylase is provided from *Aspergillus fumigatus* (AfAmyl). AfAmyl has an optimal pH of 3.5 and is operable at 30-75 degrees C., allowing the enzyme to be used in combination with a glucoamylase and an isoamylase in a saccharification reaction. This obviates the necessity of running a saccharification reaction as a batch process, where the pH and temperature must be readjusted for optimal use of the alpha-amylase or glucoamylase. AfAmyl also catalyzes the saccharification of starch substrates to an oligosaccharide composition significantly enriched in DP2 and (DPI+DP2) compared to the products of saccharification catalyzed by an alpha-amylase from *Aspergillus kawachii*. This facilitates the utilization of the oligosaccharide composition by a fermenting organism in a simultaneous saccharification and fermentation process, for example.

19 Claims, 7 Drawing Sheets

(56) References Cited

OTHER PUBLICATIONS

International Search Report and the Written Opinion of the International Searching Authority for International Application No. PCT/US2013/073317 dated Mar. 13, 2014.

International Preliminary Report on Patentability for International Application No. PCT/US2013/073317 dated Jun. 15, 2015.

NCBI Reference Sequence XP_749208.1; alpha-amylase [Aspergillus fumigatus Af293]; Nierman, W.C., et al., "Genomic sequence of the pathogenic and allergenic filamentous fungus Aspergillus fumigatus." *Nature* 438: 1151-1156, 2005.

UniProt Accession No. A1CYB1_NEOFI, NRRL 181 (XP_001265628.1); Federova, N.D., et al., "Genomic islands in the pathogenic filamentous fungus Aspergillus fumigatus." *PloS Genet.* 4: E1000046, 2008.

NCBI Reference Sequence XP_001209405.1; alpha-amylase precursor [Aspergillus terreus NIH2624], Birren, B., et al., "Annotation of the Aspergillus terreus NIH2624 genome." Unpublished, 2008.

GenBank Accession No. ABF72529.1; alpha amylase AMYI [Ophiostoma floccosum]; Wu, C., et al., Improvement of the secretion of extracellular proteins and isolation and characterization of the amylase I (amyl) gene from Ophiostoma floccosum, *Gene* 384, 96-103, 2006.

NCBI Reference Sequence XP_002560482.1, Pc16g00630 [Penicillium rubens Wisconsin 54/1255]; van den Berg., M.A., et al., "Genome sequencing and analysis of the filamentous fungus Penicillium chrysogenum." *Nat. Biotechnol.* 26(10): 1161-1168, 2008.

UniProt Accession No. 013296_ASPKA, *Aspergillus kawachii* (white koji mold) (*Aspergillus awamore* var *kawachi*); Kaneko, A., et al., "Molecular-cloning and determination of the nucleotide-sequence of a gene encoding an acid-stable alpha-amylase from *Aspergillus kawachii*," *J. Ferment. Bioeng.* 81: 292-298, 1996.

GenBank Accession No. BAD06003.1; alpha-amylase [Aspergillus awamori]; Matsubara, T., et al., "Molecular cloning and determination of the nucleotide sequence of raw starch digesting alpha-amylase from Aspergillus awamori KT-11." *J. Biochem Mol. Biol.* 37(4): 429-438, 2004.

* cited by examiner

FIG. 1A

```
AfAmy1                     24 LTPAEWRSQSIYFLLTDRFGREDNSTTAACDVTQRLY  60
N. fischeri α-amylase      24 LTPAEWRSQSIYFLLTDRFGREDNSTTAACDVTQRLY  60
A. terreus α-amylase       21 LTPAEWRSQSIYFLLTDRFGRTDNSTTAACDTSDRVY  57
O. floccosum α-amylase     19 LSPAEWRKQSIYFLLTDRFGRTDNSTSATCNTGDRAY  55
P. chrysogenum α-amylase   19 LTPAEWRSQSIYFLLTDRFGRTDNSVTANCNVDDRAY  55
A. clavatus α-amylase      20 LTPAEWRSQSIYFLLTDRFGRDDRSTSAPCDTNQRMY  56
A. kawachii α-amylase      22 LSAAEWRTQSIYFLLTDRFGRTDNSTTATCNTGDQIY  58
A. awamori α-amylase       22 LSAAEWRSQSIYFLLTDRFGRTDNSTTATCDTGDQIY  58
                              *  **** ************* * *  * *      *

  61  CGGSWQGIINHLDYIQGMGFTAIWITPVTEQFYENTGDGTSYHGYWQQNIHEVNANYGTA  120
  61  CGGSWQGIINHLDYIQGMGFTAIWITPVTQQFYENTGDGTSYHGYWQQNIYEVNSNYGTA  120
  58  CGGSWQGIINQLDYIQGMGFTAIWITPVTGQFYENTGDGTSYHGYWQQDIYDLNYNYGTA  117
  56  CGGSWQGVINHLDYIQGMGFTAIWITPVTGQFYESTGDGTSYHGYWQQDIYSLNSHLGDQ  115
  56  CGGTWQGIINQLDYIQGMGFTAIWITPVTKQLPQDTGYGMAYHGYWQQDIYDVNDHHGTS  115
  57  CGGTWQGIINQLDYIQGMGFTAIWITPVTEQFYESTGDGSSYHGYWQQNINEVNRKHGTK  116
  59  CGGSWQGIINHLDYIQGMGFTAIWISPITEQLPQDTSDGEAYHGYWQQKIYYVNSNFGTA  118
  59  CGGSWQGIINHLDYIQGMGFTAIWISPITEQLPQDTSDGEAYHGYWQQKIYDVNSNFGTA  118
      *** *** ** ************** * * *    *  *  ******* *   *   *

 121  QDLRDLANALHARGMYLMVDVVANHMGYNGAGNSVNYGVFTPFDSATYFHPYCLITDYNN  180
 121  QDLRKLADALHARGMYLMVDVVANHMGYDGAGNSVDYSVFTPFDSSTYFHTYCLISDYNN  180
 118  QDLKNLANALHERGMYLMVDVVANHMGYDGAGNTVDYSVFNPFSSSSYFHPYCLISNYDN  177
 116  NDLKALSAALHARGMYLMVDVVANHMGYDGAGSNVDYSVFDAFPSSSYFHSYCEISNYDD  175
 116  DDLLALSKALHARGMYLMVDVVANHMGYAGAGNTVDYSVFTPFSSSSYFHPYCLISNYND  175
 117  QDLKNLADALHARGMYLMVDVVANHMGYRGSGQNVDFNTFHPFNRAEHYNSFCTITDYNN  176
 119  DDLKSLSDALHARGMYLMVDVVPNHMGYAGNGNDVDYSVFDPFDSSSYFHPYCLITDWDN  178
 119  DDLKSLSDALHARGMYLMVDVVPNHMGYAGNGNDVDYSVFDPFDSSSYFHPYCLITDWDN  178
       **  *  *** ********** ***** * *  *    *  *         * *

 181  QTAVEDCWLGDTTVSLPDLDTTSTAVRSIWYDWVKGLVANYSIDGLRIDTVKHVEKDFWP  240
 181  QNNVEDCWLGDTTVSLPDLDTTNTAVRTIWYDWVKGLVANYSIDGLRIDTVKHVEKDFWP  240
 178  QTNVEDCWLGDTTVSLPDLDTTSTAVRNIWYDWVADLVANYSIDGLRVDTVKHVEKDFWP  237
 176  QSNVEDCWLGDTTVSLPDLNTELTSVRSIWNSWVAGLVANYSIDGLRIDTVKHVETSFWP  235
 176  QSNVENCWLGDTTVSLPDLDTTQNSVQTIWNDWIADLVTKYSIDGLRIDTVKHVQKSFWP  235
 177  QNSVEKCWLGSNTVSLPDLATTHPWVRSTWYDWVRDLVKDYSIDGLRIDTVKHVEKDFWR  236
 179  LTMVQDCWEGDTIVSLPDLNTTETAVRTIWYDWVADLVSNYSVDGLRIDSVEEVEPDFFP  238
 179  LTMVQDCWEGDTIVSLPDLNTTETAVRTIWYDWVADLVSNYSVDGLRIDSVLEVEPDFFP  238
         *  ** *   ****** *    *   *  *   **  ** **** * *  *   *
```

FIG. 1B

```
241  GYNDAAGVYCVGEVFSGDPQYTCPYQNYLDGVLNYPIYYQLLYAFQSTSGSISNLYNMIS  300
241  DYNDAAGVYCVGEVFSGDPSYTCPYQNYMDGVLNYPIYYQLLYAFQSTSGSISNLYNMIS  300
238  GYNSAAGVYCVGEVYSGDPAYTCPYQNYMDGVLNYPIYYQLLYAFESSSGSISDLYNMIS  297
236  GYNDAAGVYCVGEVFDGDPAYTCAYQNYMDGVLNYPIYYQLLSAFESTSGSISNLYNMIK  295
236  GFNDAAGVYAVGEIFDGNPAYTCDYQNYMDGVLNYPIYYPLLRAFQSSSGSISDLYNMVG  295
237  PYNDAAGVYCVGEIFSGDPGYTCDYQNHMDGVLNYPIYYPLLNAFKSTSGSMGDLRNMIG  296
239  GYQEAAGVYCVGEVDNGNPALDCPYQKYLDGVLNYPIYWQLLYAFESSSGSISNLYNMIK  298
239  GYQEAAGVYCVGEVDNGNPALDCPYQDYLDGVLNYPIYWQLLYAFESSSGSISDLYNMIK  298
         ***** ***   * *   * **   *********  ** ** * ***   * **

301  SVASDCADPTLLGNFIENHDNPRFASYTSDYSQAKNVISFMFFSDGIPIVYAGQEQHYSG  360
301  SVDSDCADPTLLGNFIENHDNPRFASYTSDYSQAKNVISFMFFSDGIPIVYAGQEQHYSG  360
298  SVASSCKDPTLLGNFIENHDNPRFASYTSDYSQAKNVITFIFLSDGIPIVYAGQEQHYSG  357
296  SVASDCADPTLLGNFIENHDNPRFASYTSDYSLAQNAISFLFFSDGIPIVYSGQEQHYSG  355
296  TVASSCADSTLLGNFIENHDNPRFPSYTSDYSQAKNVISFLFLSDGIPIVYAGQEQHYSG  355
297  TVSNKCRDPTLLGNFIENHDNPRFAHYTNDISQAKNVLTFMFLTDGIPIVYAGQEQHYDG  356
299  SVASDCSDPTLLGNFIENHDNPRFASYTSDYSQAKNVLSYIFLSDGIPIVYAGEEQHYSG  358
299  SVASDCSDPTLLGNFIENHDNPRFASYTSDYSQAKNVLSYIFLSDGIPIVYAGEEQHYSG  358
      *   * * ***************  ** * * * *     *  ******* * **** *

361  GADPANREAVWLSGYSTSATLYSWIASTNKIRKLAISKDSAYITSKNNPFYYDSNTLAMR  420
361  GADPANREAVWLSGYSTSATLYSWIASTNKIRKLAISKDSAYITSKNNPFYYDSNTLAMR  420
358  GSDPANREATWLSGYSTSATLYTWIATTNQIRSLAISKDAGYVQAKNNPFYSDSNTIAMR  417
356  GADPANREATWLSGYSTTATLYKHIKTTNQIRSLIIGKDSSWATSANSPFYQDSNTIAML  415
356  GHDPANREAVWLSGYSTTAELYQHIATTNKIRKAAVAADSSYITSKNVPFYQDSHTLAMK  415
357  GEDPHNREATWFSGYNKNAELYTWIAKTNKIRSLAVSKDSGYVTARNNPFYHDTTTLAMR  416
359  GDVPYNREATWLSGYDTSAELYTWIATTNAIRKLAISADSDYITYKNDPIYTDSNTIAMR  418
359  GDVPYNREATWLSGYDTSAELYTWIATTNAIRKLAISADSDYITYANDPIYTDSNTIAMR  418
     *  * **** * ***   * **  *  ** **      *       * * * *  * **

421  KGSVAGSQVITVLSNKGSSGSSYTLSLSGTGYSAGATLVEMYTCTTLTVDSSGNLAVPMV  480
421  KGSVAGSQVITVLSNKGSSGSSYTLSLSGTGYSAGATLVEMYTCTTLTVDSSGNLAVPMA  480
418  KGTTAGAQVITVLSNKGASGSSYTLSLSGTGYSAGATLVETYTCTTVTVDSSGNLPVPMT  477
416  KGSASGSKVLTVLSNKGASGSSYTLSLGSTGYSSGASLVELYSCTTVTVDSSGNVPVPMA  475
415  KGSGS-SPVITVLSNAGSSGSSYTLYLGGSGYSSGTKLMEMHTCTSITVDSSGKIAVPMV  474
417  KGSRDGAQVITIVSNKGASGDGYTMQLSGHGYGSGATVMEMYTCTPLTVGGNGIIPVPMV  476
419  KG-TSGSQIITVLSNKGSSGSSYTLTLSGSGYTSGTKLIEAYTCTSVTVDSNGDIPVPMA  477
419  KG-TSGSQVITVLSNKGSSGSSYTLTLSGSGYTSGTELIEAYTCTSVTVDSNGDIPVPMA  477
     **        *  ** * **  **  *   **  *    *   **  **   *   ***
```

FIG. 1C

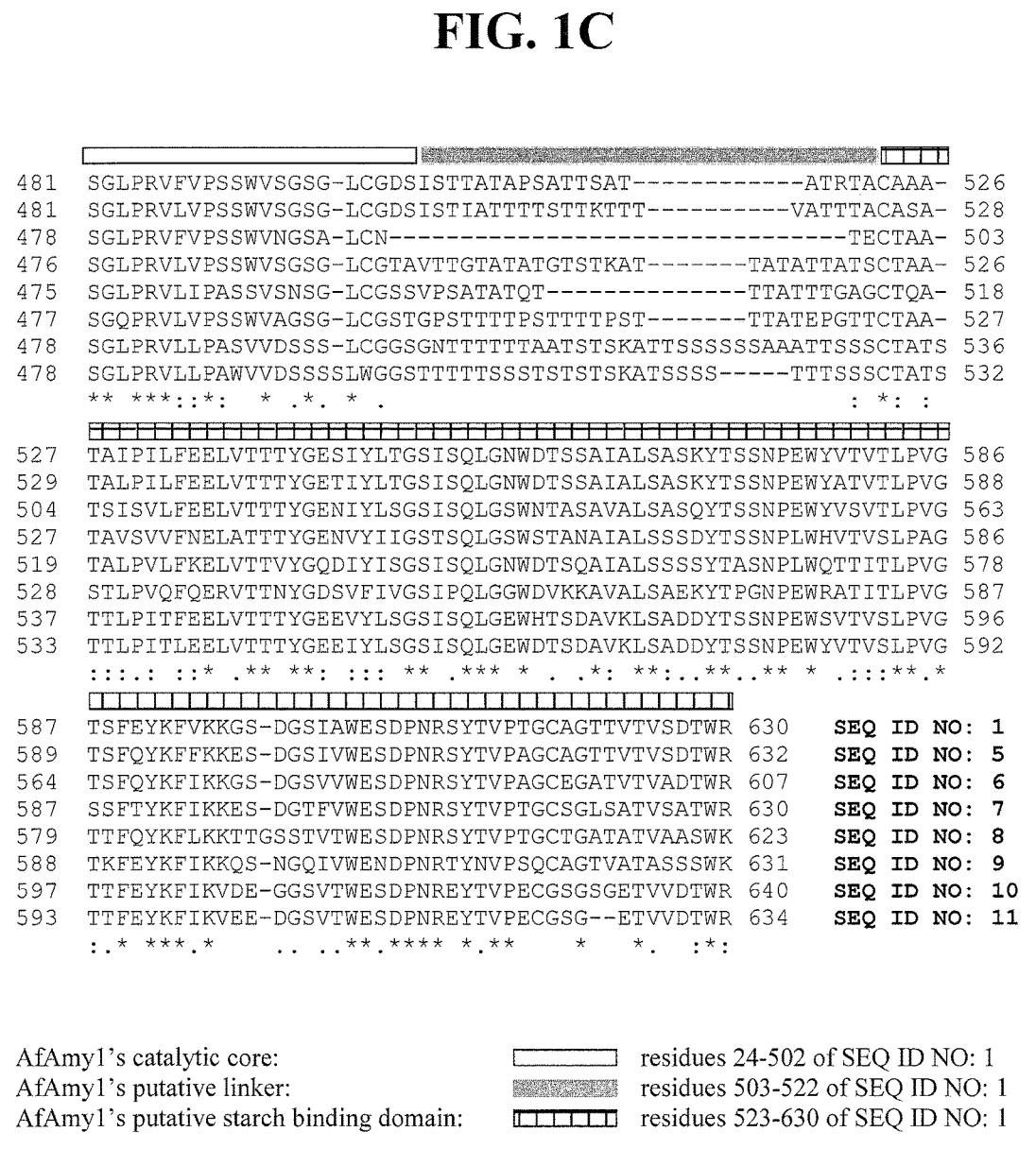

```
481  SGLPRVFVPSSWVSGSG-LCGDSISTTATAPSATTSAT------------ATRTACAAA- 526
481  SGLPRVLVPSSWVSGSG-LCGDSISTIATTTTSTTKTTT----------VATTTACASA- 528
478  SGLPRVFVPSSWVNGSA-LCN--------------------------------TECTAA- 503
476  SGLPRVLVPSSWVSGSG-LCGTAVTTGTATATGTSTKAT-------TATATTATSCTAA- 526
475  SGLPRVLIPASSVSNSG-LCGSSVPSATATQT--------------TTATTTGAGCTQA- 518
477  SGQPRVLVPSSWVAGSG-LCGSTGPSTTTTPSTTTTPST-------TTATEPGTTCTAA- 527
478  SGLPRVLLPASVVDSSS-LCGGSGNTTTTTAATSTSKATTSSSSSSAAATTSSSCTATS 536
478  SGLPRVLLPAWVVDSSSSLWGGSTTTTTSSSTSTSTSKATSSSS-----TTTSSSCTATS 532
     ** ***::*:  * .*. * .                                : *: :

527  TAIPILFEELVTTTYGESIYLTGSISQLGNWDTSSAIALSASKYTSSNPEWYVTVTLPVG 586
529  TALPILFEELVTTTYGETIYLTGSISQLGNWDTSSAIALSASKYTSSNPEWYATVTLPVG 588
504  TSISVLFEELVTTTYGENIYLSGSISQLGSWNTASAVALSASQYTSSNPEWYVSVTLPVG 563
527  TAVSVVFNELATTTYGENVYIIGSTSQLGSWSTANAIALSSSDYTSSNPLWHVTVSLPAG 586
519  TALPVLFKELVTTVYGQDIYISGSISQLGNWDTSQAIALSSSSYTASNPLWQTTITLPVG 578
528  STLPVQFQERVTTNYGDSVFIVGSIPQLGGWDVKKAVALSAEKYTPGNPEWRATITLPVG 587
537  TTLPITFEELVTTTYGEEVYLSGSISQLGEWHTSDAVKLSADDYTSSNPEWSVTVSLPVG 596
533  TTLPITLEELVTTTYGEEIYLSGSISQLGEWDTSDAVKLSADDYTSSNPEWYVTVSLPVG 592
     :::.: ::* .** **: ::: ** .*** * . .*: **:..**..** * .:::**.*

587  TSFEYKFVKKGS-DGSIAWESDPNRSYTVPTGCAGTTVTVSDTWR 630   SEQ ID NO: 1
589  TSFQYKFFKKES-DGSIVWESDPNRSYTVPAGCAGTTVTVSDTWR 632   SEQ ID NO: 5
564  TSFQYKFIKKGS-DGSVVWESDPNRSYTVPAGCEGATVTVADTWR 607   SEQ ID NO: 6
587  SSFTYKFIKKES-DGTFVWESDPNRSYTVPTGCSGLSATVSATWR 630   SEQ ID NO: 7
579  TTFQYKFLKKTTGSSTVTWESDPNRSYTVPTGCTGATATVAASWK 623   SEQ ID NO: 8
588  TKFEYKFIKKQS-NGQIVWENDPNRTYNVPSQCAGTVATASSSWK 631   SEQ ID NO: 9
597  TTFEYKFIKVDE-GGSVTWESDPNREYTVPECGSGSGETVVDTWR 640   SEQ ID NO: 10
593  TTFEYKFIKVEE-DGSVTWESDPNREYTVPECGSG--ETVVDTWR 634   SEQ ID NO: 11
     :.* ***.*    .. ..**.**** *.**    *   *.  :*:
```

AfAmy1's catalytic core: residues 24-502 of SEQ ID NO: 1
AfAmy1's putative linker: residues 503-522 of SEQ ID NO: 1
AfAmy1's putative starch binding domain: residues 523-630 of SEQ ID NO: 1

METHOD OF USING α-AMYLASE FROM *ASPERGILLUS FUMIGATUS* AND ISOAMYLASE FOR SACCHARIFICATION

CROSS REFERENCE TO RELATED APPLICATIONS

This application is the National Stage of International Application No. PCT/US2013/073317, filed on 5 Dec. 2013, which claims the benefit of International Application No. PCT/CN2012/086654, filed on 14 Dec. 2012, and are incorporated herein by reference in their entirety.

SEQUENCE LISTING

The sequence listing submitted via EFS, in compliance with 37 C.F.R. §1.52(e), is incorporated by reference.

FIELD OF THE INVENTION

Methods of using (1) an isoamylase, and (2) an α-amylase from *Aspergillus fumigatus* (AfAmyl) or a variant thereof in the saccharification of starch, for example, simultaneous saccharification and fermentation (SSF).

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup. The resulting syrup also may be fermented with microorganisms, such as yeast, to produce commercial products including ethanol, citric acid, lactic acid, succinic acid, itaconic acid, monosodium glutamate, gluconates, lysine, other organic acids, other amino acids, and other biochemicals, for example. Fermentation and saccharification can be conducted simultaneously (i.e., an SSF process) to achieve greater economy and efficiency.

α-Amylases hydrolyze starch, glycogen, and related polysaccharides by cleaving internal α-1,4-glucosidic bonds at random. α-Amylases, particularly from Bacilli, have been used for a variety of different purposes, including starch liquefaction and saccharification, textile desizing, starch modification in the paper and pulp industry, brewing, baking, production of syrups for the food industry, production of feedstocks for fermentation processes, and in animal feed to increase digestability. These enzymes can also be used to remove starchy soils and stains during dishwashing and laundry washing.

Several *Aspergillus* species, including *A. fumigatus*, show intermediate or weak amylolytic behavior. See Nehira et al. (1956) "Taxonomic studies on the genus *Aspergillus*. VIII. The relation between the morphological characteristics and the amylolytic properties in the *Aspergillus*," *Hakko Kogaku Zasshi* 34: 391-99, 423-28, 457-63. *A. fumigatus* Fresenius, for example, is capable of secreting both an alpha-amylase and a glucoamylase. See Domingues et al. (1993) "Production of amylase by soil fungi and partial biochemical characterization of amylase of a selected strain (*Aspergillus fumigatus* Fresenius)," *Can. J. Microbiol.* 39: 681-685; see also Goto et al. (1998) "Production of amylase by *Aspergillus fumigatus* utilizing α-methyl-D-glycoside, a synthetic analogue of maltose, as substrate," *FEMS Microbiol. Lett.* 167: 139-143. The optimal pH and temperature were found to be 6.0 and 50° C., respectively, for both the alpha-amylase and glucoamylase from *A. fumigatus* Fresenius. Domingues et al. (1993) *Can. J. Microbiol.* 39: 681-685.

SUMMARY

An α-amylase from *Aspergillus fumigatus* (AfAmyl) catalyzes saccharification for extended periods at moderate temperatures and an acidic pH. An example of a known α-amylase from *Aspergillus fumigatus* Af293 (SEQ ID NO: 1), a variant of the α-amylase, encoding nucleic acids, and host cells that express the polynucleotides are provided. AfAmyl has an acidic working range and contributes to high ethanol yield and low residual starch in simultaneous saccharification and fermentation (SSF), for example, particularly when used together with a glucoamylase. Despite the Domingues 1993 disclosure that the peak *A. fumigatus* amylase activity occurs at pH 6, AfAmyl has a pH optimum at pH 3.5. AfAmyl exhibits high activity at elevated temperatures and at low pH, so AfAmyl can be used efficiently in a process of saccharification in the presence of fungal glucoamylases, such as *Aspergillus niger* glucoamylase (AnGA) or *Trichoderma* glucoamylase (TrGA). AfAmyl advantageously catalyzes starch saccharification to an oligosaccharide composition significantly enriched in DP1 and DP2 (i.e., glucose and maltose) compared to the products of saccharification catalyzed by *Aspergillus kawachii* alpha-amylase (AkAA). AfAmyl can be used at a lower dosage than AkAA to produce comparable levels of ethanol. AfAmyl can be used in combination with enzymes derived from plants (e.g., cereals and grains). AfAmyl also can be used in combination with enzymes secreted by, or endogenous to, a host cell. For example, AfAmyl can be added to a fermentation or SSF process during which one or more amylases, glucoamylases, cellulases, hemicellulases, proteases, lipases, phytases, esterases, redox enzymes, transferases, or other enzymes are secreted by the production host. AfAmyl may also work in combination with endogenous non-secreted production host enzymes. In another example, AfAmyl can be secreted by a production host cell alone or with other enzymes during fermentation or SSF. The AfAmyl amylase may also be effective in direct hydrolysis of starch for syrup and/or biochemicals (e.g., alcohols, organic acids, amino acids, other biochemicals and biomaterials) where the reaction temperature is below the gelatinization temperature of substrate. AfAmyl can be secreted by a host cell with other enzymes during fermentation or SSF.

Accordingly, provided is a method of saccharifying a composition that may comprise starch to produce a composition comprising glucose, where the method may comprise (i) contacting the composition comprising starch with an isoamylase and an isolated AfAmyl or variant thereof having α-amylase activity and comprising an amino acid sequence with at least 80% amino acid sequence identity to (a) residues 24-630 of SEQ ID NO:1 or (b) residues 24-502 of SEQ ID NO:1; and (ii) saccharifying the composition comprising starch to produce the composition comprising glucose; where the isoamylase and the isolated AfAmyl or variant thereof alone or in combination with other enzymes catalyze the saccharification of the starch composition to glucose, DP2, DP3, DP4, etc., or to other oligosaccharides or polysaccharides. The saccharification may result in about 2%-11% less residual starch compared to a saccharification carried out by the isoamylase and AkAA under the same conditions.

The AfAmyl or variant thereof may be dosed at about 17%-50%, or optionally about 17%-34% the dose of AkAA, to reduce the same quantity of residual starch under the same conditions. The AfAmyl or variant thereof may also be dosed at about 17%-50%, or optionally about 17%-34% the dose of AkAA, to reduce the same quantity of DP3+ under the same conditions.

In some embodiments, the AfAmyl or variant thereof is dosed at from about 1.7 to about 10 μg protein/g solid. In further embodiments, the AfAmyl or variant thereof is dosed at from about 1.7 to about 6.6 μg protein/g solid. In yet further embodiments, the AfAmyl or variant thereof is dosed at about 3.3 μg protein/g solid.

The composition comprising glucose may be enriched in DP2 or (DP1+DP2), compared to a second composition comprising glucose produced by AkAA with isoamylase under the same conditions.

In some embodiments, the AfAmyl or variant thereof is dosed at about 33% the dose of AfAmyl that would be required to reduce the same quantity of residual starch under the same conditions in the absence of isoamylase, and optionally, wherein the isoamylase is dosed at about 13% the dose of AfAmyl that would be required to reduce the same quantity of residual starch under the same conditions in the absence of isoamylase. In further embodiments, the AfAmyl or variant thereof is dosed at about 50% the dose of AfAmyl that would be required to reduce the same quantity of DP3+ under the same conditions in the absence of isoamylase, and optionally, wherein the isoamylase is dosed at about 9% the dose of AfAmyl that would be required to reduce the same quantity of DP3+ under the same conditions in the absence of isoamylase. In yet further embodiments, the AfAmyl or variant thereof is dosed at about 33% the dose of AfAmyl that would be required to produce the same ethanol yield under the same conditions in the absence of isoamylase, and optionally, wherein the isoamylase is dosed at about 6.3% the dose of AfAmyl that would be required to produce the same ethanol yield under the same conditions in the absence of isoamylase.

The AfAmyl or variant thereof may comprise an amino acid sequence with at least 80%, 90%, 95%, or 99% amino acid sequence identity to (a) residues 24-630 of SEQ ID NO:1 or (b) residues 24-502 of SEQ ID NO:1. The AfAmyl or variant thereof may also comprise (a) residues 24-630 of SEQ ID NO:1 or (b) residues 24-502 of SEQ ID NO:1. The AfAmyl or variant thereof may consist of an amino acid sequence with at least 80%, 90%, 95%, or 99% amino acid sequence identity to (a) residues 24-630 of SEQ ID NO:1 or (b) residues 24-502 of SEQ ID NO:1. The AfAmyl or variant thereof may also consist of (a) residues 24-630 of SEQ ID NO:1 or (b) residues 24-502 of SEQ ID NO:1.

The starch composition may comprise liquefied starch, gelatinized starch, or granular starch. Saccharification may be conducted at a temperature range of about 30° C. to about 65° C. The temperature range may further be 39° C.-56° C. Saccharification may be conducted over a pH range of pH 3.0-pH 6.0. The pH range may further be pH 3.0-pH 5.5. The pH range may further be pH 3.0-pH 4.6.

The method may further comprise fermenting the glucose composition to produce an End of Fermentation (EOF) product. The fermentation may be a simultaneous saccharification and fermentation (SSF) reaction. The fermentation may be conducted for 24-70 hours at pH 2-8 and in a temperature range of 25° C.-70° C. The EOF product may comprise 8%-18% (v/v) ethanol. The EOF product may comprise a metabolite. The end product can be alcohol, or optionally ethanol. The end product also can be organic acids, amino acids, biofuels, and other biochemical, including, but not limited to, ethanol, citric acid, succinic acid, monosodium glutamate, gluconic acid, sodium gluconate, calcium gluconate, potassium gluconate, itaconic acid and other carboxylic acids, glucono delta-lactone, sodium erythorbate, lysine, omega 3 fatty acid, butanol, isoprene, 1,3-propanediol, and biodiesel.

Use of AfAmyl or variant thereof with an isoamylase in the production of a fermented beverage is also provided, as well as a method of making a fermented beverage which may comprise: contacting a mash and/or a wort with AfAmyl or variant thereof with an isoamylase. A method of making a fermented beverage which may comprise: (a) preparing a mash; (b) filtering the mash to obtain a wort; and (c) fermenting the wort to obtain a fermented beverage, where AfAmyl or variant thereof with an isoamylase are added to: (i) the mash of step (a) and/or (ii) the wort of step (b) and/or (iii) the wort of step (c). A fermented beverage produced by the disclosed methods is also provided.

The fermented beverage or end of fermentation product can be selected from the group consisting of a beer selected such as full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, and non-alcoholic malt liquor; or cereal or malt beverages such as fruit flavoured malt beverages, liquor flavoured malt beverages, and coffee flavoured malt beverages.

The method may further comprise adding glucoamylase, trehalase, hexokinase, xylanase, glucose isomerase, xylose isomerase, phosphatase, phytase, pullulanase, β-amylase, α-amylase that is not AfAmyl, protease, cellulase, hemicellulase, lipase, cutinase, isoamylase, redox enzyme, esterase, transferase, pectinase, alpha-glucosidase, beta-glucosidase, lyase or other hydrolases, or a combination thereof, to the starch composition. See, e.g., WO 2009/099783. Glucoamylase may be added to 0.1-2 glucoamylase units (GAU)/g ds.

The isolated AfAmyl or a variant thereof may be expressed and secreted by a host cell. The starch composition may be contacted with the host cell. The host cell may further express and secrete a glucoamylase and/or other enzymes. In preferred embodiments, the other enzyme is an isoamylase. The host cell may further be capable of fermenting the glucose composition.

Accordingly, provided is a composition for the use of saccharifying a composition comprising starch, that may comprise an isolated AfAmyl or variant thereof having α-amylase activity and comprising an amino acid sequence with at least 80%, 90%, 95%, 99% or 100% amino acid sequence identity to (a) residues 24-630 of SEQ ID NO:1 or (b) residues 24-502 of SEQ ID NO:1. The AfAmyl or variant thereof may consist of an amino acid sequence with at least 80%, 90%, 95%, 99%, or 100% amino acid sequence identity to (a) residues 24-630 of SEQ ID NO:1 or (b) residues 24-502 of SEQ ID NO:1.

The composition may be a cultured cell material. The composition may further comprise a glucoamylase. The AfAmyl or variant thereof and/or isoamylase may also be purified.

The AfAmyl or variant thereof and/or isoamylase may be expressed and secreted by a host cell. The host cell may be a filamentous fungal cell, a bacterial cell, a yeast cell, a plant cell or an algal cell. The host cell may be an *Aspergillus* sp. or *Trichoderma reesei* cell.

Accordingly, provided is a method of baking comprising adding a baking composition to a substance to be baked, and baking the substance to produce a baked good, where the baking composition comprises an isoamylase and an isolated AfAmyl or variant thereof having α-amylase activity and comprising an amino acid sequence with at least 80%, 90%, 95%, 99% or 100% amino acid sequence identity to (a) residues 24-630 of SEQ ID NO:1 or (b) residues 24-502 of SEQ ID NO:1, where the isolated AfAmyl or variant thereof catalyzes the hydrolysis of starch components present in the substance to produce smaller starch-derived molecules. The AfAmyl or variant thereof may consist of an amino acid sequence with at least 80%, 90%, 95%, 99%, or 100% amino acid sequence identity to (a) residues 24-630 of SEQ ID NO:1 or (b) residues 24-502 of SEQ ID NO:1. The baking composition may further comprise flour, an anti-staling amylase, a phospholipase, and/or a phospholipid.

Accordingly, also provided is a method of producing a food composition, comprising combining (i) one or more food ingredients, and (ii) an isoamylase and an isolated AfAmyl or variant thereof having α-amylase activity and comprising an amino acid sequence with at least 80%, 90%, 95%, 99% or 100% amino acid sequence identity to (a) residues 24-630 of SEQ ID NO:1 or (b) residues 24-502 of SEQ ID NO:1, wherein the isoamylase and the isolated AfAmyl or variant thereof catalyze the hydrolysis of starch components present in the food ingredients to produce glucose. The AfAmyl or variant thereof may consist of an amino acid sequence with at least 80%, 90%, 95%, 99%, or 100% amino acid sequence identity to (a) residues 24-630 of SEQ ID NO:1 or (b) residues 24-502 of SEQ ID NO:1. The method may further comprise baking the food composition to produce a baked good. The method may further comprise (i) providing a starch medium; (ii) adding to the starch medium the isoamylase and the AfAmyl or variant thereof; and (iii) applying heat to the starch medium during or after step (b) to produce a bakery product.

The food composition may be enriched in DP2 or (DP1+DP2), compared to a second baked good produced by AkAA with an isoamylase under the same conditions. The food composition may be selected from the group consisting of a food product, a baking composition, a food additive, an animal food product, a feed product, a feed additive, an oil, a meat, and a lard. The food composition may comprise a dough or a dough product, preferably a processed dough product.

The one or more food ingredients may comprise a baking ingredient or an additive. The one or more food ingredients may also be selected from the group consisting of flour; an anti-staling amylase; a phospholipase; a phospholipid; a maltogenic alpha-amylase or a variant, homologue, or mutants thereof which has maltogenic alpha-amylase activity; a bakery xylanase (EC 3.2.1.8); and a lipase. The one or more food ingredients may further be selected from the group consisting of (i) a maltogenic alpha-amylase from *Bacillus stearothermophilus*, (ii) a bakery xylanase is from *Bacillus, Aspergillus, Thermomyces* or *Trichoderma*, (iii) a glycolipase from *Fusarium heterosporum*.

Accordingly, also provided is a composition for use producing a food composition, comprising an isoamylase and an isolated AfAmyl or variant thereof having α-amylase activity and comprising an amino acid sequence with at least 80% amino acid sequence identity to (a) residues 24-630 of SEQ ID NO:1 or (b) residues 24-502 of SEQ ID NO:1 and one or more food ingredients. Also provided is a use of the isoamylase and the AfAmyl or variant thereof of any one of claims 74-78 in preparing a food composition. The food composition may comprise a dough or a dough product, including a processed dough product. The food composition may be a bakery composition. The AfAmyl or variant thereof may be used in a dough product to retard or reduce staling, preferably detrimental retrogradation, of the dough product.

Accordingly, provided is a method of removing starchy stains from laundry, dishes, or textiles, which may comprise incubating a surface of the laundry, dishes, or textiles in the presence of an aqueous composition comprising an effective amount of an isoamylase and an isolated AfAmyl or variant thereof having α-amylase activity and comprising an amino acid sequence with at least 80%, 90%, 95%, 99% or 100% amino acid sequence identity to (a) residues 24-630 of SEQ ID NO:1 or (b) residues 24-502 of SEQ ID NO:1, and allowing the isoamylase and the AfAmyl or variant thereof to hydrolyze starch components present in the starchy stain to produce smaller starch-derived molecules that dissolve in the aqueous composition, and rinsing the surface, thereby removing the starchy stain from the surface. The AfAmyl or variant thereof may consist of an amino acid sequence with at least 80%, 90%, 95%, 99%, or 100% amino acid sequence identity to (a) residues 24-630 of SEQ ID NO:1 or (b) residues 24-502 of SEQ ID NO:1.

Accordingly, provided is a composition for use in removing starchy stains from laundry, dishes, or textiles, which may comprise an isoamylase and an isolated AfAmyl or variant thereof having α-amylase activity and comprising an amino acid sequence with at least 80%, 90%, 95%, 99% or 100% amino acid sequence identity to (a) residues 24-630 of SEQ ID NO:1 or (b) residues 24-502 of SEQ ID NO:1 and a surfactant. The AfAmyl or variant thereof may consist of an amino acid sequence with at least 80%, 90%, 95%, 99%, or 100% amino acid sequence identity to (a) residues 24-630 of SEQ ID NO:1 or (b) residues 24-502 of SEQ ID NO:1. The composition may be a laundry detergent, a laundry detergent additive, or a manual or automatic dishwashing detergent.

Accordingly, a method of desizing a textile is also provided, that may comprise contacting a desizing composition with a textile for a time sufficient to desize the textile, where the desizing composition may comprise an isoamylase and an isolated AfAmyl or variant thereof having α-amylase activity and comprising an amino acid sequence with at least 80%, 90%, 95%, 99% or 100% amino acid sequence identity to (a) residues 24-630 of SEQ ID NO:1 or (b) residues 24-502 of SEQ ID NO:1 and allowing the AfAmyl or variant thereof to desize starch components present in the starchy stain to produce smaller starch-derived molecules that dissolve in the aqueous composition, and rinsing the surface, thereby removing the starchy stain from the surface. The AfAmyl or variant thereof may consist of an amino acid sequence with at least 80%, 90%, 95%, 99%, or 100% amino acid sequence identity to (a) residues 24-630 of SEQ ID NO:1 or (b) residues 24-502 of SEQ ID NO:1.

Accordingly, use of an isoamylase and AfAmyl or variant thereof in the production of a glucose composition is also provided. A glucose composition produced by the disclosed methods is also provided. Use of an isoamylase and AfAmyl or variant thereof in the production of a liquefied starch is further provided. And a liquefied starch prepared by the disclosed methods is also disclosed.

Moreover, use of a desizing composition which may comprise an isoamylase and AfAmyl or variant thereof in desizing textiles is disclosed, as well as use of a baking composition which may comprise AfAmyl or variant thereof in the production of a baked good.

BRIEF DESCRIPTION OF THE DRAWINGS

The accompanying drawings are incorporated in and constitute a part of this specification and illustrate various methods and compositions disclosed herein. In the drawings:

FIG. 1A, FIG. 1B, and FIG. 1C depict a ClustalW alignment of the catalytic core, putative linker region, and putative carbohydrate binding domain of AfAmyl with the corresponding residues of the α-amylases from: *N. fischeri* NRRL181 (SEQ ID NO: 5); *A. terreus* NIH2624 (SEQ ID NO: 6); *O. floccosum* (SEQ ID NO: 7); *P. chrysogenum* Wisconsin 54-1255 (SEQ ID NO: 8); *A. clavatus* NRRL 1 (SEQ ID NO: 9); *A. kawachii* (SEQ ID NO; 10); and *A. awamori* (SEQ ID NO: 11). Residues designated by an asterisk in FIG. 1 are AfAmyl residues corresponding to conserved residues in SEQ ID NOS: 5-11.

DETAILED DESCRIPTION

Figure 2:
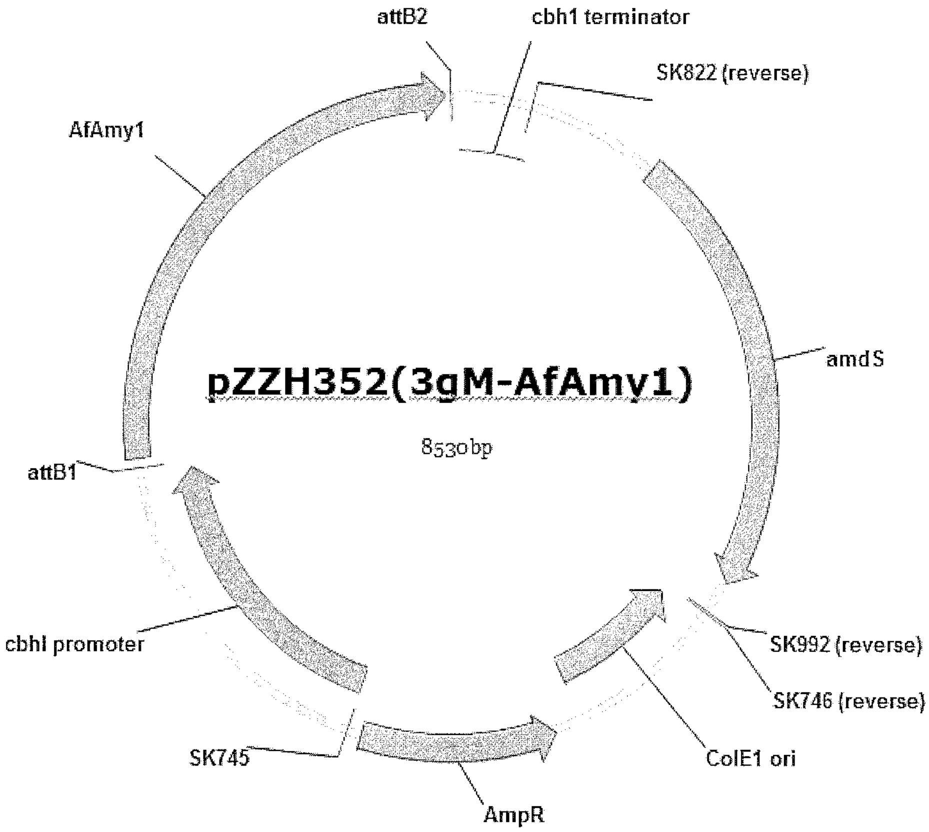
FIG. 2 depicts a map of a pZZH352 expression vector comprising a polynucleotide that encodes an AfAmyl polypeptide, pZZH352(3 gM-AfAmyl).

A fungal α-amylase from *Aspergillus fumigatus* (AfAmyl) is provided. AfAmyl has a pH optimum of pH 3.5 and at least 70% activity over a range of pH 3 to pH 4.6. The enzyme has an optimum temperature of 50° C. and at least 70% activity over a temperature range of 39-56° C., when tested at pH 3.5. These properties allow the enzyme to be used in combination with a glucoamylase and/or other enzymes under the same reaction conditions. In preferred embodiments, the other enzyme is an isoamylase. This obviates the necessity of running a saccharification reaction as a batch process, where the pH and temperature must be adjusted for optimal use of the α-amylase or glucoamylase.

AfAmyl and an isoamylase also catalyze the saccharification of a composition comprising starch to glucose. For example, after two hours of saccharification at 50° C., pH 5.3, using a DP7, amylopectin, or maltodextrin substrate, an oligosaccharide composition can be produced. The composition is enriched in DP2 and (DP1+DP2), compared to the products of isoamylase and AkAA-catalyzed saccharification under the same conditions. This facilitates the utilization of the oligosaccharide composition by a fermenting organism in a SSF process, for example. In this role, AfAmyl can produce the same ethanol yield as AkAA with a lower enzyme dosage, while reducing residual starch and minimizing any negative effects of residual starch on final product quality.

In some embodiments, the AfAmyl or variant thereof in the presence of isoamylase is dosed at about 33% the dose of AfAmyl that would be required to reduce the same quantity of residual starch under the same conditions in the absence of isoamylase, and optionally, wherein the isoamylase is dosed at about 13% the dose of AfAmyl that would be required to reduce the same quantity of residual starch under the same conditions in the absence of isoamylase. In further embodiments, the AfAmyl or variant thereof in the presence of isoamylase is dosed at about 50% the dose of AfAmyl that would be required to reduce the same quantity of DP3+ under the same conditions in the absence of isoamylase, and optionally, wherein the isoamylase is dosed at about 9% the dose of AfAmyl that would be required to reduce the same quantity of DP3+ under the same conditions in the absence of isoamylase. In yet further embodiments, the AfAmyl or variant thereof in the presence of isoamylase is dosed at about 33% the dose of AfAmyl that would be required to produce the same ethanol yield under the same conditions in the absence of isoamylase, and optionally, wherein the isoamylase is dosed at about 6.3% the dose of AfAmyl that would be required to produce the same ethanol yield under the same conditions in the absence of isoamylase.

Exemplary applications for AfAmyl and variants thereof amylases are in a process of starch saccharification, e.g., SSF, the preparation of cleaning compositions, such as detergent compositions for cleaning laundry, dishes, and other surfaces, for textile processing (e.g., desizing).

1. Definitions & Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. The following terms are provided below.

1.1. Abbreviations and Acronyms

The following abbreviations/acronyms have the following meanings unless otherwise specified:

ABTS 2,2-azino-bis-3-ethylbenzothiazoline-6-sulfonic acid

AfAmyl *Aspergillus fumigatus* α-amylase

AE alcohol ethoxylate

AEO alcohol ethoxylate

AEOS alcohol ethoxysulfate

AES alcohol ethoxysulfate

AkAA *Aspergillus kawachii* α-amylase

AnGA *Aspergillus niger* glucoamylase
AOS α-olefinsulfonate
AS alkyl sulfate
cDNA complementary DNA
CMC carboxymethylcellulose
DE dextrose equivalent
DNA deoxyribonucleic acid
DPn degree of saccharide polymerization having n subunits
ds or DS dry solids
DTMPA diethylenetriaminepentaacetic acid
EC Enzyme Commission
EDTA ethylenediaminetetraacetic acid
EO ethylene oxide (polymer fragment)
EOF End of Fermentation
FGSC Fungal Genetics Stock Center
GA glucoamylase
GAU/g ds glucoamylase activity unit/gram dry solids
HFCS high fructose corn syrup
HgGA *Humicola grisea* glucoamylase
IPTG isopropyl β-D-thiogalactoside
IRS (insoluble) residual starch
Iso Isoamylase
kDa kiloDalton
LAS linear alkylbenzenesulfonate
MW molecular weight
MWU modified Wohlgemuth unit; $1.6\times10^{-5}$ mg/MWU=unit of activity
NCBI National Center for Biotechnology Information
NOBS nonanoyloxybenzenesulfonate
NTA nitriloacetic acid
OxAm Purastar HPAM 5000L (Danisco US Inc.)
PAHBAH p-hydroxybenzoic acid hydrazide
PEG polyethyleneglycol
pI isoelectric point
ppm parts per million, e.g., μg protein per gram dry solid
PVA poly(vinyl alcohol)
PVP poly(vinylpyrrolidone)
RNA ribonucleic acid
SAS alkanesulfonate
SDS-PAGE sodium dodecyl sulfate polyacrylamide gel electrophoresis
SSF simultaneous saccharification and fermentation
SSU/g solid soluble starch unit/gram dry solids
sp. species
TAED tetraacetylethylenediamine
TrGA *Trichoderma reesei* glucoamylase
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm grams
μg micrograms
mg milligrams
kg kilograms
μL and μl microliters
mL and ml milliliters
mm millimeters
μm micrometer
M molar
mM millimolar
μM micromolar
U units
sec seconds
min(s) minute/minutes
hr(s) hour/hours
DO dissolved oxygen
Ncm Newton centimeter
ETOH ethanol
eq. equivalents
N normal 1.2. Definitions The terms "amylase" or "amylolytic enzyme" refer to an enzyme that is, among other things, capable of catalyzing the degradation of starch. α-Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion yielding polysaccharides containing three or more (1→4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

The term "pullulanase" (E.C. 3.2.1.41, pullulan 6-glucanohydrolase) refers to a class of enzymes that are capable of hydrolyzing α-1,6-D-glucosidic linkages present in amylopectin. Pullulanase hydrolyses the α-1,6-D-glucosidic linkages in pullulan to give the trisaccharide maltotriose.

The term "isoamylase," as used herein, refers to a debranching enzyme (E.C. 3.2.1.68) capable of hydrolyzing the α-1,6-D-glucosidic linkages of starch, glycogen, amylopectin, glycogen, beta-limit dextrins, and oligosaccharides derived therefrom. It cannot hydrolyse pullulan.

"Enzyme units" herein refer to the amount of product formed per time under the specified conditions of the assay. For example, a "glucoamylase activity unit" (GAU) is defined as the amount of enzyme that produces 1 g of glucose per hour from soluble starch substrate (4% DS) at 60° C., pH 4.2. A "soluble starch unit" (SSU) is the amount of enzyme that produces 1 mg of glucose per minute from soluble starch substrate (4% DS) at pH 4.5, 50° C. DS refers to "dry solids."

As used herein the term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, cereal, grasses, tubers and roots, and more specifically materials obtained from wheat, barley, corn, rye, rice, sorghum, brans, cassava, millet, potato, sweet potato, and tapioca. The term "starch" includes granular starch. The term "granular starch" refers to raw, i.e., uncooked starch, e.g., starch that has not been subject to gelatinization.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type protein is understood to include the mature form of the protein. A "mature" polypeptide means an AfAmyl polypeptide or variant thereof from which a signal sequence is absent. For example, the signal sequence may be cleaved during expression of the polypeptide. The mature AfAmyl is 617 amino acids in length covering positions 24-630 of SEQ ID NO: 1, where positions are counted from the N-terminus. The signal sequence of the wild-type AfAmyl is 23 amino acids in length and has the sequence set forth in SEQ ID NO: 4. A mature AfAmyl or variant thereof may comprise a signal sequence taken from different proteins. The mature protein can be a fusion protein between the mature polypeptide and a signal sequence polypeptide.

The "catalytic core" of AfAmyl spans residues 24-502 of SEQ ID NO: 1. The putative "linker" or "linker region" of AfAmyl span residues 503-522. The amino acid residues 523-630 constitute the putative "carbohydrate binding domain" of AfAmyl.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context. A "variant" of AfAmyl and a "variant α-amylase polypeptide" are synonymous herein.

In the case of the present α-amylases, "activity" refers to α-amylase activity, which can be measured as described, herein.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an AfAmyl or variant thereof is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature, e.g., an AfAmyl isolated from an *A. fumigatus* sp. cell. An "isolated" AfAmyl or variant thereof includes, but is not limited to, a culture broth containing secreted AfAmyl or variant polypeptides and AfAmyl or variant polypeptides expressed in a heterologous host cell (i.e., a host cell that is not *A. fumigatus*).

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

As used herein, the terms "pH stable" and "pH stability," with reference to an enzyme, relate to the ability of the enzyme to retain activity over a wide range of pH values for a predetermined period of time (e.g., 15 min., 30 min., 1 hour).

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

As used herein, "hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1× SSC=0.15 M NaCl, 0.015 M $Na_3$ citrate, pH 7.0). Hybridized, duplex nucleic acids are characterized by a melting temperature ($T_m$), where one-half of the hybridized nucleic acids are unpaired with the complementary strand. Mismatched nucleotides within the duplex lower the $T_m$. A nucleic acid encoding a variant α-amylase may have a $T_m$ reduced by 1° C.-3° C. or more compared to a duplex formed between the nucleotide of SEQ ID NO: 2 or SEQ ID NO: 3 and its identical complement.

As used herein, a "synthetic" molecule is produced by in vitro chemical or enzymatic synthesis rather than by an organism.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., AfAmyl or variant thereof) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity.

As used herein, a "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

As used herein, a "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

As used herein, "a cultured cell material comprising an AfAmyl or variant thereof," or similar language, refers to a cell lysate or supernatant (including media) that includes an AfAmyl or variant thereof as a component. The cell material may be from a heterologous host that is grown in culture for the purpose of producing the AfAmyl or variant thereof.

"Percent sequence identity" means that a variant has at least a certain percentage of amino acid residues identical to a wild-type AfAmyl, when aligned using the CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence. Deletions occurring at either termini are included. For example, a variant with five amino acid deletions of the C-terminus of the mature AfAmyl polypeptide of SEQ ID NO: 1 would have a percent sequence identity of 99% (625/630 identical residues×100, rounded to the nearest whole number) relative to the mature polypeptide. Such a variant would be encompassed by a variant having "at least 99% sequence identity" to a mature AfAmyl polypeptide.

"Fused" polypeptide sequences are connected, i.e., operably linked, via a peptide bond between the two polypeptide sequences.

The term "filamentous fungi" refers to all filamentous forms of the subdivision Eumycotina.

The term "degree of polymerization" (DP) refers to the number (n) of anhydro-glucopyranose units in a given saccharide. Examples of DP1 are the monosaccharides glucose and fructose. Examples of DP2 are the disaccharides maltose and sucrose. The term "DE," or "dextrose equivalent," is defined as the percentage of reducing sugar, i.e., D-glucose, as a fraction of total carbohydrate in a syrup.

As used herein the term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanologenic microorganism, and at least one enzyme, such as AfAmyl or a variant thereof, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

As used herein "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or yeast fermentation.

"Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material which is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

"Iodine-positive starch" or "IPS" refers to (1) amylose that is not hydrolyzed after liquefaction and saccharification, or (2) a retrograded starch polymer. When saccharified starch or saccharide liquor is tested with iodine, the high DPn amylose or the retrograded starch polymer binds iodine and produces a characteristic blue color. The saccharide liquor is thus termed "iodine-positive saccharide," "blue saccharide," or "blue sac."

The terms "retrograded starch" or "starch retrogradation" refer to changes that occur spontaneously in a starch paste or gel on ageing.

The term "about" refers to ±15% of the referenced value.

2. *Aspergillus fumigatus* α-Amylase (AfAmyl) and Variants Thereof

An isolated and/or purified AfAmyl polypeptide from *A. fumigatus* sp. or a variant thereof having α-amylase activity is provided. The AfAmyl polypeptide can be the mature AfAmyl polypeptide comprising residues 24-630 of the polypeptide sequence depicted in SEQ ID NO: 1. The polypeptides may be fused to additional amino acid sequences at the N-terminus and/or C-terminus. Additional N-terminal sequences can be a signal peptide, which may have the sequence shown in SEQ ID NO: 4, for example. Other amino acid sequences fused at either termini include fusion partner polypeptides useful for labeling or purifying the protein.

For example, a known α-amylase from *A. fumigatus* is the α-amylase from *A. fumigatus* Af293. *A. fumigatus* Af293 α-amylase precursor, i.e., containing a signal peptide has the following amino acid sequence (SEQ ID NO: 1):

```
MKWIAQLFPLSLCSSLLGQAAHALTPAEWRSQSIYFLLTDRFGREDNSTTAACDVTQRLYCGGS

WQGIINHLDYIQGMGFTAIWITPVTEQFYENTGDGTSYHGYWQQNIHEVNANYGTAQDLRDLAN

ALHARGMYLMVDVVANHMGYNGAGNSVNYGVFTPFDSATYFHPYCLITDYNNQTAVEDCWLGDT

TVSLPDLDTTSTAVRSIWYDWVKGLVANYSIDGLRIDTVKHVEKDFWPGYNDAAGVYCVGEVFS

GDPQYTCPYQNYLDGVLNYPIYYQLLYAFQSTSGSISNLYNMISSVASDCADPTLLGNFIENHD

NPRFASYTSDYSQAKNVISFMFFSDGIPIVYAGQEQHYSGGADPANREAVWLSGYSTSATLYSW

IASTNKIRKLAISKDSAYITSKNNPFYYDSNTLAMRKGSVAGSQVITVLSNKGSSGSSYTLSLS

GTGYSAGATLVEMYTCTTLTVDSSGNLAVPMVSGLPRVFVPSSWVSGSGLCGDSISTTATAPSA

TTSATATRTACAAATAIPILFEELVTTTYGESIYLTGSISQLGNWDTSSAIALSASKYTSSNPE

WYVTVTLPVGTSFEYKFVKKGSDGSIAWESDPNRSYTVPTGCAGTTVTVSDTWR
```

See NCBI Reference Number XP_749208.1 (>gi|70988703|ref|XP_749208.1| alpha-amylase [*Aspergillus fumigatus* Af293]). The putative alpha-amylase from *Aspergillus fumigatus* A1163 (>gi|159128622|gb|EDP53736.1| alpha-amylase, putative [*Aspergillus fumigatus* A1163]), having the amino acid sequence of SEQ ID NO: 16, differs from SEQ ID NO: 1 by one amino acid residue at position 5, which is located in the signal peptide.

The bolded amino acids above constitute a putative C-terminal carbohydrate binding (CBM) domain (SEQ ID NO:

14). A putative glycosylated linker region (highlighted, bolded amino acids above; SEQ ID NO: 15) connects the N-terminal catalytic core with the putative CBM domain. The putative CBM domain in AfAmyl is conserved with a CBM20 domain found in a large number of starch degrading enzymes, including alpha-amylases, beta-amylases, glucoamylases, and cyclodextrin glucanotransferases. CBM20 folds as an antiparallel beta-barrel structure with two starch binding sites 1 and 2. These two sites are thought to differ functionally: site 1 may act as the initial starch recognition site, whereas site 2 may be involved in specific recognition of appropriate regions of starch. See Sorimachi et al. (1997) "Solution structure of the granular starch binding domain of *Aspergillus niger* glucoamylase bound to beta-cyclodextrin," *Structure* 5(5): 647-61. Residues in the AfAmyl putative CBM domain that are conserved with starch binding sites 1 and 2 are indicated in the sequence below by the numbers 1 and 2, respectively:

```
                                     (SEQ ID NO: 14)
CAAATAIPILFEELVTTTYGESIYLTGSISQLGNWDTSSAIALSASKYTS
             222222        1    1 1111      2 2222

SNPEWYVTVTLPVGTSFEYKFVKKGSDGSIAWESDPNRSYTVPTGCAGTT
  22                           1

VTVSDTWR.
```

A variant AfAmyl may comprise some or no amino acid residues of the putative CBM domain of SEQ ID NO: 14 or the linker of SEQ ID NO: 15. A variant alternatively may comprise a CBM domain with at least 80%, 85%, 90%, 95%, or 98% sequence identity to the putative CBM domain of SEQ ID NO: 14. A variant may comprise a heterologous or an engineered CBM20 domain.

The AfAmyl or variant thereof may be expressed in a eukaryotic host cell, e.g., a filamentous fungal cell, that allows proper glycosylation of the linker sequence, for example.

A representative polynucleotide encoding AfAmyl is the polynucleotide sequence set forth in SEQ ID NO: 2 or SEQ ID NO: 3. The polypeptide sequence, MKWIAQLFPLSLCSSLLGQAAHA (SEQ ID NO: 4), shown in italics above, is an N-terminal signal peptide that is cleaved when the protein is expressed in an appropriate host cell.

The polypeptide sequence of AfAmyl is similar to other fungal alpha-amylases. For example, AfAmyl has a high sequence identity to the following fungal α-amylases:

- 93% sequence identity to the putative alpha-amylase from *Neosartorya fischeri* NRRL 181 (XP_001265628.1; SEQ ID NO: 5);
- 82% sequence identity to the alpha-amylase precursor from *Aspergillus terreus* NIH2624 (XP_001209405.1; SEQ ID NO: 6);
- 75% sequence identity to the alpha-amylase AMYI from *Ophiostoma floccosum* (ABF72529.1; SEQ ID NO: 7);
- 73% sequence identity to the hypothetical protein Pc16g00630 from *Penicillium chrysogenum* Wisconsin 54-1255 (XP_002560482.1; SEQ ID NO: 8);
- 69% sequence identity to the putative alpha-amylase from *Aspergillus clavatus* NRRL 1 (XP_001273134.1; SEQ ID NO: 9);
- 70% sequence identity to the acid-stable alpha-amylase from *Aspergillus kawachii* (BAA22993.1; SEQ ID NO: 10); and
- 71% sequence identity to the alpha-amylase from *Aspergillus awamori* (BAD06003.1; SEQ ID NO: 11).

Sequence identity was determined by a BLAST alignment, using the mature form of the AfAmyl of SEQ ID NO: 1 (i.e., residues 24-630) as the query sequence. See Altschul et al. (1990) *J Mol. Biol.* 215: 403-410.

A variant of an AfAmyl polypeptide is provided. The variant can consist of or comprise a polypeptide with at least 80%, at least 90%, at least 95%, at least 98%, or at least 99% amino acid sequence identity to the polypeptide of residues 24-630 or residues 24-502 of SEQ ID NO:1, wherein the variant comprises one or more amino acid modifications selected from a substitution, insertion, or deletion of one or more corresponding amino acids in SEQ ID NO: 5, 6, 7, 8, 9, 10, and/or 11. For example, a variant consisting of a polypeptide with at least 99% sequence identity to the polypeptide of residues 24-630 of SEQ ID NO:1 may have one to six amino acid substitutions, insertions, or deletions, compared to the AfAmyl of SEQ ID NO: 1. By comparison, a variant consisting of a polypeptide with at least 99% sequence identity to the polypeptide of residues 24-502 of SEQ ID NO:1 would have up to five amino acid modifications. The insertions or deletions may be at either termini of the polypeptide, for example. Alternatively, the variant can "comprise" a polypeptide consisting of a polypeptide with at least 80%, at least 90%, at least 95%, at least 98%, or at least 99% amino acid sequence identity to the polypeptide of residues 24-630 or 24-502 of SEQ ID NO: 1. In such a variant, additional amino acid residues may be fused to either termini of the polypeptide. For example, the variant may comprise the signal sequence of SEQ ID NO: 4 fused in-fame with a polypeptide with one or more amino acid substitutions or deletions compared to the polypeptide of residues 24-630 of SEQ ID NO:1. The variant may be glycosylated, regardless of whether the variant "comprises" or "consists" of a given amino acid sequence.

A ClustalW alignment between AfAmyl (SEQ ID NO: 1) and the α-amylases from *N. fischeri* NRRL181 (SEQ ID NO: 5); *A. terreus* NIH2624 (SEQ ID NO: 6); *O. floccosum* (SEQ ID NO: 7); *P. chrysogenum* Wisconsin 54-1255 (SEQ ID NO: 8); *A. clavatus* NRRL 1 (SEQ ID NO: 9); *A. kawachii* (SEQ ID NO; 10); and *A. awamori* (SEQ ID NO: 11) is shown in FIG. 1. See Thompson et al. (1994) *Nucleic Acids Res.* 22:4673-4680. As a general rule, the degree to which an amino acid is conserved in an alignment of related protein sequences is proportional to the relative importance of the amino acid position to the function of the protein. That is, amino acids that are common in all related sequences likely play an important functional role and cannot be easily substituted. Likewise, positions that vary between the sequences likely can be substituted with other amino acids or otherwise modified, while maintaining the activity of the protein.

The crystal structure of *A. niger* α-amylase has been determined, including a complex of enzyme with maltose bound to its active site. See, e.g., Vujicić-Zagar et al. (2006) "Monoclinic crystal form of *Aspergillus niger* α-amylase in complex with maltose at 1.8 Å resolution," *Acta Crystallogr. Sect. F: Struct. Biol. Cryst. Commun.* 62(8):716-21. The *A. niger* α-amylase disclosed in Vujicić-Zagar (2006) is also known as TAKA-amylase, an *A. oryzae* α-amylase homologue. The amino acid sequence of TAKA-amylase (SEQ ID NO: 17) has a 69% sequence identity to AfAmyl over AfAmyl residues 24-502, when aligned using the BLAST algorithm. Given the relatively high amino acid sequence conservation between TAKA-amylase and AfAmyl, AfAmyl is expected to adopt many of the secondary structures and possess similar structure/function relationships as TAKA-amylase. For example, AfAmyl is expected to have a similar high affinity $Ca^{2+}$ binding site and maltose binding cleft as TAKA-amylase. Consistent with this expectation, the three acidic amino acids that participate in the hydrolysis reaction catalyzed by TAKA-amylase, D206, E230, and D297, all are conserved in the wild-type AfAmyl. TAKA-amylase positions Y155, L166, and D235, located near the binding cleft, also are conserved in AfAmyl. Other conserved AfAmyl positions correspond to N121, E162, D175, and H210 of TAKA-amylase, which constitute the high affinity $Ca^{2+}$ binding site. See Vujicić-Zagar (2006).

The alignments shown in FIG. 1 and the structural relationships ascertained from the TAKA-amylase crystal structure, for example, can guide the construction of variant AfAmyl polypeptides having α-amylase activity. Variant AfAmyl polypeptides include, but are not limited to, those with an amino acid modification selected from a substitution, insertion, or deletion of a corresponding amino acid in SEQ ID NO: 5, 6, 7, 8, 9, 10, and/or 11. Correspondence between positions in AfAmyl and the α-amylases of SEQ ID NOS: 5-11 is determined with reference to the alignment shown in FIG. 1. For example, a variant AfAmyl polypeptide can have the substitution D54N, where asparagine (N) is the corresponding amino acid in SEQ ID NOS: 7-8 and 10, referring to the alignment in FIG. 1. Variant AfAmyl polypeptides also include, but are not limited to, those with 1, 2, 3, or 4 randomly selected amino acid modifications. Amino acid modifications can be made using well-known methodologies, such as oligo-directed mutagenesis.

Nucleic acids encoding the AfAmyl polypeptide or variant thereof also are provided. A nucleic acid encoding AfAmyl can be genomic DNA. Or, the nucleic acid can be a cDNA comprising SEQ ID NO: 3. As is well understood by one skilled in the art, the genetic code is degenerate, meaning that multiple codons in some cases may encode the same amino acid. Nucleic acids include all genomic DNA, mRNA and cDNA sequences that encode an AfAmyl or variant thereof.

The AfAmyl or variants thereof may be "precursor," "immature," or "full-length," in which case they include a signal sequence, or "mature," in which case they lack a signal sequence. The variant α-amylases may also be truncated at the N- or C-termini, so long as the resulting polypeptides retain α-amylase activity.

2.1. AfAmyl Variant Characterization

Variant AfAmyl polypeptides retain α-amylase activity. They may have a specific activity higher or lower than the wild-type AfAmyl polypeptide. Additional characteristics of the AfAmyl variant include stability, pH range, oxidation stability, and thermostability, for example. For example, the variant may be pH stable for 24-60 hours from pH 3 to about pH 7, e.g., pH 3.0-7.5; pH 3.5-5.5; pH 3.5-5.0; pH 3.0-4.6; pH 3.2-4.0; pH 3.5, or pH 3.8. An AfAmyl variant can be expressed at higher levels than the wild-type AfAmyl, while retaining the performance characteristics of the wild-type AfAmyl. AfAmyl variants also may have altered oxidation stability in comparison to the parent α-amylase. For example, decreased oxidation stability may be advantageous in composition for starch liquefaction. The variant AfAmyl may have altered thermostability compared to the wild-type α-amylase. Such AfAmyl variants are advantageous for use in baking or other processes that require elevated temperatures. Levels of expression and enzyme activity can be assessed using standard assays known to the artisan skilled in this field, including those disclosed below. The AfAmyl variant may have one or more altered biochemical, physical and/or performance properties compared to the wild type enzyme.

3. Production of AfAmyl and Variants Thereof

The AfAmyl or variant thereof can be isolated from a host cell, for example by secretion of the AfAmyl or variant from the host cell. A cultured cell material comprising AfAmyl or variant thereof can be obtained following secretion of the AfAmyl or variant from the host cell. The AfAmyl or variant optionally is purified prior to use. The AfAmyl gene can be cloned and expressed according to methods well known in the art. Suitable host cells include bacterial, plant, yeast cells, algal cells or fungal cells, e.g., filamentous fungal cells. Particularly useful host cells include *Aspergillus fumigatus* or *Trichoderma reesei* or other fungal hosts. Other host cells include bacterial cells, e.g., *Bacillus subtilis* or *B. licheniformis*, plant, algal and animal host cells.

The host cell further may express a nucleic acid encoding a homologous or heterologous glucoamylase, i.e., a glucoamylase that is not the same species as the host cell, or one or more other enzymes. The glucoamylase may be a variant glucoamylase, such as one of the glucoamylase variants disclosed in U.S. Pat. No. 8,058,033 (Danisco US Inc.), for example. Additionally, the host may express one or more accessory enzymes, proteins, and/or peptides. These may benefit pretreatment, liquefaction, saccharification, fermentation, SSF, stillage, etc processes. Furthermore, the host cell may produce biochemicals in addition to enzymes used to digest the various feedstock(s). Such host cells may be useful for fermentation or simultaneous saccharification and fermentation processes to reduce or eliminate the need to add enzymes.

The host cell further may express a nucleic acid encoding a homologous or heterologous isoamylase, i.e., an isoamylase that is not from the same species or genus as the host cell, or one or more other enzymes. The isoamylase may be a variant isoamylase or an isoamylase fragment, such as one of those disclosed in U.S. Pat. No. 5,352,602, for example. Additionally, the host may express one or more accessory enzymes, proteins, and/or peptides. These may benefit liquefaction, saccharification, fermentation, SSF, Stillage, etc processes. Furthermore, the host cell may produce biochemicals and/or enzymes used in the production of a biochemical in addition to enzymes used to digest the carbon feedstock(s). Such host cells may be useful for fermentation or simultaneous saccharification and fermentation processes to reduce or eliminate the need to add enzymes.

3.1. Vectors

A DNA construct comprising a nucleic acid encoding an AfAmyl or variant thereof can be constructed to be expressed in a host cell. Representative nucleic acids that encode AfAmyl include SEQ ID NO: 2 or 3. Because of the well-known degeneracy in the genetic code, variant polynucleotides that encode an identical amino acid sequence can be designed and made with routine skill. It is also well-known in the art to optimize codon use for a particular host cell. Nucleic acids encoding an AfAmyl or variant thereof can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding an AfAmyl or variant thereof can be transformed and replicated in a bacterial host cell as a means of propagating and amplifying the vector. The vector also may be transformed into an expression host, so that the encoding nucleic acids can be expressed as a functional AfAmyl or variant thereof. Host cells that serve as expression hosts can include filamentous fungi, for example. The Fungal Genetics Stock Center (FGSC) Catalogue of Strains lists suitable vectors for expression in fungal host cells. See FGSC, Catalogue of Strains, University of Missouri, at www.fgsc.net (last modified Jan. 17, 2007). A representative vector is plasmid pZZH352 (FIG. 2), which comprises a pTrex3 gM expression vector (U.S. Published Application No. 2011/0136197 A1). pZZH352 also allows expression of a nucleic acid encoding AfAmy1 under the control of the cbh1 promoter in a fungal host. pZZH352 can be modified with routine skill to comprise and express a nucleic acid encoding an AfAmy1 variant.

A nucleic acid encoding an AfAmy1 or a variant thereof can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding an AfAmy1 or variant thereof, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an AfAmy1 or variant thereof is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. The pZZH352 vector depicted in FIG. 2, for example, contains a cbh1 promoter operably linked to AfAmy1. cbh1 is an endogenous, inducible promoter from *T. reesei*. See Liu et al. (2008) "Improved heterologous gene expression in *Trichoderma reesei* by cellobiohydrolase I gene (cbh1) promoter optimization," *Acta Biochim. Biophys. Sin (Shanghai)* 40(2): 158-65.

The coding sequence can be operably linked to a signal sequence. The DNA encoding the signal sequence may be the DNA sequence naturally associated with the AfAmy1 gene to be expressed. For example, the DNA may encode the AfAmy1 signal sequence of SEQ ID NO: 4 operably linked to a nucleic acid encoding an AfAmy1 or a variant thereof. The DNA encodes a signal sequence from a species other than *A. fumigatus*. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding an AfAmy1 or variant thereof. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and sC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of an AfAmy1 or variant thereof for subsequent purification. Extracellular secretion of the AfAmy1 or variant thereof into the culture medium can also be used to make a cultured cell material comprising the isolated AfAmy1 or variant thereof.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the AfAmy1 or variant thereof to a host cell organelle such as a peroxisome, or to a particular host cell compartment. Such a targeting sequence includes but is not limited to serine-lysine-leucine (SKL), which is a known peroxisome target signal. For expression under the direction of control sequences, the nucleic acid sequence of the AfAmy1 or variant thereof is operably linked to the control sequences in proper manner with respect to expression.

The procedures used to ligate the DNA construct encoding an AfAmy1 or variant thereof, the promoter, terminator and other elements, respectively, and to insert them into suitable vectors containing the information necessary for replication, are well known to persons skilled in the art (see, e.g., Sambrook et al., MOLECULAR CLONING: A LABORATORY MANUAL, $2^{nd}$ ed., Cold Spring Harbor, 1989, and 3rd ed., 2001).

3.2. Transformation and Culture of Host Cells

An isolated cell, either comprising a DNA construct or an expression vector, is advantageously used as a host cell in the recombinant production of an AfAmy1 or variant thereof. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis*, *Bacillus licheniformis*, *Bacillus lentus*, *Bacillus brevis*, *Geobacillus* (formerly *Bacillus*) *stearother-*

*mophilus, Bacillus alkalophilus, Bacillus amyloliquefaciens, Bacillus coagulans, Bacillus lautus, Bacillus megaterium*, and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A suitable procedure for transformation of *Aspergillus* host cells includes, for example, that described in EP 238023. The AfAmyl or variant thereof expressed by a fungal host cell can be glycosylated, i.e., the AfAmyl or variant thereof will comprise a glycosyl moiety. The glycosylation pattern can be the same as present in the wild-type AfAmyl. Alternatively, the host organism can be an algal, bacterial, yeast or plant expression host.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding an AfAmyl or variant thereof is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2\times10^6$/mL. A volume of 100 of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

3.3. Expression

A method of producing an AfAmyl or variant thereof may comprise cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an AfAmyl or variant thereof. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of an α-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration and, in some cases, concentrating the clarified broth. Further processes may include precipitating proteinaceous components of the medium by means of a salt such as ammonium sulfate, followed by the use of chromatographic procedures such as ion exchange chromatography, affinity chromatography, or the like.

The polynucleotide encoding AfAmyl or a variant thereof in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of the AfAmyl or variant thereof. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired AfAmyl or variant thereof. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an AfAmyl or variant thereof.

3.4. Identification of AfAmyl Activity

To evaluate the expression of an AfAmyl or variant thereof in a host cell, assays can measure the expressed protein, corresponding mRNA, or α-amylase activity. For example, suitable assays include Northern blotting, reverse transcriptase polymerase chain reaction, and in situ hybridization, using an appropriately labeled hybridizing probe. Suitable assays also include measuring AfAmyl activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. α-Amylase activity also may be measured by any known method, such as the PAHBAH or ABTS assays, described below.

3.5. Methods for Purifying AfAmyl and Variants Thereof.

Fermentation, separation, and concentration techniques are well known in the art and conventional methods can be used in order to prepare a concentrated AfAmyl or variant α-amylase polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultrafiltration, extraction, or chromatography, or the like, are generally used.

It is desirable to concentrate an AfAmyl or variant α-amylase polypeptide-containing solution in order to optimize recovery. Use of unconcentrated solutions requires increased incubation time in order to collect the purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of purification include but are not limited to rotary vacuum filtration and/or ultrafiltration.

The enzyme solution is concentrated into a concentrated enzyme solution until the enzyme activity of the concentrated AfAmyl or variant α-amylase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate the AfAmyl or variant thereof. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific AfAmyl or variant α-amylase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, AfAmyl or variant α-amylase polypeptide concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further purification of the purified enzyme precipitate can be obtained by washing the precipitate with water. For example, the purified enzyme precipitate is washed with water containing the metal halide precipitation agent, or with water containing the metal halide and the organic compound precipitation agents.

During fermentation, an AfAmyl or variant α-amylase polypeptide accumulates in the culture broth. For the isolation and purification of the desired AfAmyl or variant α-amylase, the culture broth is centrifuged or filtered to eliminate cells, and the resulting cell-free liquid is used for enzyme purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further purification, a conventional procedure such as ion exchange chromatography may be used.

Purified enzymes are useful for laundry and cleaning applications. For example, they can be used in laundry detergents and spot removers. They can be made into a final product that is either liquid (solution, slurry) or solid (granular, powder).

A more specific example of purification, is described in Sumitani et al. (2000) "New type of starch-binding domain: the direct repeat motif in the C-terminal region of *Bacillus* sp. 195 α-amylase contributes to starch binding and raw starch degrading," *Biochem. J.* 350: 477-484, and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 min. and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$, and eluted at a linear flow rate of 7 mL/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, Pa.; Cat. No. 19812) was equilibrated with 20 mM Tris/HCl buffer (pH 7.0) containing 5 mM $CaCl_2$ and 1.5 M $(NH_4)_2SO_4$. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See Sumitani et al. (2000) *Biochem. J.* 350: 477-484, for general discussion of the method and variations thereon.

For production scale recovery, an AfAmyl or variant α-amylase polypeptide can be partially purified as generally described above by removing cells via flocculation with polymers. Alternatively, the enzyme can be purified by microfiltration followed by concentration by ultrafiltration using available membranes and equipment. However, for some applications, the enzyme does not need to be purified, and whole broth culture can be lysed and used without further treatment. The enzyme can then be processed, for example, into granules.

4. Compositions and Uses of AfAmyl and Variants Thereof

AfAmyl and its variants are useful for a variety of industrial applications. For example, AfAmyl and its variants are useful in a starch conversion process, particularly in a saccharification process of a starch that has undergone liquefaction. The desired end-product may be any product that may be produced by the enzymatic conversion of the starch substrate. The end product can be alcohol, or optionally ethanol. The end product also can be organic acids, amino acids, biofuels, and other biochemical, including, but not limited to, ethanol, citric acid, succinic acid, monosodium glutamate, gluconic acid, sodium gluconate, calcium gluconate, potassium gluconate, itaconic acid and other carboxylic acids, glucono delta-lactone, sodium erythorbate, lysine, omega 3 fatty acid, butanol, isoprene, 1,3-propanediol, and biodiesel. For example, the desired product may be a syrup rich in glucose and maltose, which can be used in other processes, such as the preparation of HFCS, or which can be converted into a number of other useful products, such as ascorbic acid intermediates (e.g., gluconate; 2-keto-L-gulonic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or for drinking (i.e., potable alcohol). One skilled in the art is aware of various fermentation conditions that may be used in the production of these end-products. AfAmyl and variants thereof also are useful in compositions and methods of food preparation. These various uses of AfAmyl and its variants are described in more detail below.

4.1. Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling or grinding. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling or grinding, whole kernels are ground into a fine powder and often processed without fractionating the grain into its component parts. In some cases, oils from the kernels are recovered. Dry ground grain thus will comprise significant amounts of non-starch carbohydrate compounds, in addition to starch. Dry grinding of the starch substrate can be used for production of ethanol and other biochemicals. The starch to be processed may be a highly refined starch quality, for example, at least 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-Amylase (EC 3.2.1.1) may be added to the slurry, with a metering pump, for example. The α-amylase typically used for this application is a thermally stable, bacterial α-amylase, such as a *Geobacillus stearothermophilus* α-amylase. The α-amylase is usually supplied, for example, at about 1500 units per kg dry matter of starch. To optimize α-amylase stability and activity, the pH of the slurry typically is adjusted to about pH 5.5-6.5 and about 1 mM of calcium (about 40 ppm free calcium ions) typically is added. *Geobacillus stearothermophilus* variants or other α-amylases may require different conditions. Bacterial α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylase may be pumped continuously through a jet cooker, which is steam heated to 105° C. Gelatinization occurs rapidly under these conditions, and the enzymatic activity, combined with the significant shear forces, begins the hydrolysis of the starch substrate. The residence time in the jet cooker is brief. The partly gelatinized starch may be passed into a series of holding tubes maintained at 105-110° C. and held for 5-8 min. to complete the gelatinization process ("primary liquefaction"). Hydrolysis to the required DE is completed in holding tanks at 85-95° C. or higher temperatures for about 1 to 2 hours ("secondary liquefaction"). These tanks may contain baffles to discourage back mixing. As used herein, the term "minutes of secondary liquefaction" refers to the time that has elapsed from the start of secondary liquefaction to the time that the Dextrose Equivalent (DE) is measured. The slurry is then allowed to cool to room temperature. This cooling step can be 30 minutes to 180 minutes, e.g. 90 minutes to 120 minutes.

The liquefied starch resulting from the process above typically contains about 98% oligosaccharides and about 2% maltose and 0.3% D-glucose. The liquefied starch typically is in the form of a slurry having a dry solids content (w/w) of about 10-50%; about 10-45%; about 15-40%; about 20-40%; about 25-40%; or about 25-35%.

AfAmyl and variants thereof can be used in a process of liquefaction instead of bacterial α-amylases. Liquefaction with AfAmyl and variants thereof advantageously can be conducted at low pH, eliminating the requirement to adjust the pH to about pH 5.5-6.5. AfAmyl and variants thereof can be used for liquefaction at a pH range of 2 to 7, e.g., pH 3.0-7.5, pH 4.0-6,0, or pH 4.5-5.8. AfAmyl and variants thereof can maintain liquefying activity at a temperature range of about 80° C.-95° C., e.g., 85° C., 90° C., or 95° C. For example, liquefaction can be conducted with 800 μg AfAmyl or a variant thereof in a solution of 25% DS corn starch for 10 min at pH 5.8 and 85° C., or pH 4.5 and 95° C., for example. Liquefying activity can be assayed using any of a number of known viscosity assays in the art.

4.3. Saccharification

The liquefied starch can be saccharified into a syrup rich in lower DP (e.g., DP1+DP2) saccharides, using the isoamylase and the AfAmyl or its variant thereof, optionally in the presence of another enzyme(s). The exact composition of the products of saccharification depends on the combination of enzymes used, as well as the type of granular starch processed. Advantageously, the syrup obtainable using the provided isoamylase and AfAmyl or its variant thereof may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%. AfAmyl or its variant in combination with an isoamylase also produces a relatively high yield of glucose, e.g., DP1>20%, in the syrup product.

Whereas liquefaction is generally run as a continuous process, saccharification is often conducted as a batch process. Saccharification typically is most effective at temperatures of about 60-65° C. and a pH of about 4.0-4.5, e.g., pH 4.3, necessitating cooling and adjusting the pH of the liquefied starch. Saccharification may be performed, for example, at a temperature between about 30° C., about 40° C., about 50° C., or about 55° C. to about 60° C. or about 65° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min., for example. Further incubation will result in a lower DE, eventually to about 90 DE, as accumulated glucose re-polymerizes to isomaltose and/or other reversion products via an enzymatic reversion reaction and/or with the approach of thermodynamic equilibrium. When using an AfAmyl polypeptide or variants thereof and an isoamylase, saccharification optimally is conducted at a temperature range of about 30° C. to about 65° C., e.g., 39° C.-56° C. or 45° C.-50° C. The saccharifying may be conducted over a pH range of about pH 3 to about pH 7, e.g., pH 3.0-pH 6.0, pH 3.0-5.5; pH 3.0-4.6; pH 3.5, or pH 3.8.

AfAmyl or a variant thereof and/or isoamylase also may be added to the slurry in the form of a composition. AfAmyl or a variant thereof can be added to a slurry of a granular starch substrate in an amount of about 0.6-10 ppm ds, e.g., 2 ppm ds. The AfAmyl or variant thereof can be added as a whole broth, clarified, partially purified, or purified enzyme. The specific activity of the purified AfAmyl or variant thereof may be about 300 U/mg of enzyme, for example, measured with the PAHBAH assay. AfAmyl or variant thereof also can be added as a whole broth product.

AfAmyl or a variant thereof and/or an isoamylase may be added to the slurry as an isolated enzyme solution. For example, AfAmyl or a variant thereof and/or an isoamylase can be added in the form of a cultured cell material produced by host cells expressing the AfAmyl or variant thereof and/or an isoamylase. AfAmyl or a variant thereof and/or an isoamylase also may be secreted by a host cell into the reaction medium during the fermentation or SSF process, such that the enzyme is provided continuously into the reaction. The host cell producing and secreting the AfAmyl or a variant may also express an additional enzyme, such as a glucoamylase and/or an isoamylase. For example, U.S. Pat. No. 5,422,267 discloses the use of a glucoamylase in yeast for production of alcoholic beverages. For example, a host cell, e.g., *Trichoderma reesei* or *Aspergillus niger*, may be engineered to co-express AfAmyl or a variant thereof and a glucoamylase or a variant glucoamylase, e.g., AnGA, an AnGA variant, HgGA, a HgGA variant, TrGA, or a TrGA variant, and/or an isoamylase and/or other enzymes during saccharification. The host cell can be genetically modified so as not to express its endogenous glucoamylase and/or isoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanse, a beta amylase, an isoamylase, and/or an isopullulanase, and/or other hydrolytic enzymes, and/or other enzymes of benefit in the process. See, e.g., WO 2011/153516 A2.

4.4. Isomerization

The soluble starch hydrolysate produced by treatment with AfAmyl or variants thereof and/or isoamylase can be converted into high fructose starch-based syrup (HFSS), such as high fructose corn syrup (HFCS). This conversion can be achieved using a glucose isomerase, particularly a glucose isomerase immobilized on a solid support. In some embodiments, the pH is increased to about 6.0 to about 8.0, e.g., pH 7.5, and $Ca^{2+}$ is removed by ion exchange. Suitable isomerases include Sweetzyme®, IT (Novozymes A/S); G-Zyme® IMGI, and G-Zyme® G993, Ketomax®, G-Zyme® G993, G-Zyme® G993 liquid, and GenSweet® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 28° C. to 65° C. EOF products include metabolites. The end product can be alcohol, or optionally ethanol. The end product also can be organic acids, amino acids, biofuels, and other biochemical, including, but not limited to, ethanol, citric acid, succinic acid, monosodium glutamate, gluconic acid, sodium gluconate, calcium gluconate, potassium gluconate, itaconic acid and other carboxylic acids, glucono delta-lactone, sodium erythorbate, lysine, omega 3 fatty acid, butanol, isoprene, 1,3-propanediol, and biodiesel.

Ethanologenic microorganisms include yeast, such as *Saccharomyces cerevisiae* and bacteria, e.g., *Zymomonas moblis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27(7): 1049-56. Commercial sources of yeast include ETHANOL RED® (LeSaffre); Thermosacc® (Lallemand); RED STAR® (Red Star); FERMIOL® (DSM Specialties); and SUPERSTART® (Alltech). Useful microorganisms may be butanologenic. Butanologenic microorganisms may include, for example, butanologenic *Clostridia*, such as *Clostridium acetobutylicum, Clostridium beijerinckii, Clostridium saccharobutylicum*, and *Clostridium saccharobutylacetonicum*. See, e.g., Ezeji et al. (2007) "Bioproduction of butanol from biomass: from genes to bioreactors," *Curr. Opin. Biotechnol.* 18(3): 220-27. Microorganisms that produce other metabolites, such as citric acid and lactic acid, by fermentation are also known in the art. See, e.g., Papagianni (2007) "Advances in citric acid fermentation by *Aspergillus niger*: biochemical aspects, membrane transport and modeling," *Biotechnol. Adv.* 25(3): 244-63; John et al. (2009) "Direct lactic acid fermentation: focus on simultaneous saccharification and lactic acid production," *Biotechnol. Adv.* 27(2): 145-52.

The saccharification and fermentation processes may be carried out as an SSF process. Fermentation may comprise subsequent purification and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells that express and secrete AfAmyl or its variants continuously throughout SSF. The fungal cells expressing AfAmyl or its variants also can be the fermenting microorganism, e.g., an ethanologenic microorganism. Ethanol production thus can be carried out using a fungal cell that expresses sufficient AfAmyl or its variants so that less or no enzyme has to be added exogenously. The fungal host cell can be from an appropriately engineered fungal strain. Fungal host cells that express and secrete other enzymes, in addition to AfAmyl or its variants, also can be used. Such cells may express glucoamylase and/or a pullulanase, hexokinase, xylanase, glucose isomerase, xylose isomerase, phosphatase, phytase, protease, β-amylase, α-amylase, protease, cellulase, hemicellulase, lipase, cutinase, trehalase, isoamylase, redox enzyme, esterase, transferase, pectinase, alpha-glucosidase, beta-glucosidase, lyase, or other hydrolases, another enzyme, or a combination thereof. See e.g., WO 2009/099783.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising AfAmyl or Variants Thereof

AfAmyl or variants thereof and/or an isoamylase may be combined with a glucoamylase (EC 3.2.1.3), e.g., a *Trichoderma* glucoamylase or variant thereof. An exemplary glucoamylase is *Trichoderma reesei* glucoamylase (TrGA) and variants thereof that possess superior specific activity and thermal stability. See U.S. Published Applications Nos. 2006/0094080, 2007/0004018, and 2007/0015266 (Danisco US Inc.). Suitable variants of TrGA include those with glucoamylase activity and at least 80%, at least 90%, or at least 95% sequence identity to wild-type TrGA. AfAmyl and its variants advantageously increase the yield of glucose produced in a saccharification process catalyzed by TrGA.

Alternatively, the glucoamylase may be another glucoamylase derived from plants, fungi, algae, or bacteria. For example, the glucoamylases may be *Aspergillus niger* G1 or G2 glucoamylase or its variants (e.g., Boel et al. (1984) *EMBO J.* 3: 1097-1102; WO 92/00381; WO 00/04136 (Novo Nordisk A/S)); and *A. awamori* glucoamylase (e.g., WO 84/02921 (Cetus Corp.)). Other contemplated *Aspergillus* glucoamylase include variants with enhanced thermal stability, e.g., G137A and G139A (Chen et al. (1996) *Prot. Eng.* 9: 499-505); D257E and D293E/Q (Chen et al. (1995) *Prot. Eng.* 8: 575-582); N182 (Chen et al. (1994) *Biochem. J.* 301: 275-281); A246C (Fierobe et al. (1996) *Biochemistry,* 35: 8698-8704); and variants with Pro residues in positions A435 and S436 (Li et al. (1997) *Protein Eng.* 10: 1199-1204). Other contemplated glucoamylases include *Talaromyces* glucoamylases, in particular derived from *T. emersonii* (e.g., WO 99/28448 (Novo Nordisk A/S), *T. leycettanus* (e.g., U.S. Pat. No. RE 32,153 (CPC International, Inc.)), *T. duponti*, or *T. thermophilus* (e.g., U.S. Pat. No. 4,587,215). Contemplated bacterial glucoamylases include glucoamylases from the genus *Clostridium*, in particular *C. thermoamylolyticum* (e.g., EP 135,138 (CPC International, Inc.) and *C. thermohydrosulfuricum* (e.g., WO 86/01831 (Michigan Biotechnology Institute)). Suitable glucoamylases include the glucoamylases derived from *Aspergillus oryzae*, such as a glucoamylase shown in SEQ ID NO:2 in WO 00/04136 (Novo Nordisk A/S). Also suitable are commercial glucoamylases, such as AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR (*A. niger* glucoamylase with a low protease content). Still other suitable glucoamylases include *Aspergillus fumigatus* glucoamylase, *Talaromyces* glucoamylase, *Thielavia* glucoamylase, *Trametes* glucoamylase, *Thermomyces* glucoamylase, *Athelia* glucoamylase, or *Humicola* glucoamylase (e.g., HgGA). Glucoamylases typically are added in an amount of about 0.1-2 glucoamylase units (GAU)/g ds, e.g., about 0.16 GAU/g ds, 0.23 GAU/g ds, or 0.33 GAU/g ds.

In particular, glucoamylases as contemplated herein may be used for starch conversion processes, and particularly in the production of dextrose for fructose syrups, specialty sugars and in alcohol and other end products (e.g., organic acids, amino acids, biofuels, and other biochemical) production from fermentation of starch containing substrates (e.g., G. M. A. van Beynum et al., Eds. (1985) STARCH CONVERSION TECHNOLOGY, Marcel Dekker Inc. NY; see also U.S. Pat. No. 8,178,326). The contemplated glucoamylase variant may also work synergistically with plant enzymes that are endogenously produced or genetically engineered. Additionally, the contemplated glucoamylase variant can work synergistically with endogenous, engineered, secreted, or non-secreted enzymes from a host producing the desired end product (e.g., organic acids, amino acids, biofuels, and other biochemicals, including, but not limited to, ethanol, citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine, omega 3 fatty acid, butanol, isoprene, 1,3-propanediol, and biodiesel). Furthermore, the host cells expressing the contemplated glucoamylase variant may produce biochemicals in addition to enzymes used to digest the various feedstock(s). Such host cells may be useful for fermentation or simultaneous saccharification and fermentation processes to reduce or eliminate the need to add enzymes.

Other suitable enzymes that can be used with AfAmyl or its variants include another glucoamylase, hexokinase, xylanase, glucose isomerase, xylose isomerase, phosphatase, phytase, protease, pullulanase, β-amylase, α-amylase, protease, cellulase, hemicellulase, lipase, cutinase, trehalase, isoamylase, redox enzyme, esterase, transferase, pectinase, alpha-glucosidase, beta-glucosidase, lyase, or other hydrolases, or a combination thereof. See e.g., WO 2009/099783. For example, a debranching enzyme, such as an isoamylase (E.C. 3.2.1.68), may be added in effective amounts well known to the person skilled in the art. A pullulanase (E.C. 3.2.1.41), e.g., Promozyme®, is also suitable. Pullulanase typically is added at 100 U/kg ds. Further suitable enzymes include proteases, such as fungal, yeast and bacterial proteases, plant proteases and algal proteases. Fungal proteases include those obtained from *Aspergillus*, such as *A. niger, A. awamori, A. oryzae; Mucor* (e.g., *M. miehei*); *Rhizopus*; and *Trichoderma.*

β-Amylases (EC 3.2.1.2) are exo-acting maltogenic amylases, which catalyze the hydrolysis of 1,4-α-glucosidic linkages into amylopectin and related glucose polymers, thereby releasing maltose. β-Amylases have been isolated from various plants and microorganisms. See Fogarty et al. (1979) in PROGRESS IN INDUSTRIAL MICROBIOLOGY, Vol. 15, pp. 112-115. These β-Amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Danisco US Inc.); and Novozym™ WBA (Novozymes A/S).

5. Compositions and Methods for Baking and Food Preparation

The present invention also relates to a "food composition," including but not limited to a food product, animal feed and/or food/feed additives, comprising an AfAmyl or variant thereof with an isoamylase, and methods for preparing such a food composition comprising mixing AfAmyl or variant thereof with an isoamylase with one or more food ingredients, or uses thereof Furthermore, the present invention relates to the use of an AfAmyl or variant thereof with an isoamylase in the preparation of a food composition, wherein the food composition is baked subsequent to the addition of the polypeptide of the invention. As used herein the term "baking composition" means any composition and/or additive prepared in the process of providing a baked food product, including but not limited to bakers flour, a dough, a baking additive and/or a baked product. The food composition or additive may be liquid or solid.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, an AfAmyl or variant thereof, by itself or in combination with another α-amylase(s), may be added to the flour to augment the level of endogenous α-amylase activity in flour.

An AfAmyl or variant thereof with an isoamylase further can be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with an AfAmyl or variant thereof include an endo-amylase, e.g., a bacterial endo-amylase from *Bacillus*. The additional amylase can be another maltogenic α-amylase (EC 3.2.1.133), e.g., from *Bacillus*. Novamyl® is an exemplary maltogenic α-amylase from *B. stearothermophilus* strain NCIB 11837 and is described in Christophersen et al. (1997) *Starch* 50: 39-45. Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soy bean, or from microbial sources, such as *Bacillus.*

The baking composition comprising an AfAmyl or variant thereof with an isoamylase further can comprise a phospholipase or enzyme with phospholipase activity. An enzyme with phospholipase activity has an activity that can be measured in Lipase Units (LU). The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, for example.

The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 LU/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae.*

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

The dough product may be any processed dough product, including fried, deep fried, roasted, baked, steamed and boiled doughs, such as steamed bread and rice cakes. In one embodiment, the food product is a bakery product. Typical bakery (baked) products include bread—such as loaves, rolls, buns, bagels, pizza bases etc. pastry, pretzels, tortillas, cakes, cookies, biscuits, crackers etc.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*. Mammalian or plant derived xylanase is also envisioned. Xylanases include Pentopan® and Novozym 384®, for example, which are commercially available xylanase preparations produced from *Trichoderma reesei*. The amyloglucosidase may be an *A. niger* amyloglucosidase (such as AMG®). Other useful amylase products include Grindamyl® A 1000 or A 5000 (Grindsted Products, Denmark) and Amylase® H or Amylase® P (DSM). The glucose oxidase may be a fungal glucose oxidase, in particular an *Aspergillus niger* glucose oxidase (such as Gluzyme®). An exemplary protease is Neutrase®.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

The AfAmyl or variant thereof with an isoamylase may be used in a pre-mix, comprising flour together with an anti-staling amylase, a phospholipase, and/or a phospholipid. The pre-mix may contain other dough-improving and/or bread-improving additives, e.g., any of the additives, including enzymes, mentioned above. The AfAmyl or variant thereof can be a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying the AfAmyl or variant thereof onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Enveloped particles, i.e., α-amylase particles, can comprise an AfAmyl or variants thereof. To prepare enveloped α-amylase particles, the enzyme is contacted with a food grade lipid in sufficient quantity to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated α-amylase particles, where substantially all of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

In a further aspect of the invention, the food composition is an oil, meat, lard, composition comprising an AfAmyl or a variant thereof with an isoamylase. In this context the term "[oil/meat/lard] composition" means any composition, based on, made from and/or containing oil, meat or lard, respectively. Another aspect the invention relates to a method of preparing an oil or meat or lard composition and/or additive comprising an AfAmyl or a variant thereof with an isoamylase, comprising mixing the polypeptide of the invention with a oil/meat/lard composition and/or additive ingredients.

In a further aspect of the invention, the food composition is an animal feed composition, animal feed additive and/or pet food comprising an AfAmyl and variants thereof with an isoamylase. The present invention further relates to a method for preparing such an animal feed composition, animal feed additive composition and/or pet food comprising mixing an AfAmyl and variants thereof with an isoamylase with one or more animal feed ingredients and/or animal feed additive ingredients and/or pet food ingredients. Furthermore, the present invention relates to the use of an AfAmyl and variants thereof with an isoamylase in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

6. Textile Desizing Compositions and Use

Also contemplated are compositions and methods of treating fabrics (e.g., to desize a textile) using an AfAmyl or a variant thereof with an isoamylase. Fabric-treating methods are well known in the art (see, e.g., U.S. Pat. No. 6,077,316). For example, the feel and appearance of a fabric can be improved by a method comprising contacting the fabric with an AfAmyl or a variant thereof with an isoamylase in a solution. The fabric can be treated with the solution under pressure.

An AfAmyl or a variant thereof with an isoamylase can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An AfAmyl or a variant thereof with an isoamylase can be applied during or after the weaving to remove these sizing starch or starch derivatives. After weaving, an AfAmyl or a variant thereof with an isoamylase can be used to remove the size coating before further processing the fabric to ensure a homogeneous and wash-proof result.

An AfAmyl or a variant thereof with an isoamylase can be used alone or with other desizing chemical reagents and/or desizing enzymes to desize fabrics, including cotton-containing fabrics, as detergent additives, e.g., in aqueous compositions. An AfAmyl or a variant thereof with an isoamylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An AfAmyl or a variant thereof with an isoamylase can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an AfAmyl or variant thereof with an isoamylase as a component. An amylase polypeptide with an isoamylase can be used as a component in detergent compositions for hand washing, laundry washing, dishwashing, and other hard-surface cleaning.

7.1. Overview

Preferably, the AfAmyl or variant thereof with an isoamylase is incorporated into detergents at or near a concentration conventionally used for amylase in detergents. For example, an amylase polypeptide may be added in amount corresponding to 0.00001-1 mg (calculated as pure enzyme protein) of amylase per liter of wash/dishwash liquor. Exemplary formulations are provided herein, as exemplified by the following:

An amylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions for inclusion of the present α-amylase are described, below.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and copolymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydroxyethyl cellulose, cationic starch, cationic polyacrylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally include silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethyl hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

7.4. Automatic Dishwashing (ADW) Detergent Composition

Exemplary ADW detergent composition includes nonionic surfactants, including ethoxylated non-ionic surfactants, alcohol alkoxylated surfactants, epoxy-capped poly (oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-polyphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7$/$C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7$/$C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," *Nature* 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases:

Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, KANNASE™, and BLAZE™ (Novo Nordisk A/S and Novozymes A/S); MAXATASE®, MAXACAL™ MAXAPEM™, PROPERASE®, PURAFECT®, PURAFECT OXP™ FN2™, and FN3™ (Danisco US Inc.). Other exemplary proteases include NprE from *Bacillus amyloliquifaciens* and ASP from *Cellulomonas* sp. strain 69B4.

Lipases:

Suitable lipases include those of bacterial, fungal, plant, or animal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens, Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta,* 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S and Novozymes A/S).

Polyesterases:

Suitable polyesterases can be included in the composition, such as those described in, for example, WO 01/34899, WO 01/14629, and U.S. Pat. No. 6,933,140.

Amylases: The compositions can be combined with other amylases, such as non-production enhanced amylase. These can include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, and PURASTAR® (from Danisco US Inc.).

Cellulases:

Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S and Novozymes A/S); CLAZINASE® and PURADAX HA® (Danisco US Inc.); and KAC-500(B)™ (Kao Corporation).

Peroxidases/Oxidases:

Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Although the present compositions and methods have been described with reference to the details below, it would be understood that various modifications can be made.

7.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

8. Brewing Compositions

An AfAmyl or variant thereof with an isoamylase may be a component of a brewing composition used in a process of providing a fermented beverage, such as brewing. It is believed that non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces (about 340 grams) of beer. The AfAmyl or variant thereof with an isoamylase, usually in combination with a glucoamylase and optionally a pullulanase, assist in converting the starch into dextrins and fermentable sugars, lowering the residual non-fermentable carbohydrates in the final beer.

The principal raw materials used in making these beverages are water, hops and malt. In addition, but also exclusively, adjuncts such as common corn grits, refined corn grits, brewer's milled yeast, rice, sorghum, refined corn starch, barley, barley starch, dehusked barley, wheat, wheat starch, torrified cereal, cereal flakes, lye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has an important effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops can act as protein precipitants, establish preservative agents and aid in foam formation and stabilization.

Cereals (grains), such as barley, oats, wheat, but also corn and rice, are often used for brewing, both in industry and for home brewing, but also other plant components, such as hops are often added. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. An AfAmyl or variant thereof, by itself or in combination with another α-amylase(s), accordingly may be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer. Typically, milled or crushed malt, malt and adjunct, or adjunct is mixed with water and held for a period of time under controlled temperatures to permit the enzymes present in the malt and/or adjunct to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilizes the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast that may flocculate is removed. Finally, the beer is cooled and stored for a period of time, during which the beer clarifies and its flavor develops, and any material that might impair the appearance, flavor and shelf life of the beer settles out. The beer usually contains from about 2% to about 10% v/v alcohol, although beer with a higher alcohol content, e.g., 18% v/v, may be obtained. Prior to packaging, the beer is carbonated and, optionally, filtered and pasteurized.

The brewing composition comprising the AfAmyl or variant thereof with an isoamylase, often but not necessarily in combination with one or more exogenous enzymes, such as glucoamylase(s), pullulanase(s), and any combination thereof, may be added to the mash of step (a) above, such as during the preparation of the mash. Alternatively, or in addition, the brewing composition may be added to the mash of step (b) above, such as during the filtration of the mash. Alternatively, or in addition, the brewing composition may be added to the wort of step (c) above, such as during the fermenting of the wort.

One aspect of the invention relates to the use of the AfAmyl or variant thereof with an isoamylase according to the invention in the production of a fermented beverage, such as a beer.

Another aspect concerns a method of providing a fermented beverage comprising the step of contacting a mash and/or a wort with the AfAmyl or variant thereof and an isoamylase.

A further aspect relates to a method or providing a fermented beverage comprising the steps of: (a) preparing a mash, (b) filtering the mash to obtain a wort, and (c) fermenting the wort to obtain a fermented beverage, such as a beer, wherein the AfAmyl or variant thereof and an isoamylase are added to: (i) the mash of step (a) and/or (ii) the wort of step (b) and/or (iii) the wort of step (c).

According to yet another aspect, a fermented beverage, such as a beer, is produced or provided by a method comprising the step(s) of (1) contact a mash and/or a wort with the AfAmyl or variant thereof and an isoamylase; and/or (2) (a) preparing a mash, (b) filtering the mash to obtain a wort, and (c) fermenting the wort to obtain a fermented beverage, such as a beer, wherein the AfAmyl or variant thereof and an isoamylase are added to: (i) the mash of step (a) and/or (ii) the wort of step (b) and/or (iii) the wort of step (c).

Particular embodiments pertain to any of the above use, method, or fermented beverage, wherein said fermented beverage is a beer, such as full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavoured malt beverages, e.g., citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like.

9. Reduction of Iodine-Positive Starch

AfAmyl and variants thereof with an isoamylase may reduce the iodine-positive starch (IPS), when used in a method of liquefaction and/or saccharification. One source of IPS is from amylose that escapes hydrolysis and/or from retrograded starch polymer. Starch retrogradation occurs spontaneously in a starch paste, or gel on ageing, because of the tendency of starch molecules to bind to one another followed by an increase in crystallinity. Solutions of low concentration become increasingly cloudy due to the progressive association of starch molecules into larger articles. Spontaneous precipitation takes place and the precipitated starch appears to be reverting to its original condition of cold-water insolubility. Pastes of higher concentration on cooling set to a gel, which on ageing becomes steadily firmer due to the increasing association of the starch molecules. This arises because of the strong tendency for hydrogen bond formation between hydroxy groups on adjacent starch molecules. See J. A. Radley, ed., STARCH AND ITS DERIVATIVES 194-201 (Chapman and Hall, London (1968)).

The presence of IPS in saccharide liquor negatively affects final product quality and represents a major issue with downstream processing. IPS plugs or slows filtration system, and fouls the carbon columns used for purification, and the evaporators. When IPS reaches sufficiently high levels, it may leak through the carbon columns and decrease production efficiency. Additionally, it may results in hazy final product upon storage, which is unacceptable for final product quality. The amount of IPS can be reduced by isolating the saccharification tank and blending the contents back. IPS nevertheless will accumulate in carbon columns and filter systems, among other things. The use of AfAmyl or variants thereof and an isoamylase thus is expected to improve overall process performance by reducing the amount of IPS.

EXAMPLES

Example 1: Cloning of AfAmyl

The genome of *Aspergillus fumigatus* is sequenced. See *Aspergillus* 12-way comparative database asp2_v5, on the Internet at hypertext transfer protocol://aspgd.broadinstitute.org/cgi-bin/asp2_v3/shared/show_organism.cgi?site=asp2_v5&id=11 (downloaded Feb. 23, 2009). *A. fumigatus* encodes a glycosyl hydrolase with homology to other fungal alpha-amylase as determined from a BLAST search. See FIG. 1. The nucleotide sequence of the AfAmyl gene, which comprises eight introns, is set forth in SEQ ID NO: 2. A cDNA sequence obtained from the mRNA encoding AfAmyl, lacking the eight intron sequences, is set forth in SEQ ID NO: 3.

The AfAmyl gene was amplified from genomic DNA of *Aspergillus fumitatus* using the following primers: Primer 1 (Not I) 5'-ccgcggccgcaccATGAAGTGGATCGCGCAGCT-3' (SEQ ID NO: 12), and Primer 2 (Asc I) 5'-ccggcgcgccct-taTCATCTCCACGTATCAGACAC-3' (SEQ ID NO: 13). After digestion with Not I and Asc I, the PCR product was cloned into pTrex3 gM expression vector (described in U.S. Published Application 2011/0136197 A1) digested with the same restriction enzymes, and the resulting plasmid was labeled pZZH352. A plasmid map of pZZH352(3 gM-AfAmyl) is provided in FIG. 2. The sequence of the AfAmyl gene was confirmed by DNA sequencing.

Example 2: Expression and Purification of AfAmyl

The plasmid pZZH352(3 gM-AfAmyl) was transformed into a quad-deleted *Trichoderma reesei* strain (described in WO 05/001036) using biolistic method (Te'o et al., *J. Microbiol. Methods* 51:393-99, 2002). The expressed AfAmyl protein was secreted into the extracellular medium, and the filtered culture medium was used to perform SDS-PAGE and an alpha-amylase activity assay to confirm the enzyme expression.

The AfAmyl protein was purified via the beta-cyclodextrin (bCD) coupled Sepharose 6B chromatography, taking advantage of its CBM20 domain. About 300 ml AfAmyl-containing broth from the 7 L fermentor was adjusted to pH 4.3 and loaded onto 30 ml bCD-Sepharose column pre-equilibrated with 25 mM Na-acetate, pH 4.3 (buffer A). After sample loading, the column was washed with the same buffer for 3 CVs. The target protein was eluted with 0-100% gradient of buffer A with 10 mM alpha-cyclodextrin (buffer B) in 2 CVs. Fractions were analyzed by SDS-PAGE gel and assayed for AA activity. The fractions containing target protein were pooled and concentrated. The sample was then loaded onto a Superdex 75 XK26X60 column in 20 mM Na-phosphate pH 7 buffer with 0.15 M NaCl. The fractions containing target protein were again pooled. The sample was above 95% pure and concentrated using 10K Amicon Ultra-15 devices for storage in 40% glycerol at −80° C. until usage.

Example 3: Determining AfAmyl α-Amylase Activity

α-Amylase activity was assayed based on its release of reducing sugar from potato amylopectin substrate. Formation of reducing sugars was monitored colorimetrically via a PAHBAH assay. Activity number is reported as equivalents of glucose released per minute.

The 2.5% potato amylopectin (AP, Fluka Cat. No. 10118) substrate was prepared with 1.25 g ds in total of 50 g water/0.005% Tween followed by heating for 1 min with a microwave in 15 s intervals and stirring. A buffer cocktail was prepared by mixing 5 mL of 0.5 M Na acetate, pH 5.8; 2.5 mL 1 M NaCl; 0.2 mL 0.5 M $CaCl_2$; and 7.3 mL water/Tween (167 mM Na acetate, 167 mM NaCl, 6.67 mM $CaCl_2$).

Purified enzyme was diluted to 0.4 mg/mL (400 ppm) in water/Tween as stock solution. On the first row of a non-binding microtiter plate (Corning 3641), 195 μL of water was added, and 100 μL water/Tween was placed in all the remaining wells. 5 μL of 400 ppm enzyme was added to the first row so that the enzyme concentration is 10 ppm in the well and the final enzyme concentration in the reaction is 2 ppm. A two-fold serial dilution was carried out (40 μL+40 μL), through the seventh well, leaving the eighth well as an enzyme-free blank. 15 μL of the buffer cocktail, followed by 25 μL of amylopectin, was dispensed to a PCR plate using an automatic pipette. Reactions were initiated by dispensing 10 μL of the enzyme dilution series to the PCR plate, mixing quickly with a vortexer, and incubating for 10 minutes on a PCR heat block at 50° C. with a heated lid (80° C.). After exactly 10 minutes, 20 μL of 0.5 N NaOH was added to the plate followed by vortexing to terminate the reaction.

Total reducing sugars present in tubes were assayed via a PAHBAH method: 80 μL of 0.5 N NaOH was aliquoted to a PCR microtube plate followed by 20 μL of PAHBAH reagent (5% w/v 4-hydroxybenzoic acid hydrazide in 0.5 N HCl). 10 μL of terminated reactions were added to each row using a multichannel pipette and mixed briefly with up and down pipetting. The loaded plate was incubated at 95° C. for 2 min sealed with tin foil. 80 μL of developed reactions were transferred to a polystyrene microtiter plate (Costar 9017), and the OD was determined at 410 nm. The resulting OD values were plotted against enzyme concentration using Microsoft Excel. Linear regression was used to determine the slope of the linear part of the plot. Amylase activity was quantified using Equation 1:

$$\text{Specific Activity (Unit/mg)}=\text{Slope (enzyme)/slope (std)}\times 100 \quad (1),$$

where 1 Unit=1 μmol glucose eq./min.

A representative specific activity of AfAmyl and the benchmark amylase AkAA are shown in Table 1.

TABLE 1

Specific activity of purified alpha-amylases on amylopectin.

| Protein | Specific Activity (U/mg) |
|---|---|
| AkAA | 58.9 |
| AfAmyl | 291.1 |

Example 4: Effect of pH on AfAmyl α-Amylase Activity

The effect of pH on AfAmyl amylase activity was monitored using the alpha-amylase assay protocol as described in Example 3 in a pH range of 3.0 to 10.0. Buffer stocks were prepared as 1 M sodium acetate buffer stocks with pH 3.0 to 6.0, 1 M HEPES buffer stocks with pH 6.0 to pH 9.0, and 1 M CAPS buffer stock pH 10.0. The working buffer contains 2.5 mL of 1 M Na acetate (pH 3-6.5) or 1 M HEPES (pH 7-9), every half pH units, with 2.5 mL of 1 M NaCl and 50 μL of 2 M $CaCl_2$, 10 mL water/Tween (167 mM each buffer and NaCl, 6.67 mM $CaCl_2$), so that the final enzyme reaction mixture contains 50 mM each buffer and NaCl, 2 mM $CaCl_2$.

Figure 3A:
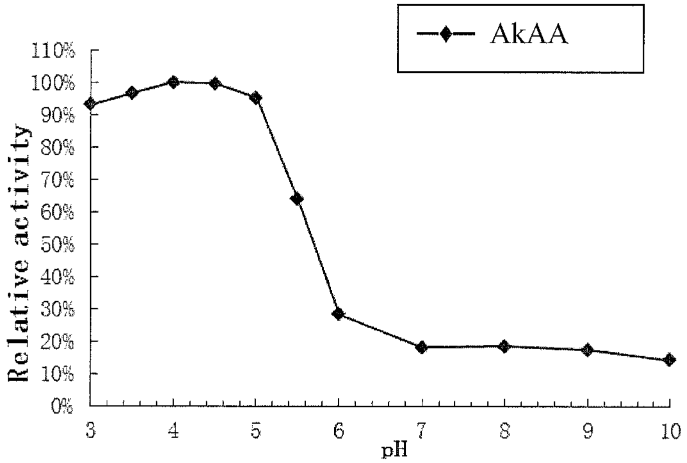
FIG. 3A depicts the dependence of α-amylase activity (relative units) of *Aspergillus kawachii* α-amylase (AkAA) on pH.
Figure 3B:
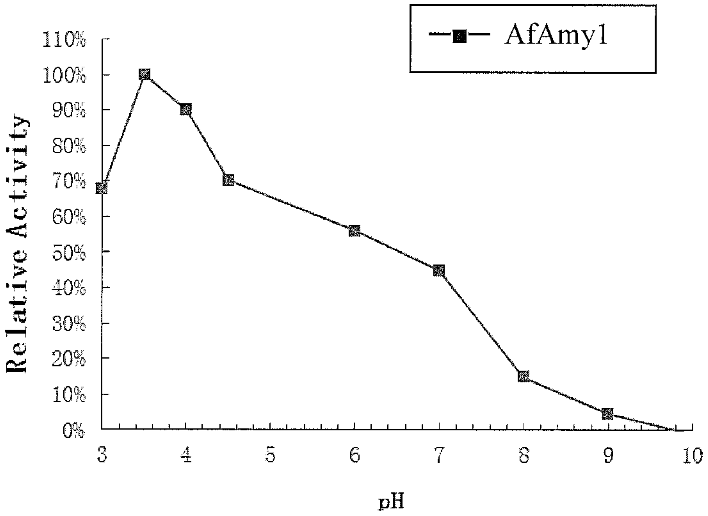
FIG. 3B depicts the dependence of α-amylase activity (relative units) of AfAmyl on pH. α-Amylase activity was based on 2 ppm enzyme and assayed by the release of reducing sugar from potato amylopectin substrate at 50° C.

Enzyme stocks were prepared in water/0.005% Tween at concentrations in the linear range of the PAHBAH assay. 15 μL of the working buffer (pH 3.5-7.0 using sodium acetate, pH 6.0-9.0 using HEPES), followed by 25 μL of amylopectin, was dispensed to a PCR plate using an automatic pipette. Sodium acetate and HEPES buffers were separately used at pH values of 6.0, 6.5, and 7.0 to confirm there are no buffer effects on enzyme activity. Reactions were initiated by dispensing 10 μL of enzyme stock to the PCR plate, mixing quickly on a vortexer, and incubating for 10 minutes on a PCR heat block at 50° C. with a heated lid (80° C.). Reactions were performed in replicates of three. Blank samples using the different pH buffers alone were included. After exactly 10 min, 20 μL of 0.5 N NaOH was added to the plate, followed by vortexing to terminate the reaction. Total reducing sugars present in wells were assayed with the PAHBAH method described above. The resulting OD values were converted to a percentage of relative activity by defining the optimum pH as 100% activity. The percent relative activity, plotted as a function of pH, is shown in FIG. 3A (benchmark AkAA) and FIG. 3B (AfAmyl). The optimum pH and pH range at >70% of maximum activity when hydrolysis is measured at 50° C. are listed in Table 2.

TABLE 2

Optimum pH and pH range (>70% activity) at 50° C. for purified alpha-amylases.

| Protein | Optimum pH | pH range (>70% activity) | pH range (≥85% activity) |
|---|---|---|---|
| AkAA | 4.0 | pH 3.0-5.4 | pH 3.0-5.0 |
| AfAmy1 | 3.5 | pH 3.0-4.6 | pH 3.2-4.0 |

Example 5: Effect of Temperature on AfAmyl α-Amylase Activity

The fungal alpha-amylase activity was monitored using the alpha-amylase assay protocol as described in Example 4 in a temperature range of 30° C. to 95° C. Buffer stock of the optimum pH of each enzyme is prepared as 2.5 mL of 1 M buffer (sodium acetate or HEPES, depending on the enzyme's optimum pH), 2.5 mL of 1 M NaCl and 50 μL of 2 M $CaCl_2$, 10 mL water/Tween (167 mM ea. buffer and NaCl, 6.67 mM $CaCl_2$), so that the final reaction mixture contained 50 mM each buffer and NaCl, 2 mM $CaCl_2$.

Figure 4A:
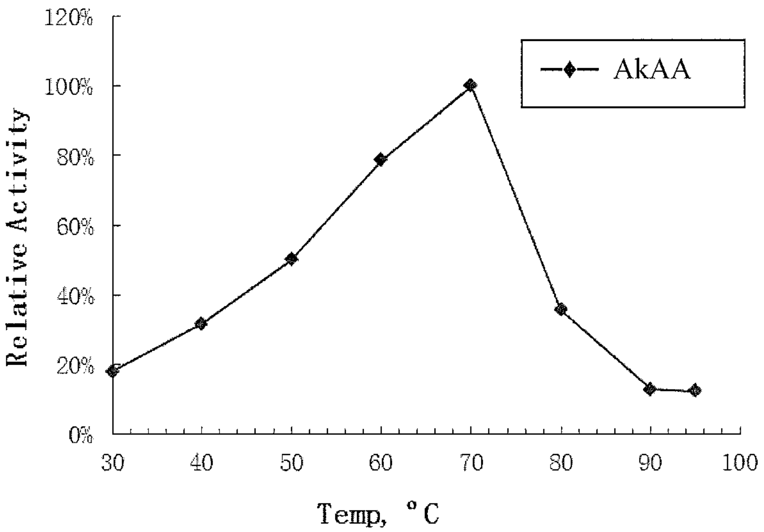
FIG. 4A depicts the dependence of α-amylase activity (relative units) of AkAA on temperature.
Figure 4B:
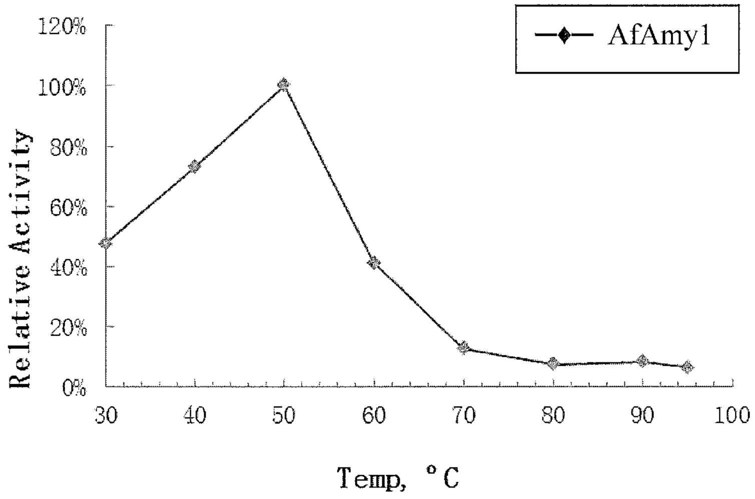
FIG. 4B depicts the dependence of α-amylase activity (relative units) of AfAmyl on temperature. α-Amylase activity was based on 2 ppm enzyme and assayed by the release of reducing sugar from potato amylopectin substrate at pH 4.0 (AkAA) or pH 3.5 (AfAmyl).

Enzyme stocks were prepared as described above. 15 μL of the buffer stock (optimum pH, predetermined), followed by 25 μL of the amylopectin, were dispensed to a PCR plate using an automatic pipette. Reactions were initiated by dispensing 10 μL of enzyme to the PCR plate, mixing quickly on a vortexer, and incubating for 10 minutes on a PCR heat block, at 30-95° C. (every 5-10° C.) with the lid heated to the same or greater than the incubation temperature. Reactions were performed in replicates of three. Blank samples using the different buffers alone were included. After exactly 10 min, 20 μL of 0.5 N NaOH were added to the plate followed by vortexing to terminate the reactions. Total reducing sugars present in tubes were assayed with a PAHBAH method as described above. The resulting OD values were converted to a percentage of relative activity by defining the optimum temperature as 100% activity. The temperature profiles of the fungal alpha-amylases are shown in FIG. 4A (AkAA benchmark) and FIG. 4B (AfAmyl). The optimum temperature and temperature range at >70% of maximum activity are listed in Table 3, when measured at the indicated optimal pH of the enzyme.

TABLE 3

Optimum temperature and temperature range (>70% activity) for alpha-amylases at their respective optimum pH.

| Protein | Optimum Temperature | Temp range (>70% activity) |
|---|---|---|
| AkAA, pH 4.0 | 70° C. | 56-75° C. |
| AfAmy1, pH 3.5 | 50° C. | 39-56° C. |

Example 6: Effect of Sustained Low pH on AfAmyl α-Amylase Activity

SSF is usually conducted at pH 3.5-5.5, 32° C. for 55 hours, and the enzymes used in the process should be able to maintain their activity during the whole process. Thus, it is useful to know the low pH stability of the α-amylases. The following protocol is used for testing the pH stability.

Figure 5A:
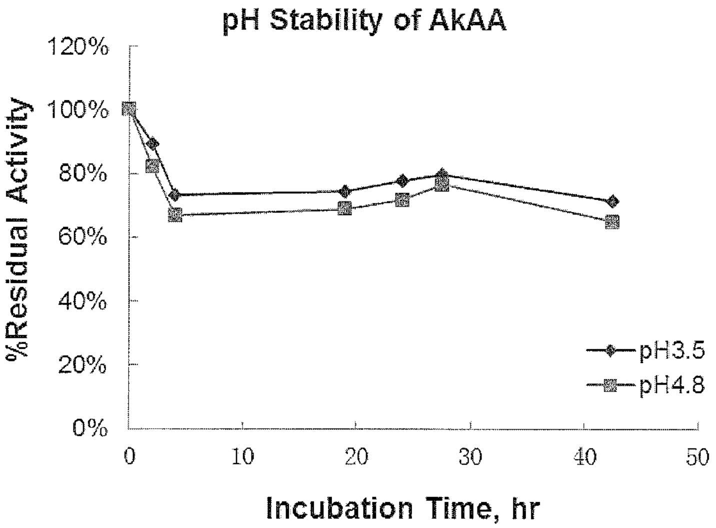
FIG. 5A depicts the residual α-amylase activity (relative units) of AkAA after incubation at pH 3.5 or 4.8 for the time periods shown.
Figure 5B:
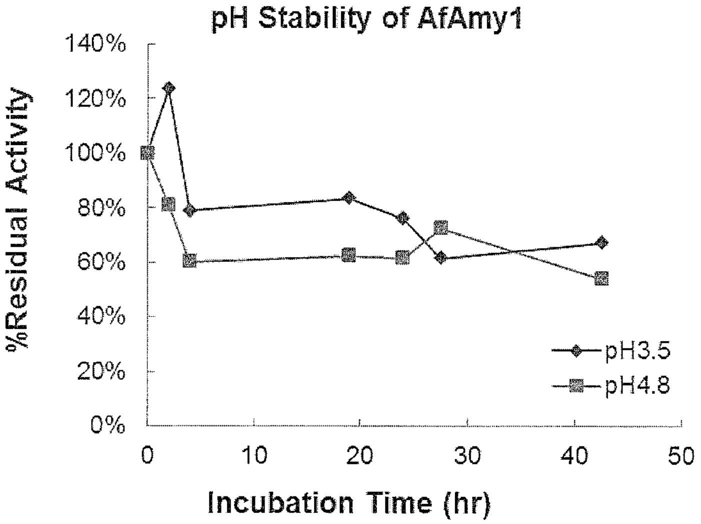
FIG. 5B depicts the residual α-amylase activity (relative units) of AfAmyl at pH 3.5 or 4.8 for the time periods shown. α-Amylase activity was based on 2 ppm enzyme and assayed by the release of reducing sugar from potato amylopectin substrate.

The enzymes were diluted in 50 mM sodium acetate at pH 3.5 and 4.8 to a concentration in the linear range of the α-amylase assay described above. The diluted enzymes were incubated at room temperature, sampling 10 μL for assays at t=0, 2, 4, 19, 24, 28, and 43 hr. Assays were conducted under standard conditions using amylopectin as a substrate and PAHBAH for the reducing sugar at pH 5, 50° C., as described above. Data were processed by normalizing signal to the glucose standard and plotted as the percentage of residual activity relative to t=0 as a function of time. FIG. 5A and FIG. 5B show the residual activity of the benchmark AkAA and AfAmyl, respectively, after incubation at pH 3.5 or 4.8 for different time periods. Both AkAA and AfAmyl maintain>60% activity after extended incubation at pH 3.5. Additionally, AfAmyl and AkAA behave similarly at pH 4.8. In contrast, amylases of bacteria origin usually lost most of their activity in several hours under these conditions (data not shown).

Example 7: AfAmyl Product Profile Analysis

To assay the products of fungal α-amylase catalysis of polysaccharides, amylases were incubated with three different substrates, DP7, amylopectin, and maltodextrin DE10 liquefact, at 50° C., pH 5.3 for 2 hours. The oligosaccharides released by the enzymes were analyzed via HPLC.

A final concentration of 10 ppm amylase was incubated with 0.5% (w/v) substrate in 50 mM pH 5.3 sodium citrate buffer containing 50 mM NaCl and 2 mM $CaCl_2$ for 120 min at 50° C. The reaction was then stopped by adding the same volume of ethanol and centrifuging 10 min at 14,000 rpm. The supernatant was diluted by a factor of 10 using MilliQ water, and 10 μL was loaded onto an HPLC column Aminex HPX-42A, 300 mm×7.8 mm, equipped with a refractive index detector. The mobile phase was MilliQ water, and the flow rate was 0.6 mL/min at 85° C.

Table 4 shows the profile of oligosaccharides saccharified by AfAmyl and the AkAA benchmark for various substrates. Only oligosaccharides with DP1-DP7 are shown. The numbers in the Table reflect the peak area percentage of each DPn as a fraction of the total DP1-DP7. The AfAmyl produced mostly DP1 and DP2, with DP2 as the major product for all tested substrates. AfAmyl produced a composition of sugars containing at least 60% w/w DP2 relative to the combined amounts of DP1-DP7. AkAA, on the other hand, produced a product profile more evenly distributed from DP1 to DP4.

TABLE 4

| Product profile of fungal alpha-amylases on three substrates. | | | | | | | | |
|---|---|---|---|---|---|---|---|---|
| | | Percent Oligosaccharides Product Composition | | | | | | |
| Enzyme | Substrate | DP1 | DP2 | DP3 | DP4 | DP5 | DP6 | DP7 |
| AkAA | DP7 | 15 | 27 | 41 | 17 | 0 | 0 | ND |
| | Amylopectin | 14 | 20 | 46 | 21 | 0 | 0 | 0 |
| | DE10 Liquefact | 16 | 23 | 44 | 17 | 0 | 0 | 0 |
| AfAmy1 | DP7 | 21 | 79 | 0 | 0 | 0 | 0 | ND |
| | Amylopectin | 20 | 64 | 2 | 3 | 7 | 4 | 0 |
| | DE10 Liquefact | 20 | 68 | 1 | 3 | 5 | 3 | 0 |

Example 8: SSF Ethanol Fermentation

The ability of AfAmyl to produce ethanol and reduce (insoluble) residual starch (IRS) were tested in SSF. The results show that AfAmyl can achieve comparable effects as AkAA but at a reduced dosage.

The liquefact was obtained from Lincolnway Energy LLC (Nevada, Iowa, USA). SSF was carried out with AkAA or AfAmyl in the presence of a *Trichoderma* glucoamylase variant having a DP7 performance index of at least 1.15 (see U.S. Pat. No. 8,058,033 B2, Danisco US Inc.), according to the procedure below. After SSF, samples were analyzed for: (i) ethanol yield and DP3+ reduction using HPLC; and (ii) residual starch using a residual starch assay. The DP3+ levels are measured through the void volume, the reduction of which is commonly interpreted to reflect the efficiency of liquefact saccharification.

Liquefact Preparation: frozen liquefact (31% DS) was thawed overnight at room temperature before use. The liquefact was weighed, and pH was adjusted to 4.8 using 4N sulfuric acid and urea was added to a final concentration of 600 ppm.

Fermentation: ETHANOL RED® (LeSaffre) yeast was used to convert glucose to ethanol. Dry yeast was added to 0.1% w/w to the liquefact batch, and the composition was mixed well and incubated for 15 minutes at room temperature. 50 g+/−0.1 g liquefact (31% DS) was weighed into individually labeled 150 mL Erlynmeyer flasks. Glucoamylase was added to each flask at 49.5 μg protein/g solid. AkAA or AfAmyl alpha-amylases were added to each flask at varying dosages. The mixture was incubated in a forced air incubator with mixing at 100 rpm for 53 hours at pH 4.8, 32° C. About 1 mL corn slurry samples were taken at approximately t=5, 22, 29, 46 and 53 hours and centrifuged for 5 min at 15,000 rpm. 100 μL of the sample supernatants were mixed in individual microcentrifuge tubes with 10 μL of 1.1 N sulfuric acid and incubated 5 min at room temperature. 1 mL of water was added to each tube and the tubes were incubated at 95° C. for 5 minutes. The tubes were stored at 4° C. for further analysis. Samples were assayed for ethanol yield and DP3+ reduction. Furthermore at 53 hours (EOF) approximately 12 ml corn slurry sample was taken and directly stored at −20° C. for further analysis. These samples were assayed for residual starch.

(i) Ethanol Yield and DP3+ Reduction

To determine the ethanol yield and DP3+ reduction, time point samples were filtered and collected on an HPLC plate. The samples were analyzed on an Agilent HPLC using a Rezex Fast Fruit RFQ column with 6 min elution time. Calibration curves for the above components were generated using standard protocols.

Rates of ethanol production obtained with AfAmyl and a glucoamylase at pH 4.8 were comparable to those obtained with AkAA and a glucoamylase (data not shown). Similar results were obtained at pH 4.8 for the rate and yield of ethanol production and DP3+ hydrolysis (data not shown). By 21 hours, ethanol yield was about 8% v/v for the control and AfAmyl as the α-amylase. Similar ethanol yields for both were also observed at around 48 hours. The rate of DP3+ hydrolysis, however, was noticeably improved using AfAmyl and glucoamylase. At 6 hr, DP3+(w/v) was reduced from 23% to about 10% by AfAmyl and glucoamylase, compared to about 16-17% for the control. The final amount of DP3+ at 48 hr was about 3-4% in both cases. The same results at pH 4.8 for ethanol yield and the rate and extent of DP3+ hydrolysis were obtained using less AfAmyl than AkAA (data not shown), indicating that AfAmyl can be used at a reduced dosage compared to AkAA.

(ii) Residual Starch

The commercially available Megazyme Total Starch protocol (Megazyme International, Ireland) was adapted to quantitatively measure residual starch levels of a conventional fermentation of corn liquefact. 800 mg (+/−20 mg) of the EOF corn slurry was added to a polypropylene test tube followed by addition of 2 ml of 50 mM MOPS buffer pH 7.0. Then 3 mL of thermostable α-amylase (300 U) in 50 mM MOPS buffer, pH 7.0, was added, and the tube was vigorously stirred. The tube was incubated in a boiling water bath for 12 min with vigorous stirring after 4 min and 8 min. Subsequently 4 mL 200 mM sodium acetate buffer, pH 4.5, and 0.1 mL amyloglucosidase (50 U) were added. The tube was stirred on a vortex mixer and incubated in a water bath at 60° C. for 60 min. The mixture was centrifuged at 3,500 rpm for 5 min. 8 μl of the supernatant was transferred to a micro titer plate containing 240 μl of GOPOD Reagent. 8 μl of glucose controls and reagent blanks were also added to 240 μl GOPOD reagent and the samples were incubated at 50° C. for 20 min. After incubation absorbance at 510 nm was directly measured. The measured glucose amount for the EOF corn slurry was converted to the amount of residual starch.

Table 5 shows the residual starch level in the EOF corn slurry following SSF with AfAmyl and AkAA, both supplemented with the same amount of glucoamylase. The residual starch was found to be about the similar using 10 μg protein/g solid of AkAA (50% dose) and 3.3 μg protein/g solid for AfAmyl (17% dose). Given the data, AfAmyl appears at least three times more efficient than AkAA in removing residual starch.

TABLE 5

| Residual starch analysis for SSF with AfAmy1 and AkAA. | | |
|---|---|---|
| | Dosage (μg protein/g solid) | Residual Starch (% w/v) |
| AkAA | 10 | 0.732 ± 0.064 |
| AfAmy1 | 3.3 | 0.773 ± 0.054 |

Example 8: SSF Ethanol Fermentation with Isoamylase and Glucoamylase

The ability of AfAmyl with isoamylase and glucoamylase to produce ethanol and reduce (insoluble) residual starch (IRS) were tested in SSF. The results show that AfAmyl with isoamylase and glucoamylase can achieve comparable effects as AkAA with isoamylase and glucoamylase, but at a reduced dosage of the alpha amylase.

The liquefact was obtained from Lincolnway Energy LLC (Nevada, Iowa, USA). SSF was carried out with AkAA or AfAmyl, with or without isoamylase and in the presence of a *Trichoderma* glucoamylase variant having a DP7 performance index of at least 1.15 (see U.S. Pat. No. 8,058,033 B2, Danisco US Inc.), according to the procedure below. After SSF, samples were analyzed for: (i) ethanol yield and DP3+ reduction using HPLC; and (ii) residual starch using a residual starch assay. The DP3+ levels are measured through the void volume, the reduction of which is commonly interpreted to reflect the efficiency of liquefact saccharification.

Liquefact Preparation: frozen liquefact (31% DS) was thawed overnight at room temperature before use. The liquefact was weighed, and pH was adjusted to 4.8 using 4 N sulfuric acid and urea was added to a final concentration of 600 ppm.

Fermentation: ETHANOL RED® (LeSaffre) yeast was used to convert glucose to ethanol. Dry yeast was added to 0.1% w/w to the liquefact batch, and the composition was mixed well and incubated for 15 minutes at room temperature. 50 g+/−0.1 g liquefact (31% DS) was weighed into individually labeled 150 mL Erlynmeyer flasks. Glucoamylase was added to each flask at 49.5 μg protein/g solid. AkAA or AfAmyl alpha-amylases were added to each flask at varying dosages. Isoamylase was added to each flask at varying dosages. The mixture was incubated in a forced air incubator with mixing at 100 rpm for 53 hours at pH 4.8, 32° C. About 1 mL corn slurry samples were taken at approximately t=5, 22, 29, 46 and 53 hours and centrifuged for 5 min at 15,000 rpm. 100 μL of the sample supernatants were mixed in individual microcentrifuge tubes with 10 μL of 1.1 N sulfuric acid and incubated 5 min at room temperature. 1 mL of water was added to each tube and the tubes were incubated at 95° C. for 5 minutes. The tubes were stored at 4° C. for further analysis. Samples were assayed for ethanol yield, DP3+ reduction, and residual starch.

(i) Ethanol Yield and DP3+ Reduction

To determine the ethanol yield and DP3+ reduction, time point samples were filtered and collected on an HPLC plate. The samples were analyzed on an Agilent HPLC using a Rezex Fast Fruit RFQ column with 6 min elution time. Calibration curves for the above components were generated using standard protocols.

Rates of ethanol production obtained with 3.3 μg protein/g solid AfAmyl with isoamylase and a glucoamylase at pH 4.8 were comparable to those obtained with 10 μg protein/g solid AkAA with isoamylase and a glucoamylase. By 22 hours, ethanol yield was about 11.2% v/v for 3.3 μg protein/g solid AfAmyl in combination with 0.63 μg protein/g solid isoamylase and 49.5 μg protein/g solid glucoamylase, as compared to 10.9% v/v for 10 μg protein/g solid AkAA in combination with 0.63 μg protein/g solid isoamylase and 49.5 μg protein/g solid glucoamylase. Similar ethanol yields for both were also observed at around 46 hours: ethanol yield was 14.4% v/v for 3.3 μg protein/g solid AfAmyl in combination with 0.63 μg protein/g solid isoamylase and 49.5 μg protein/g solid glucoamylase, versus 13.8% v/v for 10 μg protein/g solid AkAA in combination with 0.63 μg protein/g solid isoamylase and 49.5 μg protein/g solid glucoamylase. See Table 6. The same effect on ethanol yield is seen even when the dose of isoamylase is increased to 1.3 μg protein/g solid. When 3.3 μg protein/g solid AfAmyl or 10 μg protein/g solid AkAA were combined with 49.5 μg protein/g solid glucoamylase and 1.3 μg protein/g solid isoamylase, similar results were obtained at pH 4.8 for the extent of ethanol yield after 46 hours, despite the difference in dosage. See Table 6.

TABLE 6

Ethanol yield analysis after 46 hours for SSF with AfAmy1 and AkAA in combination with isoamylase and glucoamylase.

| Enzyme combination | | | Dosage of Alpha Amylase (μg protein/g solid) | Ethanol yield (% v/v) |
|---|---|---|---|---|
| AkAA | Iso 0.63 μg | GA | 10 | 13.8 |
| AfAmy1 | prot/g solid | 49.5 μg | 3.3 | 14.4 |
| AkAA | Iso 1.3 μg | prot/g solid | 10 | 14.2 |
| AfAmy1 | prot/g solid | | 3.3 | 14.3 |

The rates of DP3+ hydrolysis were characterized for Akaa and AfAmyl, with isoamylase and glucoamylase, as shown in Table 7. Comparable results for the extent of DP3+ hydrolysis after 46 hours (i.e. 0.9 or 1.0% (w/v)) were obtained using 3.3 μg protein/g solid AfAmyl as were obtained using 10 μg protein/g solid AkAA, indicating that AfAmyl can be used at a reduced dosage compared to AkAA when either enzyme is combined with an invariant combination of 49.5 μg protein/g solid glucoamylase and 0.63 μg protein/g solid isoamylase. The same effect on DP3+ hydrolysis was seen even when the dose of isoamylase was increased to 1.3 μg protein/g solid. For example, when 3.3 μg protein/g solid AfAmyl or 10 μg protein/g solid AkAA were combined with 49.5 μg protein/g solid glucoamylase and 1.3 μg protein/g solid isoamylase, about the same results were obtained for the extent of DP3+ hydrolysis after 46 hours, i.e. 0.9% (w/v). In fact, the AfAmyl at the lower dosage was slightly more effective than the AkAA at the higher dosage, as less DP3+ remained after 46 or 53 hours.

TABLE 7

DP3+ analysis after 46 hours for SSF with AfAmy1 and AkAA in combination with isoamylase and glucoamylase.

| Enzyme combination | | | Dosage of Alpha Amylase (μg protein/g solid) | DP3+ (% w/v) |
|---|---|---|---|---|
| AkAA | Iso 0.63 μg | GA | 10 | 0.9 |
| AfAmy1 | prot/g solid | 49.5 μg | 3.3 | 1.0 |
| AkAA | Iso 1.3 μg | prot/g solid | 10 | 0.9 |
| AfAmy1 | prot/g solid | | 3.3 | 0.9 |

TABLE 8

DP3+ analysis after 29 hours for SSF with AfAmy1 in combination with glucoamylase with and without Isoamylase.

| Enzyme combination | | | Dosage of Alpha Amylase (μg protein/g solid) | DP3+ (% w/v) |
|---|---|---|---|---|
| AfAmy1 | No Iso | GA | 6.6 | 2.9 |
| AfAmy1 | Iso 0.63 μg prot/g solid | 49.5 μg prot/g solid | 3.3 | 2.7 |

Table 8 illustrates that comparable results at pH 4.8 for the extent of DP3+ hydrolysis after 29 hours (i.e., 2.7-2.9% (w/v)) were obtained using 3.3 μg protein/g solid AfAmyl in combination with 0.63 μg prot/g solid isoamylase as were obtained using 6.6 μg protein/g solid AfAmyl without isoamylase, when the alpha amylase is further combined with 49.5 μg protein/g solid glucoamylase. In other words, the dose of alpha amylase can be lowered by one half when adding 0.63 μg prot/g solid isoamylase, when the alpha amylase is further combined with 49.5 μg protein/g solid glucoamylase. The dose of isoamylase that is added (0.63 μg prot/g solid) corresponds to 9% of the dose of alpha amylase (6.6 μg protein/g solid) that is needed in the absence of isoamylase, to yield the same results.

TABLE 9

Ethanol analysis after 29 hours for SSF with AfAmy1 in combination with glucoamylase with and without Isoamylase.

| Enzyme combination | | | Dosage of Alpha Amylase (μg protein/g solid) | Ethanol (% w/v) |
|---|---|---|---|---|
| AfAmy1 | No Iso | GA | 10 | 12.4 |
| AfAmy1 | Iso 0.63 μg prot/g solid | 49.5 μg prot/g solid | 3.3 | 12.9 |

Table 9 illustrates that comparable results at pH 4.8 for the extent of Ethanol hydrolysis after 29 hours (i.e., 12.4-12.9% (w/v)) were obtained using 3.3 μg protein/g solid AfAmyl in combination with 0.63 μg prot/g solid isoamylase as were obtained using 10 μg protein/g solid AfAmyl without isoamylase, when the alpha amylase is further combined with 49.5 μg protein/g solid glucoamylase. In other words, the dose of alpha amylase can be lowered to about one third when adding 0.63 μg prot/g solid isoamylase, when the alpha amylase is further combined with 49.5 μg protein/g solid glucoamylase. The dose of isoamylase that is added (0.63 μg prot/g solid) corresponds to 6.3% of the dose of alpha amylase (10 μg protein/g solid) that is needed in the absence of isoamylase, to yield about the same results.

TABLE 10

Product profile after 29 hours for SSF with AfAmyl and AkAA in combination with isoamylase and glucoamylase. Products are expressed as (% w/v).

| Enzyme combination | | | Dosage of Alpha Amylase (μg protein/g solid) | DP1 (% w/v) | DP2 (% w/v) | DP1+DP2 (% w/v) |
|---|---|---|---|---|---|---|
| AkAA | Iso | GA | 3.3 | 0.4 | 0.9 | 1.3 |
| AfAmyl | 0.63 μg prot/g solid | 49.5 μg prot/g solid | 3.3 | 0.4 | 1.3 | 1.7 |

Table 10 shows the product profile after 29 hours for SSF with AfAmyl and AkAA in combination with isoamylase and glucoamylase, using the same dosage of alpha amylase (3.3 μs protein/g solid) for comparison purposes.

The results show that at 29 hours DP2 was enriched using AfAmyl in comparison to using AkAA, when either enzyme was used for SSF in combination with isoamylase and glucoamylase. DP1+DP2 was also enriched under the same conditions.

(ii) Residual Starch

The commercially available Megazyme Total Starch protocol (Megazyme International, Ireland) was adapted to quantitatively measure residual starch levels of a conventional fermentation of corn liquefact. 800 mg (+/−20 mg) of the EOF corn slurry was added to a polypropylene test tube followed by addition of 2 ml of 50 mM MOPS buffer pH 7.0. Then 3 mL of thermostable α-amylase (300 U) in 50 mM MOPS buffer, pH 7.0, was added, and the tube was vigorously stirred. The tube was incubated in a boiling water bath for 12 min with vigorous stirring after 4 min and 8 min. Subsequently 4 mL 200 mM sodium acetate buffer, pH 4.5, and 0.1 mL amyloglucosidase (50 U) were added. The tube was stirred on a vortex mixer and incubated in a water bath at 60° C. for 60 min. The mixture was centrifuged at 3,500 rpm for 5 min. 8 μl of the supernatant was transferred to a micro titer plate containing 240 μl of GOPOD Reagent. 8 μl of glucose controls and reagent blanks were also added to 240 μl GOPOD reagent and the samples were incubated at 50° C. for 20 min. After incubation absorbance at 510 nm was directly measured. The measured glucose amount for the EOF corn slurry was converted to the amount of residual starch.

Table 11 shows the residual starch level in the EOF corn slurry following SSF with AfAmyl and AkAA in combination with isoamylase and glucoamylase. The residual starch was found to be comparable using 10 μg protein/g solid of AkAA and 3.3 μg protein/g solid for AfAmyl, when the dose of isoamylase and glucoamylase is kept constant. Comparable results at pH 4.8 for the residual starch level after 53 hours were obtained using 3.3 μg protein/g solid AfAmyl as were obtained using 10 μg protein/g solid AkAA when combined with 49.5 μg protein/g solid glucoamylase and 0.63 μg protein/g solid isoamylase, i.e. 0.650±0.029% (w/v) for AkAA versus 0.756±0.082% (w/v) for AfAmyl. This indicates that AfAmyl can be used at a reduced dosage compared to AkAA when either enzyme is combined with an invariant combination of 49.5 μg protein/g solid glucoamylase and 0.63 μg protein/g solid isoamylase. A similar effect on residual starch level was seen when the dose of isoamylase was increased to 1.3 μg protein/g solid. For example, when 3.3 μg protein/g solid AfAmyl or 10 μg protein/g solid AkAA were combined with 49.5 μg protein/g solid glucoamylase and 1.3 μg protein/g solid isoamylase, slightly better results were obtained for the residual starch level after 53 hours with 3.3 μg protein/g solid AfAmyl than with 10 μg protein/g solid AkAA, i.e. 0.638±0.029% (w/v) for AkAA versus 0.662±0.044% (w/v) for AfAmyl.

Given the data, AfAmyl in combination with isoamylase and glucoamylase appears about three times more efficient than AkAA in combination with isoamylase and glucoamylase in removing residual starch.

TABLE 11

Residual starch analysis for SSF with different doses of AfAmy1 and AkAA in combination with isoamylase and glucoamylase.

| Enzyme combination | | | Dosage of Alpha Amylase (µg protein/g solid) | Residual Starch (% w/v) |
|---|---|---|---|---|
| AkAA | Iso 0.63 µg | GA | 10 | 0.650 ± 0.029 |
| AfAmy1 | prot/g solid | 49.5 µg | 3.3 | 0.756 ± 0.082 |
| AkAA | Iso 1.3 µg | prot/g solid | 10 | 0.638 ± 0.029 |
| AfAmy1 | prot/g solid | | 3.3 | 0.662 ± 0.044 |

Table 12 shows the residual starch level in the EOF corn slurry following SSF with equal doses of AfAmyl and AkAA in combination with isoamylase and glucoamylase. The residual starch was found to be reduced by about 2% using 3.3 µg protein/g solid of AfAmyl versus 3.3 µg protein/g solid of AkAA, when the dose of isoamylase was 0.63 µg protein/g solid and the dose of isoamylase was 49.5 µg protein/g solid. The residual starch was found to be reduced by about 11% using 3.3 µg protein/g solid of AfAmyl versus 3.3 µg protein/g solid of AkAA, when the dose of isoamylase was 1.3 µg protein/g solid and the dose of glucoamylase was 49.5 µg protein/g solid.

TABLE 12

Residual starch analysis for SSF with equal doses of AfAmy1 and AkAA in combination with isoamylase and glucoamylase.

| Enzyme combination | | | Dosage of Alpha Amylase (µg protein/g solid) | Residual Starch (% w/v) | % Reduction |
|---|---|---|---|---|---|
| AkAA | Iso | GA | 3.3 | 0.769 ± 0.004 | |
| AfAmy1 | 0.63 µg prot/g solid | 49.5 µg prot/g solid | 3.3 | 0.756 ± 0.082 | 2% |
| AkAA | Iso | | 3.3 | 0.748 ± 0.043 | |
| AfAmy1 | 1.3 µg prot/g solid | | 3.3 | 0.662 ± 0.044 | 11% |

TABLE 13

Residual starch analysis with AfAmy1 in combination with glucoamylase with and without isoamylase.

| Enzyme combination | | | Dosage of Alpha Amylase (µg protein/g solid) | Residual Starch (% w/v) |
|---|---|---|---|---|
| AfAmy1 | No Iso | GA | 10 | 0.658 ± 0.044 |
| AfAmy1 | Iso 1.3 µg prot/g solid | 49.5 µg prot/g solid | 3.3 | 0.662 ± 0.044 |

Table 13 shows the residual starch level in the EOF corn slurry following SSF with AfAmyl in combination with glucoamylase with and without isoamylase. It illustrates that about the same results (i.e., 0.658-0.662% (w/v)) were obtained using 3.3 µg protein/g solid AfAmyl in combination with 1.3 µg prot/g solid isoamylase as were obtained using 10 µg protein/g AfAmyl without isoamylase, when the alpha amylase is further combined with 49.5 µg protein/g solid glucoamylase. In other words, the dose of alpha amylase can be lowered to about one third when adding 1.3 µg prot/g solid isoamylase, when the alpha amylase is further combined with 49.5 µg protein/g solid glucoamylase. The dose of isoamylase that is added (1.3 µg prot/g solid) corresponds to 13% of the dose of alpha amylase (10 µg protein/g solid) that is needed in the absence of isoamylase, to yield about the same results.

SEQUENCE LISTING

SEQ ID NO: 1

Protein sequence of wild-type AfAmy1 (full length, w/ signal peptide):

*MKWIAQLFPLSLCSSLLGQAAHA*LTPAEWRSQSIYFLLTDRFGREDNSTTAACDVTQRLYCGGSW

QGIINHLDYIQGMGFTAIWITPVTEQFYENTGDGTSYHGYWQQNIHEVNANYGTAQDLRDLANAL

-continued

HARGMYLMVDVVANHMGYNGAGNSVNYGVFTPFDSATYFHPYCLITDYNNQTAVEDCWLGDTTVS

LPDLDTTSTAVRSIWYDWVKGLVANYSIDGLRIDTVKHVEKDFWPGYNDAAGVYCVGEVFSGDPQ

YTCPYQNYLDGVLNYPIYYQLLYAFQSTSGSISNLYNMISSVASDCADPTLLGNFIENHDNPRFA

SYTSDYSQAKNVISFMFFSDGIPIVYAGQEQHYSGGADPANREAVWLSGYSTSATLYSWIASTNK

IRKLAISKDSAYITSKNNPFYYDSNTLAMRKGSVAGSQVITVLSNKGSSGSSYTLSLSGTGYSAG

ATLVEMYTCTTLTVDSSGNLAVPMVSGLPRVFVPSSWVSGSGLCGDSISTTATAPSATTSATATR

TACAAATAIPILFEELVTTTYGESIYLTGSISQLGNWDTSSAIALSASKYTSSNPEWYVTVTLPV

GTSFEYKFVKKGSDGSIAWESDPNRSYTVPTGCAGTTVTVSDTWR

SEQ ID NO: 2

Nucleotide sequence of the AfAmy1 gene (genomic sequence, w/ introns):

ATGAAGTGGATCGCGCAGCTCTTCCCGTTGTCCCTGTGCTCGTCCCTGCTCGGACAGGCTGCCCA

TGCTCTGACCCCAGCCGAATGGCGCAGTCAATCGATCTATTTCCTCCTGACCGATCGGTTCGGCC

GAGAAGACAATTCCACGACTGCTGCCTGCGATGTCACGCAACGAgtgtgtccccctatcgttctt gatcgagctcatgctaacatttgcagCTGTATTGCGGCGGGAGCTGGCAGGGGATCATCAATCAT gtacgactgtcccatatcgcgcggtcgaaactaacaatgtcagCTCGACTACATTCAAGGCATGG

GATTTACTGCCATATGGATCACCCCCGTAACTGAGCAGTTCTATGAGAACACCGGCGATGGTACT

TCGTACCATGGATACTGGCAGCAGAATATgtgagttctctttggccgcggtgattcatactaatc gacgaagCCACGAGGTCAATGCCAATTATGGAACGGCACAAGATCTTAGAGATCTGGCCAACGCT CTGCACGCGCGTGGCATGTACTTGATGGTCGATGTGGTCGCCAACCATATGgtacgccgtcttct cgagttgtacattataatctgactggttaagGGCTACAACGGAGCGGGAAACTCGGTCAACTACG

GTGTCTTCACTCCGTTTGATTCCGCTACCTATTTCCACCCATACTGTCTCATCACCGACTACAAC

AACCAAACAGCTGTGGAGGACTGCTGGCTGGGAGATACTACTGTCTCGCTACCCGATCTCGACAC

GACCAGCACGGCAGTGCGAAGCATCTGGTATGATTGGGTGAAGGGATTGGTTGCCAACTACTCCA gtcagtgagagccgcatccgagcgtgaatgatactgaccgagatagTCGACGGCCTGCGCATCGA

CACGGTGAAGCATGTCGAGAAAGACTTCTGGCCCGGCTACAATGACGCTGCTGGCGTCTACTGTG

TCGGTGAAGTCTTTTCGGGTGATCCACAATATACCTGTCCATACCAGAATTACCTGGATGGTGTA

CTCAACTACCCCATgtacgcattatgatttccgtacggatttgatcctgacgagagcagATACTA

TCAACTTCTCTACGCGTTCCAATCGACCAGCGGCAGCATCAGCAATCTGTACAACATGATCAGCT

CCGTTGCGTCTGACTGTGCGGATCCCACTTTGCTCGGCAACTTTATCGAGAACCATGATAACCCC

CGATTTGCCTCgtaagaccgtgcctccgttccctgaatgcaactaacctccccagCTATACGAGC

GACTATTCGCAAGCCAAGAACGTCATCTCCTTCATGTTCTTCTCCGACGGCATCCCCATTGTCTA

CGCCGGACAGGAGCAGCACTACAGCGGCGGTGCTGACCCTGCCAACCGCGAGGCTGTCTGGCTGT

CTGGATACTCGACCAGCGCTACGCTGTACAGCTGGATTGCCTCTACCAACAAGATTCGCAAGCTA

GCGATTTCCAAAGACTCAGCCTACATAACATCCAAGgtatttccggtcacgtcttcgcattccac cgctaacatcgatagAACAACCCGTTCTACTATGATTCCAATACTCTCGCTATGCGCAAGGGCTC

AGTCGCTGGCTCTCAAGTCATTACCGTCCTCAGTAACAAGGGATCCTCGGGCAGTTCCTACACCC

TCTCTCTCAGCGGCACGGGCTACTCCGCCGGCGCCACCCTTGTCGAGATGTATACATGCACTACT

CTCACCGTGGACTCGAGCGGAAATCTCGCCGTGCCAATGGTATCCGGCTTGCCCAGAGTTTTCGT

GCCCTCGTCATGGGTCAGTGGGAGTGGCCTCTGCGGCGACTCTATCTCCACCACGGCGACCGCCC

CCAGTGCCACCACGAGCGCAACAGCGACAAGAACAGCATGCGCAGCTGCCACAGCCATTCCGATT

CTCTTCGAGGAGCTCGTGACAACTACCTACGGCGAGTCCATCTACCTGACCGGCTCGATCAGCCA

-continued

ACTCGGGAACTGGGACACGAGTTCTGCGATTGCTCTGTCGGCGAGTAAATACACCTCGTCGAACC

CTGAGTGGTATGTCACCGTGACCCTGCCTGTTGGCACCTCATTTGAGTACAAATTCGTCAAGAAG

GGGTCGGATGGGAGCATCGCGTGGGAAAGTGATCCGAACCGGTCGTATACGGTGCCGACTGGGTG

TGCGGGAACGACCGTGACGGTGTCTGATACGTGGAGATGA

SEQ ID NO: 3

Coding sequence of the AfAmy1 gene (cDNA sequence, w/o introns):
ATGAAGTGGATCGCGCAGCTCTTCCCGTTGTCCCTGTGCTCGTCCCTGCTCGGACAGGCTGCCCA

TGCTCTGACCCCAGCCGAATGGCGCAGTCAATCGATCTATTTCCTCCTGACCGATCGGTTCGGCC

GAGAAGACAATTCCACGACTGCTGCCTGCGATGTCACGCAACGACTGTATTGCGGCGGGAGCTGG

CAGGGGATCATCAATCATCTCGACTACATTCAAGGCATGGGATTTACTGCCATATGGATCACCCC

CGTAACTGAGCAGTTCTATGAGAACACCGGCGATGGTACTTCGTACCATGGATACTGGCAGCAGA

ATATCCACGAGGTCAATGCCAATTATGGAACGGCACAAGATCTTAGAGATCTGGCCAACGCTCTG

CACGCGCGTGGCATGTACTTGATGGTCGATGTGGTCGCCAACCATATGGGCTACAACGGAGCGGG

AAACTCGGTCAACTACGGTGTCTTCACTCCGTTTGATTCCGCTACCTATTTCCACCCATACTGTC

TCATCACCGACTACAACAACCAAACAGCTGTGGAGGACTGCTGGCTGGGAGATACTACTGTCTCG

CTACCCGATCTCGACACGACCAGCACGGCAGTGCGAAGCATCTGGTATGATTGGGTGAAGGGATT

GGTTGCCAACTACTCCATCGACGGCCTGCGCATCGACACGGTGAAGCATGTCGAGAAAGACTTCT

GGCCCGGCTACAATGACGCTGCTGGCGTCTACTGTGTCGGTGAAGTCTTTTCGGGTGATCCACAA

TATACCTGTCCATACCAGAATTACCTGGATGGTGTACTCAACTACCCCATATACTATCAACTTCT

CTACGCGTTCCAATCGACCAGCGGCAGCATCAGCAATCTGTACAACATGATCAGCTCCGTTGCGT

CTGACTGTGCGGATCCCACTTTGCTCGGCAACTTTATCGAGAACCATGATAACCCCCGATTTGCC

TCCTATACGAGCGACTATTCGCAAGCCAAGAACGTCATCTCCTTCATGTTCTTCTCCGACGGCAT

CCCCATTGTCTACGCCGGACAGGAGCAGCACTACAGCGGCGGTGCTGACCCTGCCAACCGCGAGG

CTGTCTGGCTGTCTGGATACTCGACCAGCGCTACGCTGTACAGCTGGATTGCCTCTACCAACAAG

ATTCGCAAGCTAGCGATTTCCAAAGACTCAGCCTACATAACATCCAAGAACAACCCGTTCTACTA

TGATTCCAATACTCTCGCTATGCGCAAGGGCTCAGTCGCTGGCTCTCAAGTCATTACCGTCCTCA

GTAACAAGGGATCCTCGGGCAGTTCCTACACCCTCTCTCTCAGCGGCACGGGCTACTCCGCCGGC

GCCACCCTTGTCGAGATGTATACATGCACTACTCTCACCGTGGACTCGAGCGGAAATCTCGCCGT

GCCAATGGTATCCGGCTTGCCCAGAGTTTTCGTGCCCTCGTCATGGGTCAGTGGGAGTGGCCTCT

GCGGCGACTCTATCTCCACCACGGCGACCGCCCCCAGTGCCACCACGAGCGCAACAGCGACAAGA

ACAGCATGCGCAGCTGCCACAGCCATTCCGATTCTCTTCGAGGAGCTCGTGACAACTACCTACGG

CGAGTCCATCTACCTGACCGGCTCGATCAGCCAACTCGGGAACTGGGACACGAGTTCTGCGATTG

CTCTGTCGGCGAGTAAATACACCTCGTCGAACCCTGAGTGGTATGTCACCGTGACCCTGCCTGTT

GGCACCTCATTTGAGTACAAATTCGTCAAGAAGGGGTCGGATGGGAGCATCGCGTGGGAAAGTGA

TCCGAACCGGTCGTATACGGTGCCGACTGGGTGTGCGGGAACGACCGTGACGGTGTCTGATACGT

GGAGATGA

SEQ ID NO: 4

Amino acid sequence of the AfAmy1 signal peptide:
MKWIAQLFPLSLCSSLLGQAAHA

SEQ ID NO: 5

Putative alpha-amylase from *Neosartorya fischeri* NRRL 181:
>gi|119497741|ref|XP_001265628.1|alpha-
amylase, putative [*Neosartorya fischeri* NRRL 181]
MKWISPLLPLSLSLCLLGQAAHALTPAEWRSQSIYFLLTDRFGREDNSTTAACDVTQRLYCGGSW -continued

QGIINHLDYIQGMGFTAIWITPVTQQFYENTGDGTSYHGYWQQNIYEVNSNYGTAQDLRKLADAL

HARGMYLMVDVVANHMGYDGAGNSVDYSVFTPFDSSTYFHTYCLISDYNNQNNVEDCWLGDTTVS

LPDLDTTNTAVRTIWYDWVKGLVANYSIDGLRIDTVKHVEKDFWPDYNDAAGVYCVGEVFSGDPS

YTCPYQNYMDGVLNYPIYYQLLYAFQSTSGSISNLYNMISSVDSDCADPTLLGNFIENHDNPRFA

SYTSDYSQAKNVISFMFFSDGIPIVYAGQEQHYSGGADPANREAVWLSGYSTSATLYSWIASTNK

IRKLAISKDSAYITSKNNPFYYDSNTLAMRKGSVAGSQVITVLSNKGSSGSSYTLSLSGTGYSAG

ATLVEMYTCTTLTVDSSGNLAVPMASGLPRVLVPSSWVSGSGLCGDSISTIATTTTSTTKTTTVA

TTTACASATALPILFEELVTTTYGETIYLTGSISQLGNWDTSSAIALSASKYTSSNPEWYATVTL

PVGTSFQYKFFKKESDGSIVWESDPNRSYTVPAGCAGTTVTVSDTWR

SEQ ID NO: 6

Alpha-amylase precursor from *Aspergillus terreus* NIH2624
>gi|115385717|ref|XP_001209405.1|alpha-
amylase precursor [*Aspergillus terreus* NIH2624]
MKWTSSLLLLLSVIGQATHALTPAEWRSQSIYFLLTDRFGRTDNSTTAACDTSDRVYCGGSWQGI

INQLDYIQGMGFTAIWITPVTGQFYENTGDGTSYHGYWQQDIYDLNYNYGTAQDLKNLANALHER

GMYLMVDVVANHMGYDGAGNTVDYSVFNPFSSSSYFHPYCLISNYDNQTNVEDCWLGDTTVSLPD

LDTTSTAVRNIWYDWVADLVANYSIDGLRVDTVKHVEKDFWPGYNSAAGVYCVGEVYSGDPAYTC

PYQNYMDGVLNYPIYYQLLYAFESSSGSISDLYNMISSVASSCKDPTLLGNFIENHDNPRFASYT

SDYSQAKNVITFIFLSDGIPIVYAGQEQHYSGGSDPANREATWLSGYSTSATLYTWIATTNQIRS

LAISKDAGYVQAKNNPFYSDSNTIAMRKGTTAGAQVITVLSNKGASGSSYTLSLSGTGYSAGATL

VETYTCTTVTVDSSGNLPVPMTSGLPRVFVPSSWVNGSALCNTECTAATSISVLFEELVTTTYGE

NIYLSGSISQLGSWNTASAVALSASQYTSSNPEWYVSVTLPVGTSFQYKFIKKGSDGSVVWESDP

NRSYTVPAGCEGATVTVADTWR

SEQ ID NO: 7

Alpha-amylase AMYI from *Ophiostoma floccosum*:
>gi|104345338|gb|ABF72529.1|alpha amylase AMYI
[*Ophiostoma floccosum*]
MKLSSLLPLAFLGQAVNALSPAEWRKQSIYFLLTDRFGRTDNSTSATCNTGDRAYCGGSWQGVIN

HLDYIQGMGFTAIWITPVTGQFYESTGDGTSYHGYWQQDIYSLNSHLGDQNDLKALSAALHARGM

YLMVDVVANHMGYDGAGSNVDYSVFDAFPSSSYFHSYCEISNYDDQSNVEDCWLGDTTVSLPDLN

TELTSVRSIWNSWVAGLVANYSIDGLRIDTVKHVETSFWPGYNDAAGVYCVGEVFDGDPAYTCAY

QNYMDGVLNYPIYYQLLSAFESTSGSISNLYNMIKSVASDCADPTLLGNFIENHDNPRFASYTSD

YSLAQNAISFLFFSDGIPIVYSGQEQHYSGGADPANREATWLSGYSTTATLYKHIKTTNQIRSLI

IGKDSSWATSANSPFYQDSNTIAMLKGSASGSKVLTVLSNKGASGSSYTLSLGSTGYSSGASLVE

LYSCTTVTVDSSGNVPVPMASGLPRVLVPSSWVSGSGLCGTAVTTGTATATGTSTKATTATATTA

TSCTAATAVSVVFNELATTTYGENVYIIGSTSQLGSWSTANAIALSSSDYTSSNPLWHVTVSLPA

GSSFTYKFIKKESDGTFVWESDPNRSYTVPTGCSGLSATVSATWR

SEQ ID NO: 8

Putative alpha-amylase from *Penicillium chrysogenum*
Wisconsin 54-1255: >gi|255939426|ref|
XP_002560482.1|Pc16g00630 [*Penicillium*
*chrysogenum* Wisconsin 54-1255]
MKKVIFTATILLWQMVMGLTPAEWRSQSIYFLLTDRFGRTDNSVTANCNVDDRAYCGGTWQGIIN

QLDYIQGMGFTAIWITPVTKQLPQDTGYGMAYHGYWQQDIYDVNDHHGTSDDLLALSKALHARGM

YLMVDVVANHMGYAGAGNTVDYSVFTPFSSSSYFHPYCLISNYNDQSNVENCWLGDTTVSLPDLD

TTQNSVQTIWNDWIADLVTKYSIDGLRIDTVKHVQKSFWPGFNDAAGVYAVGEIFDGNPAYTCDY

QNYMDGVLNYPIYYPLLRAFQSSSGSISDLYNMVGTVASSCADSTLLGNFIENHDNPRFPSYTSD

-continued

YSQAKNVISFLFLSDGIPIVYAGQEQHYSGGHDPANREAVWLSGYSTTAELYQHIATTNKIRKAA

VAADSSYITSKNVPFYQDSHTLAMKKGSGSSPVITVLSNAGSSGSSYTLYLGGSGYSSGTKLMEM

HTCTSITVDSSGKIAVPMVSGLPRVLIPASSVSNSGLCGSSVPSATATQTTTATTTGAGCTQATA

LPVLFKELVTTVYGQDIYISGSISQLGNWDTSQAIALSSSSYTASNPLWQTTITLPVGTTFQYKF

LKKTTGSSTVTWESDPNRSYTVPTGCTGATATVAASWK

SEQ ID NO: 9

Putative alpha-amylase from *Aspergillus clavatus* NRRL 1:
>gi|121711036|ref|XP_001273134.1|alpha-amylase, putative [*Aspergillus clavatus* NRRL 1]

MKWSTVPLSLSLLGQAVNALTPAEWRSQSIYFLLTDRFGRDDRSTSAPCDTNQRMYCGGTWQGII

NQLDYIQGMGFTAIWITPVTEQFYESTGDGSSYHGYWQQNINEVNRKHGTKQDLKNLADALHARG

MYLMVDVVANHMGYRGSGQNVDFNTFHPFNRAEHYNSFCTITDYNNQNSVEKCWLGSNTVSLPDL

ATTHPWVRSTWYDWVRDLVKDYSIDGLRIDTVKHVEKDFWRPYNDAAGVYCVGEIFSGDPGYTCD

YQNHMDGVLNYPIYYPLLNAFKSTSGSMGDLRNMIGTVSNKCRDPTLLGNFIENHDNPRFAHYTN

DISQAKNVLTFMFLTDGIPIVYAGQEQHYDGGEDPHNREATWFSGYNKNAELYTWIAKTNKIRSL

AVSKDSGYVTARNNPFYHDTTTLAMRKGSRDGAQVITIVSNKGASGDGYTMQLSGHGYGSGATVM

EMYTCTPLTVGGNGIIPVPMVSGQPRVLVPSSWVAGSGLCGSTGPSTTTTPSTTTTPSTTTATEP

GTTCTAASTLPVQFQERVTTNYGDSVFIVGSIPQLGGWDVKKAVALSAEKYTPGNPEWRATITLP

VGTKFEYKFIKKQSNGQIVWENDPNRTYNVPSQCAGTVATASSSWK

SEQ ID NO: 10

Acid-stable alpha-amylase from *Aspergillus kawachii*:
>gi|2570150|dbj|BAA22993.1|acid-stable alpha-amylase [*Aspergillus kawachii*]

MRVSTSSIALAVSLFGKLALGLSAAEWRTQSIYFLLTDRFGRTDNSTTATCNTGDQIYCGGSWQG

IINHLDYIQGMGFTAIWISPITEQLPQDTSDGEAYHGYWQQKIYYVNSNFGTADDLKSLSDALHA

RGMYLMVDVVPNHMGYAGNGNDVDYSVFDPFDSSSYFHPYCLITDWDNLTMVQDCWEGDTIVSLP

DLNTTETAVRTIWYDWVADLVSNYSVDGLRIDSVEEVEPDFFPGYQEAAGVYCVGEVDNGNPALD

CPYQKYLDGVLNYPIYWQLLYAFESSSGSISNLYNMIKSVASDCSDPTLLGNFIENHDNPRFASY

TSDYSQAKNVLSYIFLSDGIPIVYAGEEQHYSGGDVPYNREATWLSGYDTSAELYTWIATTNAIR

KLAISADSDYITYKNDPIYTDSNTIAMRKGTSGSQIITVLSNKGSSGSSYTLTLSGSGYTSGTKL

IEAYTCTSVTVDSNGDIPVPMASGLPRVLLPASVVDSSSLCGGSGNTTTTTAATSTSKATTSSS

SSSAAATTSSSCTATSTTLPITFEELVTTTYGEEVYLSGSISQLGEWHTSDAVKLSADDYTSSNP

EWSVTVSLPVGTTFEYKFIKVDEGGSVTWESDPNREYTVPECGSGSGETVVDTWR

SEQ ID NO: 11

Alpha-amylase from *Aspergillus awamori*:
>gi|40313278|dbj|BAD06003.1|alpha-amylase [*Aspergillus awamori*]

MRVSTSSLALSVSLFGKLALGLSAAEWRSQSIYELLTDREGRTDNSTTATCDTGDQIYCGGSWQG

IINHLDYIQGMGFTAIWISPITEQLPQDTSDGEAYHGYWQQKIYDVNSNFGTADDLKSLSDALHA

RGMYLMVDVVPNHMGYAGNGNDVDYSVFDPFDSSSYFHPYCLITDWDNLTMVQDCWEGDTIVSLP

DLNTTETAVRTIWYDWVADLVSNYSVDGLRIDSVLEVEPDFFPGYQEAAGVYCVGEVDNGNPALD

CPYQDYLDGVLNYPIYWQLLYAFESSSGSISDLYNMIKSVASDCSDPTLLGNFIENHDNPRFASY

TSDYSQAKNVLSYIFLSDGIPIVYAGEEQHYSGGDVPYNREATWLSGYDTSAELYTWIATTNAIR

KLAISADSDYITYANDPIYTDSNTIAMRKGTSGSQVITVLSNKGSSGSSYTLTLSGSGYTSGTEL

IEAYTCTSVTVDSNGDIPVPMASGLPRVLLPAWVVDSSSSLWGGSTTTTTSSSTSTSTSKATSSS

STTTSSSCTATSTTLPITLEELVTTTYGEEIYLSGSISQLGEWDTSDAVKLSADDYTSSNPEWYV

TVSLPVGTTFEYKFIKVEEDGSVTWESDPNREYTVPECGSGETVVDTWR

-continued

SEQ ID NO: 12

Synthetic primer:
5'-ccgcggccgcaccATGAAGTGGATCGCGCAGCT-3'

SEQ ID NO: 13

Synthetic primer:
5'-ccggcgcgcccttaTCATCTCCACGTATCAGACAC-3'

SEQ ID NO: 14

AfAmyl putative carbohydrate binding domain (position 523 to position 630 of SEQ ID NO: 1):
CAAATAIPILFEELVTTTYGESIYLTGSISQLGNWDTSSAIALSASKYTSSNPEWYVTVTLPVGT

SFEYKFVKKGSDGSIAWESDPNRSYTVPTGCAGTTVTVSDTWR

SEQ ID NO: 15

AfAmyl putative linker (linker region; position 503 to position 522 of SEQ ID NO: 1):
ISTTATAPSATTSATATRTA

SEQ ID NO: 16

Putative alpha-amylase from *Aspergillus fumigatus* A1163:
>gi|159128622|gb|EDP53736.1|alpha-amylase,
putative [*Aspergillus fumigatus* A1163]
MKWISQLFPLSLCSSLLGQAAHALTPAEWRSQSIYFLLTDRFGREDNSTTAACDVTQRLYCGGSW

QGIINHLDYIQGMGFTAIWITPVTEQFYENTGDGTSYHGYWQQNIHEVNANYGTAQDLRDLANAL

HARGMYLMVDVVANHMGYNGAGNSVNYGVFTPFDSATYFHPYCLITDYNNQTAVEDCWLGDTTVS

LPDLDTTSTAVRSIWYDWVKGLVANYSIDGLRIDTVKHVEKDEWPGYNDAAGVYCVGEVFSGDPQ

YTCPYQNYLDGVLNYPIYYQLLYAFQSTSGSISNLYNMISSVASDCADPTLLGNFIENHDNPRFA

SYTSDYSQAKNVISFMFFSDGIPIVYAGQEQHYSGGADPANREAVWLSGYSTSATLYSWIASTNK

IRKLAISKDSAYITSKNNPFYYDSNTLAMRKGSVAGSQVITVLSNKGSSGSSYTLSLSGTGYSAG

ATLVEMYTCTTLTVDSSGNLAVPMVSGLPRVFVPSSWVSGSGLCGDSISTTATAPSATTSATATR

TACAAATAIPILFEELVTTTYGESIYLTGSISQLGNWDTSSAIALSASKYTSSNPEWYVTVTLPV

GTSFEYKFVKKGSDGSIAWESDPNRSYTVPTGCAGTTVTVSDTWR

SEQ ID NO: 17

α-Amylase from *Aspergillus niger* (Protein Data Base entry 2GUY|A)
ATPADWRSQSIYFLLTDRFARTDGSTTATCNTADQKYCGGTWQGIIDKLDYIQGMGFTAI

WITPVTAQLPQTTAYGDAYHGYWQQDIYSLNENYGTADDLKALSSALHERGMYLMVDVVA

NHMGYDGAGSSVDYSVFKPFSSQDYFHPFCFIQNYEDQTQVEDCWLGDNTVSLPDLDTTK

DVVKNEWYDWVGSLVSNYSIDGLRIDTVKHVQKDFWPGYNKAAGVYCIGEVLDGDPAYTC

PYQNVMDGVLNYPIYYPLLNAFKSTSGSMDDLYNMINTVKSDCPDSTLLGTFVENHDNPR

FASYTNDIALAKNVAAFIILNDGIPIIYAGQEQHYAGGNDPANREATWLSGYPTDSELYK

LIASANAIRNYAISKDTGFVTYKNWPIYKDDTTIAMRKGTDGSQIVTILSNKGASGDSYT

LSLSGAGYTAGQQLTEVIGCTTVTVGSDGNVPVPMAGGLPRVLYPTEKLAGSKICSSS

---

What is claimed is:

1. A method of saccharifying a composition comprising starch to produce a composition comprising glucose, wherein said method comprises:

(i) contacting said composition comprising starch with an isoamylase and an isolated AfAmyl or variant thereof having α-amylase activity comprising an amino acid sequence with at least 80% amino acid sequence identity to (a) residues 24-630 of SEQ ID NO:1 or (b) residues 24-502 of SEQ ID NO:1; and (ii) saccharifying said composition comprising starch to produce said composition comprising glucose; wherein said isoamylase and said isolated AfAmyl or variant thereof catalyze the saccharification of the starch composition to glucose wherein the AfAmyl or variant thereof is dosed at 17%-50% the dose of AkAA, to reduce the same quantity of residual starch under the same conditions, and wherein the saccharification results in 2%-11% less residual starch compared to a saccharification carried out by said isoamylase and AkAA under the same conditions.

2. The method of claim 1, wherein the AfAmyl or variant thereof is dosed at about 17%-50% the dose of AkAA, to reduce the same quantity of DP3+ under the same conditions.

3. The method of claim 1, wherein said composition comprising glucose is enriched in DP2 or (DP1+DP2), compared to a second composition comprising glucose produced by AkAA with said isoamylase under the same conditions.

4. The method of claim 1, wherein the AfAmyl or variant thereof is dosed at about 33% the dose of AfAmyl that would be required to reduce the same quantity of residual starch under the same conditions in the absence of isoamylase, and optionally, wherein said isoamylase is dosed at about 13% the dose of AfAmyl that would be required to reduce the same quantity of residual starch under the same conditions in the absence of isoamylase.

5. The method of claim 1, wherein the AfAmyl or variant thereof is dosed at about 50% the dose of AfAmyl that would be required to reduce the same quantity of DP3+ under the same conditions in the absence of isoamylase, and optionally, wherein said isoamylase is dosed at about 9% the dose of AfAmyl that would be required to reduce the same quantity of DP3+ under the same conditions in the absence of isoamylase.

6. The method of claim 1, wherein the AfAmyl or variant thereof is dosed at about 33% the dose of AfAmyl that would be required to produce the same ethanol yield under the same conditions in the absence of isoamylase, and optionally, wherein said isoamylase is dosed at about 6.3% the dose of AfAmyl that would be required to produce the same ethanol yield under the same conditions in the absence of isoamylase.

7. The method of claim 1, wherein said AfAmyl or variant thereof comprises an amino acid sequence with at least 90%, 95%, or 99% amino acid sequence identity to (a) residues 24-630 of SEQ ID NO:1 or (b) residues 24-502 of SEQ ID NO:1.

8. The method of claim 7, wherein said AfAmyl or variant thereof comprises (a) residues 24-630 of SEQ ID NO:1 or (b) residues 24-502 of SEQ ID NO:1.

9. The method of claim 1, wherein said AfAmyl or variant thereof consists of an amino acid sequence with at least 80%, 90%, 95%, or 99% amino acid sequence identity to (a) residues 24-630 of SEQ ID NO:1 or (b) residues 24-502 of SEQ ID NO:1.

10. The method of claim 9, wherein said AfAmyl or variant thereof consists of (a) residues 24-630 of SEQ ID NO:1 or (b) residues 24-502 of SEQ ID NO:1.

11. The method of claim 1, further comprising fermenting the glucose composition to produce an End of Fermentation (EOF) product.

12. The method of claim 11, wherein said fermentation is a simultaneous saccharification and fermentation (SSF) reaction.

13. A method of producing a fermented beverage, comprising (i) contacting said composition comprising starch with an isoamylase and an isolated AfAmyl or variant thereof having α-amylase activity comprising an amino acid sequence with at least 80% amino acid sequence identity to (a) residues 24-630 of SEQ ID NO:1 or (b) residues 24-502 of SEQ ID NO:1; and (ii) saccharifying said composition comprising starch to produce said composition comprising glucose; wherein said isoamylase and said isolated AfAmyl or variant thereof catalyze the saccharification of the starch composition to glucose wherein the AfAmyl or variant thereof is dosed at 17%-50% the dose of AkAA, to reduce the same quantity of residual starch under the same conditions, and wherein the saccharification results in 2%-11% less residual starch compared to a saccharification carried out by said isoamylase and AkAA under the same conditions.

14. The method of claim 1, further comprising adding glucoamylase, hexokinase, xylanase, glucose isomerase, xylose isomerase, phosphatase, phytase, protease, pullulanase, β-amylase, α-amylase, protease, cellulase, hemicellulase, lipase, cutinase, trehalase, redox enzyme, esterase, transferase, pectinase, alpha-glucosidase, beta-glucosidase, lyase, hydrolase, branching enzyme, or a combination thereof, to said starch composition.

15. The method of claim 1, wherein said isolated AfAmyl or a variant thereof is expressed and secreted by a host cell.

16. The method of claim 15, wherein said host cell further expresses and secretes said isoamylase.

17. The method of claim 15, wherein said composition comprising starch is contacted with said host cell.

18. The method of claim 15, wherein said host cell further expresses and secretes a glucoamylase.

19. The method of claim 15, wherein the host cell is capable of fermenting the glucose composition.

* * * * *

SEQUENCE LISTING

<160> NUMBER OF SEQ ID NOS: 17

<210> SEQ ID NO 1
<211> LENGTH: 630
<212> TYPE: PRT
<213> ORGANISM: Aspergillus fumigatus Af293
<220> FEATURE:
<221> NAME/KEY: misc_feature
<222> LOCATION: (1)..(630)
<223> OTHER INFORMATION: Protein sequence of wild-type AfAmy1 (full length, w/ signal peptide)

-continued

<400> SEQUENCE: 1

Met Lys Trp Ile Ala Gln Leu Phe Pro Leu Ser Leu Cys Ser Ser Leu
1               5                   10                  15

Leu Gly Gln Ala Ala His Ala Leu Thr Pro Ala Glu Trp Arg Ser Gln
            20                  25                  30

Ser Ile Tyr Phe Leu Leu Thr Asp Arg Phe Gly Arg Glu Asp Asn Ser
        35                  40                  45

Thr Thr Ala Ala Cys Asp Val Thr Gln Arg Leu Tyr Cys Gly Gly Ser
    50                  55                  60

Trp Gln Gly Ile Ile Asn His Leu Asp Tyr Ile Gln Gly Met Gly Phe
65                  70                  75                  80

Thr Ala Ile Trp Ile Thr Pro Val Thr Glu Gln Phe Tyr Glu Asn Thr
                85                  90                  95

Gly Asp Gly Thr Ser Tyr His Gly Tyr Trp Gln Gln Asn Ile His Glu
            100                 105                 110

Val Asn Ala Asn Tyr Gly Thr Ala Gln Asp Leu Arg Asp Leu Ala Asn
        115                 120                 125

Ala Leu His Ala Arg Gly Met Tyr Leu Met Val Asp Val Val Ala Asn
    130                 135                 140

His Met Gly Tyr Asn Gly Ala Gly Asn Ser Val Asn Tyr Gly Val Phe
145                 150                 155                 160

Thr Pro Phe Asp Ser Ala Thr Tyr Phe His Pro Tyr Cys Leu Ile Thr
                165                 170                 175

Asp Tyr Asn Asn Gln Thr Ala Val Glu Asp Cys Trp Leu Gly Asp Thr
            180                 185                 190

Thr Val Ser Leu Pro Asp Leu Asp Thr Thr Ser Thr Ala Val Arg Ser
        195                 200                 205

Ile Trp Tyr Asp Trp Val Lys Gly Leu Val Ala Asn Tyr Ser Ile Asp
    210                 215                 220

Gly Leu Arg Ile Asp Thr Val Lys His Val Glu Lys Asp Phe Trp Pro
225                 230                 235                 240

Gly Tyr Asn Asp Ala Ala Gly Val Tyr Cys Val Gly Glu Val Phe Ser
                245                 250                 255

Gly Asp Pro Gln Tyr Thr Cys Pro Tyr Gln Asn Tyr Leu Asp Gly Val
            260                 265                 270

Leu Asn Tyr Pro Ile Tyr Tyr Gln Leu Leu Tyr Ala Phe Gln Ser Thr
        275                 280                 285

Ser Gly Ser Ile Ser Asn Leu Tyr Asn Met Ile Ser Ser Val Ala Ser
    290                 295                 300

Asp Cys Ala Asp Pro Thr Leu Leu Gly Asn Phe Ile Glu Asn His Asp
305                 310                 315                 320

Asn Pro Arg Phe Ala Ser Tyr Thr Ser Asp Tyr Ser Gln Ala Lys Asn
                325                 330                 335

Val Ile Ser Phe Met Phe Phe Ser Asp Gly Ile Pro Ile Val Tyr Ala
            340                 345                 350

Gly Gln Glu Gln His Tyr Ser Gly Gly Ala Asp Pro Ala Asn Arg Glu
        355                 360                 365

Ala Val Trp Leu Ser Gly Tyr Ser Thr Ser Ala Thr Leu Tyr Ser Trp
    370                 375                 380

Ile Ala Ser Thr Asn Lys Ile Arg Lys Leu Ala Ile Ser Lys Asp Ser
385                 390                 395                 400

Ala Tyr Ile Thr Ser Lys Asn Asn Pro Phe Tyr Tyr Asp Ser Asn Thr

-continued

```
                405                 410                 415

Leu Ala Met Arg Lys Gly Ser Val Ala Gly Ser Gln Val Ile Thr Val
            420                 425                 430

Leu Ser Asn Lys Gly Ser Ser Gly Ser Ser Tyr Thr Leu Ser Leu Ser
        435                 440                 445

Gly Thr Gly Tyr Ser Ala Gly Ala Thr Leu Val Glu Met Tyr Thr Cys
    450                 455                 460

Thr Thr Leu Thr Val Asp Ser Ser Gly Asn Leu Ala Val Pro Met Val
465                 470                 475                 480

Ser Gly Leu Pro Arg Val Phe Val Pro Ser Ser Trp Val Ser Gly Ser
                485                 490                 495

Gly Leu Cys Gly Asp Ser Ile Ser Thr Thr Ala Thr Ala Pro Ser Ala
            500                 505                 510

Thr Thr Ser Ala Thr Ala Thr Arg Thr Ala Cys Ala Ala Ala Thr Ala
        515                 520                 525

Ile Pro Ile Leu Phe Glu Glu Leu Val Thr Thr Thr Tyr Gly Glu Ser
    530                 535                 540

Ile Tyr Leu Thr Gly Ser Ile Ser Gln Leu Gly Asn Trp Asp Thr Ser
545                 550                 555                 560

Ser Ala Ile Ala Leu Ser Ala Ser Lys Tyr Thr Ser Ser Asn Pro Glu
                565                 570                 575

Trp Tyr Val Thr Val Thr Leu Pro Val Gly Thr Ser Phe Glu Tyr Lys
            580                 585                 590

Phe Val Lys Lys Gly Ser Asp Gly Ser Ile Ala Trp Glu Ser Asp Pro
        595                 600                 605

Asn Arg Ser Tyr Thr Val Pro Thr Gly Cys Ala Gly Thr Thr Val Thr
    610                 615                 620

Val Ser Asp Thr Trp Arg
625                 630
```

<210> SEQ ID NO 2
<211> LENGTH: 2250
<212> TYPE: DNA
<213> ORGANISM: Aspergillus fumigatus Af293
<220> FEATURE:
<221> NAME/KEY: misc_feature
<222> LOCATION: (1)..(2250)
<223> OTHER INFORMATION: Nucleotide sequence of the AfAmy1 gene (genomic sequence, w/ introns)

<400> SEQUENCE: 2

```
atgaagtgga tcgcgcagct cttcccgttg tccctgtgct cgtccctgct cggacaggct     60

gcccatgctc tgaccccagc cgaatggcgc agtcaatcga tctatttcct cctgaccgat    120

cggttcggcc gagaagacaa ttccacgact gctgcctgcg atgtcacgca acgagtgtgt    180

ccccctatcg ttcttgatcg agctcatgct aacatttgca gctgtattgc ggcgggagct    240

ggcaggggat catcaatcat gtacgactgt cccatatcgc gcggtcgaaa ctaacaatgt    300

cagctcgact acattcaagg catgggattt actgccatat ggatcacccc cgtaactgag    360

cagttctatg agaacaccgg cgatggtact tcgtaccatg gatactggca gcagaatatg    420

tgagttctct ttggccgcgg tgattcatac taatcgacga agccacgagg tcaatgccaa    480

ttatggaacg gcacaagatc ttagagatct ggccaacgct ctgcacgcgc gtggcatgta    540

cttgatggtc gatgtggtcg ccaaccatat ggtacgccgt cttctcgagt tgtacattat    600

aatctgactg gttaagggct acaacggagc gggaaactcg gtcaactacg gtgtcttcac    660
```

```
tccgtttgat tccgctacct atttccaccc atactgtctc atcaccgact acaacaacca    720

aacagctgtg gaggactgct ggctgggaga tactactgtc tcgctacccg atctcgacac    780

gaccagcacg gcagtgcgaa gcatctggta tgattgggtg aagggattgg ttgccaacta    840

ctccagtcag tgagagccgc atccgagcgt gaatgatact gaccgagata gtcgacggcc    900

tgcgcatcga cacggtgaag catgtcgaga aagacttctg gcccggctac aatgacgctg    960

ctggcgtcta ctgtgtcggt gaagtctttt cgggtgatcc acaatatacc tgtccatacc   1020

agaattacct ggatggtgta ctcaactacc ccatgtacgc attatgattt ccgtacggat   1080

ttgatcctga cgagagcaga tactatcaac ttctctacgc gttccaatcg accagcggca   1140

gcatcagcaa tctgtacaac atgatcagct ccgttgcgtc tgactgtgcg gatcccactt   1200

tgctcggcaa ctttatcgag aaccatgata accccccgatt tgcctcgtaa gaccgtgcct   1260

ccgttccctg aatgcaacta acctccccag ctatacgagc gactattcgc aagccaagaa   1320

cgtcatctcc ttcatgttct tctccgacgg catccccatt gtctacgccg gacaggagca   1380

gcactacagc ggcggtgctg accctgccaa ccgcgaggct gtctggctgt ctggatactc   1440

gaccagcgct acgctgtaca gctggattgc ctctaccaac aagattcgca agctagcgat   1500

ttccaaagac tcagcctaca taacatccaa ggtatttccg gtcacgtctt cgcattccac   1560

cgctaacatc gatagaacaa cccgttctac tatgattcca atactctcgc tatgcgcaag   1620

ggctcagtcg ctggctctca agtcattacc gtcctcagta acaagggatc ctcgggcagt   1680

tcctacaccc tctctctcag cggcacgggc tactccgccg gcgccaccct tgtcgagatg   1740

tatacatgca ctactctcac cgtggactcg agcggaaatc tcgccgtgcc aatggtatcc   1800

ggcttgccca gagttttcgt gccctcgtca tgggtcagtg ggagtggcct ctgcggcgac   1860

tctatctcca ccacggcgac cgcccccagt gccaccacga gcgcaacagc gacaagaaca   1920

gcatgcgcag ctgccacagc cattccgatt ctcttcgagg agctcgtgac aactacctac   1980

ggcgagtcca tctacctgac cggctcgatc agccaactcg ggaactggga cacgagttct   2040

gcgattgctc tgtcggcgag taaatacacc tcgtcgaacc ctgagtggta tgtcaccgtg   2100

accctgcctg ttggcacctc atttgagtac aaattcgtca agaaggggtc ggatgggagc   2160

atcgcgtggg aaagtgatcc gaaccggtcg tatacggtgc cgactgggtg tgcgggaacg   2220

accgtgacgg tgtctgatac gtggagatga                                    2250


<210> SEQ ID NO 3
<211> LENGTH: 1893
<212> TYPE: DNA
<213> ORGANISM: Aspergillus fumigatus Af293
<220> FEATURE:
<221> NAME/KEY: misc_feature
<222> LOCATION: (1)..(1893)
<223> OTHER INFORMATION: Coding sequence of the AfAmy1 gene (cDNA
      sequence, w/o introns)

<400> SEQUENCE: 3

atgaagtgga tcgcgcagct cttcccgttg tccctgtgct cgtccctgct cggacaggct     60

gcccatgctc tgaccccagc cgaatggcgc agtcaatcga tctatttcct cctgaccgat    120

cggttcggcc gagaagacaa ttccacgact gctgcctgcg atgtcacgca acgactgtat    180

tgcggcggga gctggcaggg gatcatcaat catctcgact acattcaagg catgggattt    240

actgccatat ggatcacccc cgtaactgag cagttctatg agaacaccgg cgatggtact    300

tcgtaccatg gatactggca gcagaatatc cacgaggtca atgccaatta tggaacggca    360
```

caagatctta gagatctggc caacgctctg cacgcgcgtg gcatgtactt gatggtcgat 420
gtggtcgcca accatatggg ctacaacgga gcgggaaact cggtcaacta cggtgtcttc 480
actccgtttg attccgctac ctatttccac ccatactgtc tcatcaccga ctacaacaac 540
caaacagctg tggaggactg ctggctggga gatactactg tctcgctacc cgatctcgac 600
acgaccagca cggcagtgcg aagcatctgg tatgattggg tgaagggatt ggttgccaac 660
tactccatcg acggcctgcg catcgacacg gtgaagcatg tcgagaaaga cttctggccc 720
ggctacaatg acgctgctgg cgtctactgt gtcggtgaag tcttttcggg tgatccacaa 780
tatacctgtc cataccagaa ttacctggat ggtgtactca actaccccat atactatcaa 840
cttctctacg cgttccaatc gaccagcggc agcatcagca atctgtacaa catgatcagc 900
tccgttgcgt ctgactgtgc ggatcccact ttgctcggca actttatcga gaaccatgat 960
aacccccgat ttgcctccta tacgagcgac tattcgcaag ccaagaacgt catctccttc 1020
atgttcttct ccgacggcat ccccattgtc tacgccggac aggagcagca ctacagcggc 1080
ggtgctgacc ctgccaaccg cgaggctgtc tggctgtctg gatactcgac cagcgctacg 1140
ctgtacagct ggattgcctc taccaacaag attcgcaagc tagcgatttc caaagactca 1200
gcctacataa catccaagaa caacccgttc tactatgatt ccaatactct cgctatgcgc 1260
aagggctcag tcgctggctc tcaagtcatt accgtcctca gtaacaaggg atcctcgggc 1320
agttcctaca ccctctctct cagcggcacg ggctactccg ccggcgccac ccttgtcgag 1380
atgtatacat gcactactct caccgtggac tcgagcggaa atctcgccgt gccaatggta 1440
tccggcttgc ccagagtttt cgtgccctcg tcatgggtca gtgggagtgg cctctgcggc 1500
gactctatct ccaccacggc gaccgccccc agtgccacca cgagcgcaac agcgacaaga 1560
acagcatgcg cagctgccac agccattccg attctcttcg aggagctcgt gacaactacc 1620
tacggcgagt ccatctacct gaccggctcg atcagccaac tcgggaactg ggacacgagt 1680
tctgcgattg ctctgtcggc gagtaaatac acctcgtcga accctgagtg gtatgtcacc 1740
gtgaccctgc ctgttggcac ctcatttgag tacaaattcg tcaagaaggg gtcggatggg 1800
agcatcgcgt gggaaagtga tccgaaccgg tcgtatacgg tgccgactgg gtgtgcggga 1860
acgaccgtga cggtgtctga tacgtggaga tga 1893

<210> SEQ ID NO 4
<211> LENGTH: 23
<212> TYPE: PRT
<213> ORGANISM: Aspergillus fumigatus Af293
<220> FEATURE:
<221> NAME/KEY: misc_feature
<222> LOCATION: (1)..(23)
<223> OTHER INFORMATION: Amino acid sequence of the AfAmy1 signal peptide

<400> SEQUENCE: 4

Met Lys Trp Ile Ala Gln Leu Phe Pro Leu Ser Leu Cys Ser Ser Leu
1 5 10 15

Leu Gly Gln Ala Ala His Ala
20

<210> SEQ ID NO 5
<211> LENGTH: 632
<212> TYPE: PRT
<213> ORGANISM: Neosartorya fischeri NRRL 181
<220> FEATURE:
<221> NAME/KEY: misc_feature
<222> LOCATION: (1)..(632)

```
<223> OTHER INFORMATION: Putative alpha-amylase from Neosartorya
      fischeri NRRL 181

<400> SEQUENCE: 5

Met Lys Trp Ile Ser Pro Leu Leu Pro Leu Ser Leu Ser Leu Cys Leu
1               5                   10                  15

Leu Gly Gln Ala Ala His Ala Leu Thr Pro Ala Glu Trp Arg Ser Gln
            20                  25                  30

Ser Ile Tyr Phe Leu Leu Thr Asp Arg Phe Gly Arg Glu Asp Asn Ser
        35                  40                  45

Thr Thr Ala Ala Cys Asp Val Thr Gln Arg Leu Tyr Cys Gly Gly Ser
    50                  55                  60

Trp Gln Gly Ile Ile Asn His Leu Asp Tyr Ile Gln Gly Met Gly Phe
65                  70                  75                  80

Thr Ala Ile Trp Ile Thr Pro Val Thr Gln Gln Phe Tyr Glu Asn Thr
                85                  90                  95

Gly Asp Gly Thr Ser Tyr His Gly Tyr Trp Gln Gln Asn Ile Tyr Glu
            100                 105                 110

Val Asn Ser Asn Tyr Gly Thr Ala Gln Asp Leu Arg Lys Leu Ala Asp
        115                 120                 125

Ala Leu His Ala Arg Gly Met Tyr Leu Met Val Asp Val Val Ala Asn
    130                 135                 140

His Met Gly Tyr Asp Gly Ala Gly Asn Ser Val Asp Tyr Ser Val Phe
145                 150                 155                 160

Thr Pro Phe Asp Ser Ser Thr Tyr Phe His Thr Tyr Cys Leu Ile Ser
                165                 170                 175

Asp Tyr Asn Asn Gln Asn Asn Val Glu Asp Cys Trp Leu Gly Asp Thr
            180                 185                 190

Thr Val Ser Leu Pro Asp Leu Asp Thr Thr Asn Thr Ala Val Arg Thr
        195                 200                 205

Ile Trp Tyr Asp Trp Val Lys Gly Leu Val Ala Asn Tyr Ser Ile Asp
    210                 215                 220

Gly Leu Arg Ile Asp Thr Val Lys His Val Glu Lys Asp Phe Trp Pro
225                 230                 235                 240

Asp Tyr Asn Asp Ala Ala Gly Val Tyr Cys Val Gly Glu Val Phe Ser
                245                 250                 255

Gly Asp Pro Ser Tyr Thr Cys Pro Tyr Gln Asn Tyr Met Asp Gly Val
            260                 265                 270

Leu Asn Tyr Pro Ile Tyr Tyr Gln Leu Leu Tyr Ala Phe Gln Ser Thr
        275                 280                 285

Ser Gly Ser Ile Ser Asn Leu Tyr Asn Met Ile Ser Ser Val Asp Ser
    290                 295                 300

Asp Cys Ala Asp Pro Thr Leu Leu Gly Asn Phe Ile Glu Asn His Asp
305                 310                 315                 320

Asn Pro Arg Phe Ala Ser Tyr Thr Ser Asp Tyr Ser Gln Ala Lys Asn
                325                 330                 335

Val Ile Ser Phe Met Phe Phe Ser Asp Gly Ile Pro Ile Val Tyr Ala
            340                 345                 350

Gly Gln Glu Gln His Tyr Ser Gly Gly Ala Asp Pro Ala Asn Arg Glu
        355                 360                 365

Ala Val Trp Leu Ser Gly Tyr Ser Thr Ser Ala Thr Leu Tyr Ser Trp
    370                 375                 380

Ile Ala Ser Thr Asn Lys Ile Arg Lys Leu Ala Ile Ser Lys Asp Ser
385                 390                 395                 400
```

```
Ala Tyr Ile Thr Ser Lys Asn Asn Pro Phe Tyr Tyr Asp Ser Asn Thr
                405                 410                 415

Leu Ala Met Arg Lys Gly Ser Val Ala Gly Ser Gln Val Ile Thr Val
            420                 425                 430

Leu Ser Asn Lys Gly Ser Ser Gly Ser Ser Tyr Thr Leu Ser Leu Ser
        435                 440                 445

Gly Thr Gly Tyr Ser Ala Gly Ala Thr Leu Val Glu Met Tyr Thr Cys
    450                 455                 460

Thr Thr Leu Thr Val Asp Ser Ser Gly Asn Leu Ala Val Pro Met Ala
465                 470                 475                 480

Ser Gly Leu Pro Arg Val Leu Val Pro Ser Ser Trp Val Ser Gly Ser
                485                 490                 495

Gly Leu Cys Gly Asp Ser Ile Ser Thr Ile Ala Thr Thr Thr Thr Ser
            500                 505                 510

Thr Thr Lys Thr Thr Thr Val Ala Thr Thr Thr Ala Cys Ala Ser Ala
        515                 520                 525

Thr Ala Leu Pro Ile Leu Phe Glu Glu Leu Val Thr Thr Thr Tyr Gly
    530                 535                 540

Glu Thr Ile Tyr Leu Thr Gly Ser Ile Ser Gln Leu Gly Asn Trp Asp
545                 550                 555                 560

Thr Ser Ser Ala Ile Ala Leu Ser Ala Ser Lys Tyr Thr Ser Ser Asn
                565                 570                 575

Pro Glu Trp Tyr Ala Thr Val Thr Leu Pro Val Gly Thr Ser Phe Gln
            580                 585                 590

Tyr Lys Phe Phe Lys Lys Glu Ser Asp Gly Ser Ile Val Trp Glu Ser
        595                 600                 605

Asp Pro Asn Arg Ser Tyr Thr Val Pro Ala Gly Cys Ala Gly Thr Thr
    610                 615                 620

Val Thr Val Ser Asp Thr Trp Arg
625                 630


<210> SEQ ID NO 6
<211> LENGTH: 607
<212> TYPE: PRT
<213> ORGANISM: Aspergillus terreus NIH2624
<220> FEATURE:
<221> NAME/KEY: misc_feature
<222> LOCATION: (1)..(607)
<223> OTHER INFORMATION: Alpha-amylase precursor from Aspergillus
      terreus NIH2624

<400> SEQUENCE: 6

Met Lys Trp Thr Ser Ser Leu Leu Leu Leu Leu Ser Val Ile Gly Gln
1               5                   10                  15

Ala Thr His Ala Leu Thr Pro Ala Glu Trp Arg Ser Gln Ser Ile Tyr
            20                  25                  30

Phe Leu Leu Thr Asp Arg Phe Gly Arg Thr Asp Asn Ser Thr Thr Ala
        35                  40                  45

Ala Cys Asp Thr Ser Asp Arg Val Tyr Cys Gly Gly Ser Trp Gln Gly
    50                  55                  60

Ile Ile Asn Gln Leu Asp Tyr Ile Gln Gly Met Gly Phe Thr Ala Ile
65                  70                  75                  80

Trp Ile Thr Pro Val Thr Gly Gln Phe Tyr Glu Asn Thr Gly Asp Gly
                85                  90                  95

Thr Ser Tyr His Gly Tyr Trp Gln Gln Asp Ile Tyr Asp Leu Asn Tyr
            100                 105                 110
```

-continued

```
Asn Tyr Gly Thr Ala Gln Asp Leu Lys Asn Leu Ala Asn Ala Leu His
        115                 120                 125

Glu Arg Gly Met Tyr Leu Met Val Asp Val Val Ala Asn His Met Gly
    130                 135                 140

Tyr Asp Gly Ala Gly Asn Thr Val Asp Tyr Ser Val Phe Asn Pro Phe
145                 150                 155                 160

Ser Ser Ser Ser Tyr Phe His Pro Tyr Cys Leu Ile Ser Asn Tyr Asp
                165                 170                 175

Asn Gln Thr Asn Val Glu Asp Cys Trp Leu Gly Asp Thr Thr Val Ser
            180                 185                 190

Leu Pro Asp Leu Asp Thr Thr Ser Thr Ala Val Arg Asn Ile Trp Tyr
        195                 200                 205

Asp Trp Val Ala Asp Leu Val Ala Asn Tyr Ser Ile Asp Gly Leu Arg
    210                 215                 220

Val Asp Thr Val Lys His Val Glu Lys Asp Phe Trp Pro Gly Tyr Asn
225                 230                 235                 240

Ser Ala Ala Gly Val Tyr Cys Val Gly Glu Val Tyr Ser Gly Asp Pro
                245                 250                 255

Ala Tyr Thr Cys Pro Tyr Gln Asn Tyr Met Asp Gly Val Leu Asn Tyr
            260                 265                 270

Pro Ile Tyr Tyr Gln Leu Leu Tyr Ala Phe Glu Ser Ser Ser Gly Ser
        275                 280                 285

Ile Ser Asp Leu Tyr Asn Met Ile Ser Ser Val Ala Ser Ser Cys Lys
    290                 295                 300

Asp Pro Thr Leu Leu Gly Asn Phe Ile Glu Asn His Asp Asn Pro Arg
305                 310                 315                 320

Phe Ala Ser Tyr Thr Ser Asp Tyr Ser Gln Ala Lys Asn Val Ile Thr
                325                 330                 335

Phe Ile Phe Leu Ser Asp Gly Ile Pro Ile Val Tyr Ala Gly Gln Glu
            340                 345                 350

Gln His Tyr Ser Gly Gly Ser Asp Pro Ala Asn Arg Glu Ala Thr Trp
        355                 360                 365

Leu Ser Gly Tyr Ser Thr Ser Ala Thr Leu Tyr Thr Trp Ile Ala Thr
    370                 375                 380

Thr Asn Gln Ile Arg Ser Leu Ala Ile Ser Lys Asp Ala Gly Tyr Val
385                 390                 395                 400

Gln Ala Lys Asn Asn Pro Phe Tyr Ser Asp Ser Asn Thr Ile Ala Met
                405                 410                 415

Arg Lys Gly Thr Thr Ala Gly Ala Gln Val Ile Thr Val Leu Ser Asn
            420                 425                 430

Lys Gly Ala Ser Gly Ser Ser Tyr Thr Leu Ser Leu Ser Gly Thr Gly
        435                 440                 445

Tyr Ser Ala Gly Ala Thr Leu Val Glu Thr Tyr Thr Cys Thr Thr Val
    450                 455                 460

Thr Val Asp Ser Ser Gly Asn Leu Pro Val Pro Met Thr Ser Gly Leu
465                 470                 475                 480

Pro Arg Val Phe Val Pro Ser Ser Trp Val Asn Gly Ser Ala Leu Cys
                485                 490                 495

Asn Thr Glu Cys Thr Ala Ala Thr Ser Ile Ser Val Leu Phe Glu Glu
            500                 505                 510

Leu Val Thr Thr Thr Tyr Gly Glu Asn Ile Tyr Leu Ser Gly Ser Ile
        515                 520                 525
```

```
Ser Gln Leu Gly Ser Trp Asn Thr Ala Ser Ala Val Ala Leu Ser Ala
    530                 535                 540

Ser Gln Tyr Thr Ser Ser Asn Pro Glu Trp Tyr Val Ser Val Thr Leu
545                 550                 555                 560

Pro Val Gly Thr Ser Phe Gln Tyr Lys Phe Ile Lys Lys Gly Ser Asp
                565                 570                 575

Gly Ser Val Val Trp Glu Ser Asp Pro Asn Arg Ser Tyr Thr Val Pro
            580                 585                 590

Ala Gly Cys Glu Gly Ala Thr Val Thr Val Ala Asp Thr Trp Arg
        595                 600                 605


<210> SEQ ID NO 7
<211> LENGTH: 630
<212> TYPE: PRT
<213> ORGANISM: Ophiostoma floccosum
<220> FEATURE:
<221> NAME/KEY: misc_feature
<222> LOCATION: (1)..(630)
<223> OTHER INFORMATION: Alpha-amylase AMYI from Ophiostoma floccosum

<400> SEQUENCE: 7

Met Lys Leu Ser Ser Leu Leu Pro Leu Ala Phe Leu Gly Gln Ala Val
1               5                   10                  15

Asn Ala Leu Ser Pro Ala Glu Trp Arg Lys Gln Ser Ile Tyr Phe Leu
            20                  25                  30

Leu Thr Asp Arg Phe Gly Arg Thr Asp Asn Ser Thr Ser Ala Thr Cys
        35                  40                  45

Asn Thr Gly Asp Arg Ala Tyr Cys Gly Gly Ser Trp Gln Gly Val Ile
    50                  55                  60

Asn His Leu Asp Tyr Ile Gln Gly Met Gly Phe Thr Ala Ile Trp Ile
65                  70                  75                  80

Thr Pro Val Thr Gly Gln Phe Tyr Glu Ser Thr Gly Asp Gly Thr Ser
                85                  90                  95

Tyr His Gly Tyr Trp Gln Gln Asp Ile Tyr Ser Leu Asn Ser His Leu
            100                 105                 110

Gly Asp Gln Asn Asp Leu Lys Ala Leu Ser Ala Ala Leu His Ala Arg
        115                 120                 125

Gly Met Tyr Leu Met Val Asp Val Val Ala Asn His Met Gly Tyr Asp
    130                 135                 140

Gly Ala Gly Ser Asn Val Asp Tyr Ser Val Phe Asp Ala Phe Pro Ser
145                 150                 155                 160

Ser Ser Tyr Phe His Ser Tyr Cys Glu Ile Ser Asn Tyr Asp Asp Gln
                165                 170                 175

Ser Asn Val Glu Asp Cys Trp Leu Gly Asp Thr Thr Val Ser Leu Pro
            180                 185                 190

Asp Leu Asn Thr Glu Leu Thr Ser Val Arg Ser Ile Trp Asn Ser Trp
        195                 200                 205

Val Ala Gly Leu Val Ala Asn Tyr Ser Ile Asp Gly Leu Arg Ile Asp
    210                 215                 220

Thr Val Lys His Val Glu Thr Ser Phe Trp Pro Gly Tyr Asn Asp Ala
225                 230                 235                 240

Ala Gly Val Tyr Cys Val Gly Glu Val Phe Asp Gly Asp Pro Ala Tyr
                245                 250                 255

Thr Cys Ala Tyr Gln Asn Tyr Met Asp Gly Val Leu Asn Tyr Pro Ile
            260                 265                 270

Tyr Tyr Gln Leu Leu Ser Ala Phe Glu Ser Thr Ser Gly Ser Ile Ser
```

-continued

```
        275                 280                 285

Asn Leu Tyr Asn Met Ile Lys Ser Val Ala Ser Asp Cys Ala Asp Pro
    290                 295                 300

Thr Leu Leu Gly Asn Phe Ile Glu Asn His Asp Asn Pro Arg Phe Ala
305                 310                 315                 320

Ser Tyr Thr Ser Asp Tyr Ser Leu Ala Gln Asn Ala Ile Ser Phe Leu
                325                 330                 335

Phe Phe Ser Asp Gly Ile Pro Ile Val Tyr Ser Gly Gln Glu Gln His
            340                 345                 350

Tyr Ser Gly Gly Ala Asp Pro Ala Asn Arg Glu Ala Thr Trp Leu Ser
        355                 360                 365

Gly Tyr Ser Thr Thr Ala Thr Leu Tyr Lys His Ile Lys Thr Thr Asn
    370                 375                 380

Gln Ile Arg Ser Leu Ile Ile Gly Lys Asp Ser Ser Trp Ala Thr Ser
385                 390                 395                 400

Ala Asn Ser Pro Phe Tyr Gln Asp Ser Asn Thr Ile Ala Met Leu Lys
                405                 410                 415

Gly Ser Ala Ser Gly Ser Lys Val Leu Thr Val Leu Ser Asn Lys Gly
            420                 425                 430

Ala Ser Gly Ser Ser Tyr Thr Leu Ser Leu Gly Ser Thr Gly Tyr Ser
        435                 440                 445

Ser Gly Ala Ser Leu Val Glu Leu Tyr Ser Cys Thr Thr Val Thr Val
    450                 455                 460

Asp Ser Ser Gly Asn Val Pro Val Pro Met Ala Ser Gly Leu Pro Arg
465                 470                 475                 480

Val Leu Val Pro Ser Ser Trp Val Ser Gly Ser Gly Leu Cys Gly Thr
                485                 490                 495

Ala Val Thr Thr Gly Thr Ala Thr Ala Thr Gly Thr Ser Thr Lys Ala
            500                 505                 510

Thr Thr Ala Thr Ala Thr Thr Ala Thr Ser Cys Thr Ala Ala Thr Ala
        515                 520                 525

Val Ser Val Val Phe Asn Glu Leu Ala Thr Thr Thr Tyr Gly Glu Asn
    530                 535                 540

Val Tyr Ile Ile Gly Ser Thr Ser Gln Leu Gly Ser Trp Ser Thr Ala
545                 550                 555                 560

Asn Ala Ile Ala Leu Ser Ser Ser Asp Tyr Thr Ser Ser Asn Pro Leu
                565                 570                 575

Trp His Val Thr Val Ser Leu Pro Ala Gly Ser Ser Phe Thr Tyr Lys
            580                 585                 590

Phe Ile Lys Lys Glu Ser Asp Gly Thr Phe Val Trp Glu Ser Asp Pro
        595                 600                 605

Asn Arg Ser Tyr Thr Val Pro Thr Gly Cys Ser Gly Leu Ser Ala Thr
    610                 615                 620

Val Ser Ala Thr Trp Arg
625                 630


<210> SEQ ID NO 8
<211> LENGTH: 623
<212> TYPE: PRT
<213> ORGANISM: Penicillium chrysogenum Wisconsin 54-1255
<220> FEATURE:
<221> NAME/KEY: misc_feature
<222> LOCATION: (1)..(623)
<223> OTHER INFORMATION: Putative alpha-amylase from Penicillium
      chrysogenum Wisconsin 54-1255
```

<400> SEQUENCE: 8

Met Lys Lys Val Ile Phe Thr Ala Thr Ile Leu Leu Trp Gln Met Val
1 5 10 15

Met Gly Leu Thr Pro Ala Glu Trp Arg Ser Gln Ser Ile Tyr Phe Leu
20 25 30

Leu Thr Asp Arg Phe Gly Arg Thr Asp Asn Ser Val Thr Ala Asn Cys
35 40 45

Asn Val Asp Asp Arg Ala Tyr Cys Gly Gly Thr Trp Gln Gly Ile Ile
50 55 60

Asn Gln Leu Asp Tyr Ile Gln Gly Met Gly Phe Thr Ala Ile Trp Ile
65 70 75 80

Thr Pro Val Thr Lys Gln Leu Pro Gln Asp Thr Gly Tyr Gly Met Ala
85 90 95

Tyr His Gly Tyr Trp Gln Gln Asp Ile Tyr Asp Val Asn Asp His His
100 105 110

Gly Thr Ser Asp Asp Leu Leu Ala Leu Ser Lys Ala Leu His Ala Arg
115 120 125

Gly Met Tyr Leu Met Val Asp Val Val Ala Asn His Met Gly Tyr Ala
130 135 140

Gly Ala Gly Asn Thr Val Asp Tyr Ser Val Phe Thr Pro Phe Ser Ser
145 150 155 160

Ser Ser Tyr Phe His Pro Tyr Cys Leu Ile Ser Asn Tyr Asn Asp Gln
165 170 175

Ser Asn Val Glu Asn Cys Trp Leu Gly Asp Thr Thr Val Ser Leu Pro
180 185 190

Asp Leu Asp Thr Thr Gln Asn Ser Val Gln Thr Ile Trp Asn Asp Trp
195 200 205

Ile Ala Asp Leu Val Thr Lys Tyr Ser Ile Asp Gly Leu Arg Ile Asp
210 215 220

Thr Val Lys His Val Gln Lys Ser Phe Trp Pro Gly Phe Asn Asp Ala
225 230 235 240

Ala Gly Val Tyr Ala Val Gly Glu Ile Phe Asp Gly Asn Pro Ala Tyr
245 250 255

Thr Cys Asp Tyr Gln Asn Tyr Met Asp Gly Val Leu Asn Tyr Pro Ile
260 265 270

Tyr Tyr Pro Leu Leu Arg Ala Phe Gln Ser Ser Ser Gly Ser Ile Ser
275 280 285

Asp Leu Tyr Asn Met Val Gly Thr Val Ala Ser Ser Cys Ala Asp Ser
290 295 300

Thr Leu Leu Gly Asn Phe Ile Glu Asn His Asp Asn Pro Arg Phe Pro
305 310 315 320

Ser Tyr Thr Ser Asp Tyr Ser Gln Ala Lys Asn Val Ile Ser Phe Leu
325 330 335

Phe Leu Ser Asp Gly Ile Pro Ile Val Tyr Ala Gly Gln Glu Gln His
340 345 350

Tyr Ser Gly Gly His Asp Pro Ala Asn Arg Glu Ala Val Trp Leu Ser
355 360 365

Gly Tyr Ser Thr Thr Ala Glu Leu Tyr Gln His Ile Ala Thr Thr Asn
370 375 380

Lys Ile Arg Lys Ala Ala Val Ala Ala Asp Ser Ser Tyr Ile Thr Ser
385 390 395 400

Lys Asn Val Pro Phe Tyr Gln Asp Ser His Thr Leu Ala Met Lys Lys
405 410 415

```
Gly Ser Gly Ser Ser Pro Val Ile Thr Val Leu Ser Asn Ala Gly Ser
            420                 425                 430

Ser Gly Ser Ser Tyr Thr Leu Tyr Leu Gly Gly Ser Gly Tyr Ser Ser
        435                 440                 445

Gly Thr Lys Leu Met Glu Met His Thr Cys Thr Ser Ile Thr Val Asp
    450                 455                 460

Ser Ser Gly Lys Ile Ala Val Pro Met Val Ser Gly Leu Pro Arg Val
465                 470                 475                 480

Leu Ile Pro Ala Ser Ser Val Ser Asn Ser Gly Leu Cys Gly Ser Ser
                485                 490                 495

Val Pro Ser Ala Thr Ala Thr Gln Thr Thr Thr Ala Thr Thr Thr Gly
            500                 505                 510

Ala Gly Cys Thr Gln Ala Thr Ala Leu Pro Val Leu Phe Lys Glu Leu
        515                 520                 525

Val Thr Thr Val Tyr Gly Gln Asp Ile Tyr Ile Ser Gly Ser Ile Ser
    530                 535                 540

Gln Leu Gly Asn Trp Asp Thr Ser Gln Ala Ile Ala Leu Ser Ser Ser
545                 550                 555                 560

Ser Tyr Thr Ala Ser Asn Pro Leu Trp Gln Thr Thr Ile Thr Leu Pro
                565                 570                 575

Val Gly Thr Thr Phe Gln Tyr Lys Phe Leu Lys Lys Thr Thr Gly Ser
            580                 585                 590

Ser Thr Val Thr Trp Glu Ser Asp Pro Asn Arg Ser Tyr Thr Val Pro
        595                 600                 605

Thr Gly Cys Thr Gly Ala Thr Ala Thr Val Ala Ala Ser Trp Lys
    610                 615                 620


<210> SEQ ID NO 9
<211> LENGTH: 631
<212> TYPE: PRT
<213> ORGANISM: Aspergillus clavatus NRRL 1
<220> FEATURE:
<221> NAME/KEY: misc_feature
<222> LOCATION: (1)..(631)
<223> OTHER INFORMATION: Putative alpha-amylase from Aspergillus
      clavatus NRRL 1

<400> SEQUENCE: 9

Met Lys Trp Ser Thr Val Pro Leu Ser Leu Ser Leu Leu Gly Gln Ala
1               5                   10                  15

Val Asn Ala Leu Thr Pro Ala Glu Trp Arg Ser Gln Ser Ile Tyr Phe
            20                  25                  30

Leu Leu Thr Asp Arg Phe Gly Arg Asp Asp Arg Ser Thr Ser Ala Pro
        35                  40                  45

Cys Asp Thr Asn Gln Arg Met Tyr Cys Gly Gly Thr Trp Gln Gly Ile
    50                  55                  60

Ile Asn Gln Leu Asp Tyr Ile Gln Gly Met Gly Phe Thr Ala Ile Trp
65                  70                  75                  80

Ile Thr Pro Val Thr Glu Gln Phe Tyr Glu Ser Thr Gly Asp Gly Ser
                85                  90                  95

Ser Tyr His Gly Tyr Trp Gln Gln Asn Ile Asn Glu Val Asn Arg Lys
            100                 105                 110

His Gly Thr Lys Gln Asp Leu Lys Asn Leu Ala Asp Ala Leu His Ala
        115                 120                 125

Arg Gly Met Tyr Leu Met Val Asp Val Val Ala Asn His Met Gly Tyr
    130                 135                 140
```

-continued

```
Arg Gly Ser Gly Gln Asn Val Asp Phe Asn Thr Phe His Pro Phe Asn
145                 150                 155                 160

Arg Ala Glu His Tyr Asn Ser Phe Cys Thr Ile Thr Asp Tyr Asn Asn
                165                 170                 175

Gln Asn Ser Val Glu Lys Cys Trp Leu Gly Ser Asn Thr Val Ser Leu
            180                 185                 190

Pro Asp Leu Ala Thr Thr His Pro Trp Val Arg Ser Thr Trp Tyr Asp
        195                 200                 205

Trp Val Arg Asp Leu Val Lys Asp Tyr Ser Ile Asp Gly Leu Arg Ile
    210                 215                 220

Asp Thr Val Lys His Val Glu Lys Asp Phe Trp Arg Pro Tyr Asn Asp
225                 230                 235                 240

Ala Ala Gly Val Tyr Cys Val Gly Glu Ile Phe Ser Gly Asp Pro Gly
                245                 250                 255

Tyr Thr Cys Asp Tyr Gln Asn His Met Asp Gly Val Leu Asn Tyr Pro
            260                 265                 270

Ile Tyr Tyr Pro Leu Leu Asn Ala Phe Lys Ser Thr Ser Gly Ser Met
        275                 280                 285

Gly Asp Leu Arg Asn Met Ile Gly Thr Val Ser Asn Lys Cys Arg Asp
    290                 295                 300

Pro Thr Leu Leu Gly Asn Phe Ile Glu Asn His Asp Asn Pro Arg Phe
305                 310                 315                 320

Ala His Tyr Thr Asn Asp Ile Ser Gln Ala Lys Asn Val Leu Thr Phe
                325                 330                 335

Met Phe Leu Thr Asp Gly Ile Pro Ile Val Tyr Ala Gly Gln Glu Gln
            340                 345                 350

His Tyr Asp Gly Gly Glu Asp Pro His Asn Arg Glu Ala Thr Trp Phe
        355                 360                 365

Ser Gly Tyr Asn Lys Asn Ala Glu Leu Tyr Thr Trp Ile Ala Lys Thr
    370                 375                 380

Asn Lys Ile Arg Ser Leu Ala Val Ser Lys Asp Ser Gly Tyr Val Thr
385                 390                 395                 400

Ala Arg Asn Asn Pro Phe Tyr His Asp Thr Thr Thr Leu Ala Met Arg
                405                 410                 415

Lys Gly Ser Arg Asp Gly Ala Gln Val Ile Thr Ile Val Ser Asn Lys
            420                 425                 430

Gly Ala Ser Gly Asp Gly Tyr Thr Met Gln Leu Ser Gly His Gly Tyr
        435                 440                 445

Gly Ser Gly Ala Thr Val Met Glu Met Tyr Thr Cys Thr Pro Leu Thr
    450                 455                 460

Val Gly Gly Asn Gly Ile Ile Pro Val Pro Met Val Ser Gly Gln Pro
465                 470                 475                 480

Arg Val Leu Val Pro Ser Ser Trp Val Ala Gly Ser Gly Leu Cys Gly
                485                 490                 495

Ser Thr Gly Pro Ser Thr Thr Thr Thr Pro Ser Thr Thr Thr Thr Pro
            500                 505                 510

Ser Thr Thr Thr Ala Thr Glu Pro Gly Thr Thr Cys Thr Ala Ala Ser
        515                 520                 525

Thr Leu Pro Val Gln Phe Gln Glu Arg Val Thr Thr Asn Tyr Gly Asp
    530                 535                 540

Ser Val Phe Ile Val Gly Ser Ile Pro Gln Leu Gly Gly Trp Asp Val
545                 550                 555                 560
```

-continued

Lys Lys Ala Val Ala Leu Ser Ala Glu Lys Tyr Thr Pro Gly Asn Pro
565 570 575

Glu Trp Arg Ala Thr Ile Thr Leu Pro Val Gly Thr Lys Phe Glu Tyr
580 585 590

Lys Phe Ile Lys Lys Gln Ser Asn Gly Gln Ile Val Trp Glu Asn Asp
595 600 605

Pro Asn Arg Thr Tyr Asn Val Pro Ser Gln Cys Ala Gly Thr Val Ala
610 615 620

Thr Ala Ser Ser Ser Trp Lys
625 630

<210> SEQ ID NO 10
<211> LENGTH: 640
<212> TYPE: PRT
<213> ORGANISM: Aspergillus kawachii
<220> FEATURE:
<221> NAME/KEY: misc_feature
<222> LOCATION: (1)..(640)
<223> OTHER INFORMATION: Acid-stable alpha-amylase from Aspergillus kawachii

<400> SEQUENCE: 10

Met Arg Val Ser Thr Ser Ser Ile Ala Leu Ala Val Ser Leu Phe Gly
1 5 10 15

Lys Leu Ala Leu Gly Leu Ser Ala Ala Glu Trp Arg Thr Gln Ser Ile
20 25 30

Tyr Phe Leu Leu Thr Asp Arg Phe Gly Arg Thr Asp Asn Ser Thr Thr
35 40 45

Ala Thr Cys Asn Thr Gly Asp Gln Ile Tyr Cys Gly Gly Ser Trp Gln
50 55 60

Gly Ile Ile Asn His Leu Asp Tyr Ile Gln Gly Met Gly Phe Thr Ala
65 70 75 80

Ile Trp Ile Ser Pro Ile Thr Glu Gln Leu Pro Gln Asp Thr Ser Asp
85 90 95

Gly Glu Ala Tyr His Gly Tyr Trp Gln Gln Lys Ile Tyr Tyr Val Asn
100 105 110

Ser Asn Phe Gly Thr Ala Asp Asp Leu Lys Ser Leu Ser Asp Ala Leu
115 120 125

His Ala Arg Gly Met Tyr Leu Met Val Asp Val Val Pro Asn His Met
130 135 140

Gly Tyr Ala Gly Asn Gly Asn Asp Val Asp Tyr Ser Val Phe Asp Pro
145 150 155 160

Phe Asp Ser Ser Ser Tyr Phe His Pro Tyr Cys Leu Ile Thr Asp Trp
165 170 175

Asp Asn Leu Thr Met Val Gln Asp Cys Trp Glu Gly Asp Thr Ile Val
180 185 190

Ser Leu Pro Asp Leu Asn Thr Thr Glu Thr Ala Val Arg Thr Ile Trp
195 200 205

Tyr Asp Trp Val Ala Asp Leu Val Ser Asn Tyr Ser Val Asp Gly Leu
210 215 220

Arg Ile Asp Ser Val Glu Glu Val Glu Pro Asp Phe Phe Pro Gly Tyr
225 230 235 240

Gln Glu Ala Ala Gly Val Tyr Cys Val Gly Glu Val Asp Asn Gly Asn
245 250 255

Pro Ala Leu Asp Cys Pro Tyr Gln Lys Tyr Leu Asp Gly Val Leu Asn
260 265 270

```
Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Asp Val Pro Tyr Asn Arg Glu Ala Thr
        355                 360                 365

Trp Leu Ser Gly Tyr Asp Thr Ser Ala Glu Leu Tyr Thr Trp Ile Ala
    370                 375                 380

Thr Thr Asn Ala Ile Arg Lys Leu Ala Ile Ser Ala Asp Ser Asp Tyr
385                 390                 395                 400

Ile Thr Tyr Lys Asn Asp Pro Ile Tyr Thr Asp Ser Asn Thr Ile Ala
                405                 410                 415

Met Arg Lys Gly Thr Ser Gly Ser Gln Ile Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Asn Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Asn Thr Thr Thr Thr Thr Thr Ala Ala Thr Ser Thr
            500                 505                 510

Ser Lys Ala Thr Thr Ser Ser Ser Ser Ser Ser Ala Ala Ala Thr Thr
        515                 520                 525

Ser Ser Ser Cys Thr Ala Thr Ser Thr Thr Leu Pro Ile Thr Phe Glu
    530                 535                 540

Glu Leu Val Thr Thr Thr Tyr Gly Glu Glu Val Tyr Leu Ser Gly Ser
545                 550                 555                 560

Ile Ser Gln Leu Gly Glu Trp His Thr Ser Asp Ala Val Lys Leu Ser
                565                 570                 575

Ala Asp Asp Tyr Thr Ser Ser Asn Pro Glu Trp Ser Val Thr Val Ser
            580                 585                 590

Leu Pro Val Gly Thr Thr Phe Glu Tyr Lys Phe Ile Lys Val Asp Glu
        595                 600                 605

Gly Gly Ser Val Thr Trp Glu Ser Asp Pro Asn Arg Glu Tyr Thr Val
    610                 615                 620

Pro Glu Cys Gly Ser Gly Ser Gly Glu Thr Val Val Asp Thr Trp Arg
625                 630                 635                 640


<210> SEQ ID NO 11
<211> LENGTH: 634
<212> TYPE: PRT
<213> ORGANISM: Aspergillus awamori
<220> FEATURE:
<221> NAME/KEY: misc_feature
<222> LOCATION: (1)..(634)
<223> OTHER INFORMATION: Alpha-amylase from Aspergillus awamori
```

<400> SEQUENCE: 11

Met Arg Val Ser Thr Ser Ser Leu Ala Leu Ser Val Ser Leu Phe Gly
1               5                   10                  15

Lys Leu Ala Leu Gly Leu Ser Ala Ala Glu Trp Arg Ser Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Asp Tyr Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asp Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Asp Val Pro Tyr Asn Arg Glu Ala Thr
        355                 360                 365

Trp Leu Ser Gly Tyr Asp Thr Ser Ala Glu Leu Tyr Thr Trp Ile Ala
    370                 375                 380

Thr Thr Asn Ala Ile Arg Lys Leu Ala Ile Ser Ala Asp Ser Asp Tyr
385                 390                 395                 400

Ile Thr Tyr Ala Asn Asp Pro Ile Tyr Thr Asp Ser Asn Thr Ile Ala
                405                 410                 415

```
Met Arg Lys Gly Thr Ser Gly Ser Gln Val Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Glu Leu Ile Glu Ala Tyr Thr Cys Thr Ser Val
    450                 455                 460

Thr Val Asp Ser Asn Gly Asp Ile Pro Val Pro Met Ala Ser Gly Leu
465                 470                 475                 480

Pro Arg Val Leu Leu Pro Ala Trp Val Val Asp Ser Ser Ser Ser Leu
                485                 490                 495

Trp Gly Gly Ser Thr Thr Thr Thr Thr Ser Ser Ser Thr Ser Thr Ser
            500                 505                 510

Thr Ser Lys Ala Thr Ser Ser Ser Ser Thr Thr Thr Ser Ser Ser Cys
        515                 520                 525

Thr Ala Thr Ser Thr Thr Leu Pro Ile Thr Leu Glu Glu Leu Val Thr
    530                 535                 540

Thr Thr Tyr Gly Glu Glu Ile Tyr Leu Ser Gly Ser Ile Ser Gln Leu
545                 550                 555                 560

Gly Glu Trp Asp Thr Ser Asp Ala Val Lys Leu Ser Ala Asp Asp Tyr
                565                 570                 575

Thr Ser Ser Asn Pro Glu Trp Tyr Val Thr Val Ser Leu Pro Val Gly
            580                 585                 590

Thr Thr Phe Glu Tyr Lys Phe Ile Lys Val Glu Glu Asp Gly Ser Val
        595                 600                 605

Thr Trp Glu Ser Asp Pro Asn Arg Glu Tyr Thr Val Pro Glu Cys Gly
    610                 615                 620

Ser Gly Glu Thr Val Val Asp Thr Trp Arg
625                 630
```

<210> SEQ ID NO 12
<211> LENGTH: 33
<212> TYPE: DNA
<213> ORGANISM: Artificial Sequence
<220> FEATURE:
<223> OTHER INFORMATION: Synthetic primer

<400> SEQUENCE: 12
ccgcggccgc accatgaagt ggatcgcgca gct 33

<210> SEQ ID NO 13
<211> LENGTH: 35
<212> TYPE: DNA
<213> ORGANISM: Artificial Sequence
<220> FEATURE:
<223> OTHER INFORMATION: Synthetic primer

<400> SEQUENCE: 13
ccggcgcgcc cttatcatct ccacgtatca gacac 35

<210> SEQ ID NO 14
<211> LENGTH: 108
<212> TYPE: PRT
<213> ORGANISM: Aspergillus fumigatus Af293
<220> FEATURE:
<221> NAME/KEY: misc_feature
<222> LOCATION: (1)..(108)
<223> OTHER INFORMATION: AfAmy1 putative carbohydrate binding domain
(position 523 to position 630 of SEQ ID NO: 1)

<400> SEQUENCE: 14

```
Cys Ala Ala Ala Thr Ala Ile Pro Ile Leu Phe Glu Glu Leu Val Thr
1               5                   10                  15

Thr Thr Tyr Gly Glu Ser Ile Tyr Leu Thr Gly Ser Ile Ser Gln Leu
            20                  25                  30

Gly Asn Trp Asp Thr Ser Ser Ala Ile Ala Leu Ser Ala Ser Lys Tyr
        35                  40                  45

Thr Ser Ser Asn Pro Glu Trp Tyr Val Thr Val Thr Leu Pro Val Gly
    50                  55                  60

Thr Ser Phe Glu Tyr Lys Phe Val Lys Lys Gly Ser Asp Gly Ser Ile
65                  70                  75                  80

Ala Trp Glu Ser Asp Pro Asn Arg Ser Tyr Thr Val Pro Thr Gly Cys
                85                  90                  95

Ala Gly Thr Thr Val Thr Val Ser Asp Thr Trp Arg
            100                 105


<210> SEQ ID NO 15
<211> LENGTH: 20
<212> TYPE: PRT
<213> ORGANISM: Aspergillus fumigatus Af293
<220> FEATURE:
<221> NAME/KEY: misc_feature
<222> LOCATION: (1)..(20)
<223> OTHER INFORMATION: AfAmy1 putative linker (linker region; position
      503 to position 522 of SEQ ID NO: 1)

<400> SEQUENCE: 15

Ile Ser Thr Thr Ala Thr Ala Pro Ser Ala Thr Thr Ser Ala Thr Ala
1               5                   10                  15

Thr Arg Thr Ala
            20


<210> SEQ ID NO 16
<211> LENGTH: 630
<212> TYPE: PRT
<213> ORGANISM: Aspergillus fumigatus A1163
<220> FEATURE:
<221> NAME/KEY: misc_feature
<222> LOCATION: (1)..(630)
<223> OTHER INFORMATION: Putative alpha-amylase from Aspergillus
      fumigatus A1163

<400> SEQUENCE: 16

Met Lys Trp Ile Ser Gln Leu Phe Pro Leu Ser Leu Cys Ser Ser Leu
1               5                   10                  15

Leu Gly Gln Ala Ala His Ala Leu Thr Pro Ala Glu Trp Arg Ser Gln
            20                  25                  30

Ser Ile Tyr Phe Leu Leu Thr Asp Arg Phe Gly Arg Glu Asp Asn Ser
        35                  40                  45

Thr Thr Ala Ala Cys Asp Val Thr Gln Arg Leu Tyr Cys Gly Gly Ser
    50                  55                  60

Trp Gln Gly Ile Ile Asn His Leu Asp Tyr Ile Gln Gly Met Gly Phe
65                  70                  75                  80

Thr Ala Ile Trp Ile Thr Pro Val Thr Glu Gln Phe Tyr Glu Asn Thr
                85                  90                  95

Gly Asp Gly Thr Ser Tyr His Gly Tyr Trp Gln Gln Asn Ile His Glu
            100                 105                 110

Val Asn Ala Asn Tyr Gly Thr Ala Gln Asp Leu Arg Asp Leu Ala Asn
        115                 120                 125

Ala Leu His Ala Arg Gly Met Tyr Leu Met Val Asp Val Val Ala Asn
```

-continued

```
    130                 135                 140

His Met Gly Tyr Asn Gly Ala Gly Asn Ser Val Asn Tyr Gly Val Phe
145                 150                 155                 160

Thr Pro Phe Asp Ser Ala Thr Tyr Phe His Pro Tyr Cys Leu Ile Thr
                165                 170                 175

Asp Tyr Asn Asn Gln Thr Ala Val Glu Asp Cys Trp Leu Gly Asp Thr
            180                 185                 190

Thr Val Ser Leu Pro Asp Leu Asp Thr Thr Ser Thr Ala Val Arg Ser
        195                 200                 205

Ile Trp Tyr Asp Trp Val Lys Gly Leu Val Ala Asn Tyr Ser Ile Asp
    210                 215                 220

Gly Leu Arg Ile Asp Thr Val Lys His Val Glu Lys Asp Phe Trp Pro
225                 230                 235                 240

Gly Tyr Asn Asp Ala Ala Gly Val Tyr Cys Val Gly Glu Val Phe Ser
                245                 250                 255

Gly Asp Pro Gln Tyr Thr Cys Pro Tyr Gln Asn Tyr Leu Asp Gly Val
            260                 265                 270

Leu Asn Tyr Pro Ile Tyr Tyr Gln Leu Leu Tyr Ala Phe Gln Ser Thr
        275                 280                 285

Ser Gly Ser Ile Ser Asn Leu Tyr Asn Met Ile Ser Ser Val Ala Ser
    290                 295                 300

Asp Cys Ala Asp Pro Thr Leu Leu Gly Asn Phe Ile Glu Asn His Asp
305                 310                 315                 320

Asn Pro Arg Phe Ala Ser Tyr Thr Ser Asp Tyr Ser Gln Ala Lys Asn
                325                 330                 335

Val Ile Ser Phe Met Phe Phe Ser Asp Gly Ile Pro Ile Val Tyr Ala
            340                 345                 350

Gly Gln Glu Gln His Tyr Ser Gly Gly Ala Asp Pro Ala Asn Arg Glu
        355                 360                 365

Ala Val Trp Leu Ser Gly Tyr Ser Thr Ser Ala Thr Leu Tyr Ser Trp
    370                 375                 380

Ile Ala Ser Thr Asn Lys Ile Arg Lys Leu Ala Ile Ser Lys Asp Ser
385                 390                 395                 400

Ala Tyr Ile Thr Ser Lys Asn Asn Pro Phe Tyr Tyr Asp Ser Asn Thr
                405                 410                 415

Leu Ala Met Arg Lys Gly Ser Val Ala Gly Ser Gln Val Ile Thr Val
            420                 425                 430

Leu Ser Asn Lys Gly Ser Ser Gly Ser Ser Tyr Thr Leu Ser Leu Ser
        435                 440                 445

Gly Thr Gly Tyr Ser Ala Gly Ala Thr Leu Val Glu Met Tyr Thr Cys
    450                 455                 460

Thr Thr Leu Thr Val Asp Ser Ser Gly Asn Leu Ala Val Pro Met Val
465                 470                 475                 480

Ser Gly Leu Pro Arg Val Phe Val Pro Ser Ser Trp Val Ser Gly Ser
                485                 490                 495

Gly Leu Cys Gly Asp Ser Ile Ser Thr Thr Ala Thr Ala Pro Ser Ala
            500                 505                 510

Thr Thr Ser Ala Thr Ala Thr Arg Thr Ala Cys Ala Ala Ala Thr Ala
        515                 520                 525

Ile Pro Ile Leu Phe Glu Glu Leu Val Thr Thr Thr Tyr Gly Glu Ser
    530                 535                 540

Ile Tyr Leu Thr Gly Ser Ile Ser Gln Leu Gly Asn Trp Asp Thr Ser
545                 550                 555                 560
```

-continued

```
Ser Ala Ile Ala Leu Ser Ala Ser Lys Tyr Thr Ser Ser Asn Pro Glu
            565                 570                 575

Trp Tyr Val Thr Val Thr Leu Pro Val Gly Thr Ser Phe Glu Tyr Lys
            580                 585                 590

Phe Val Lys Lys Gly Ser Asp Gly Ser Ile Ala Trp Glu Ser Asp Pro
        595                 600                 605

Asn Arg Ser Tyr Thr Val Pro Thr Gly Cys Ala Gly Thr Thr Val Thr
    610                 615                 620

Val Ser Asp Thr Trp Arg
625                 630


<210> SEQ ID NO 17
<211> LENGTH: 478
<212> TYPE: PRT
<213> ORGANISM: Aspergillus niger
<220> FEATURE:
<221> NAME/KEY: misc_feature
<222> LOCATION: (1)..(478)
<223> OTHER INFORMATION: Alpha-Amylase from Aspergillus niger

<400> SEQUENCE: 17

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270
```

-continued

```
Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
    370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
        435                 440                 445

Gly Asn Val Pro Val Pro Met Ala Gly Gly Leu Pro Arg Val Leu Tyr
    450                 455                 460

Pro Thr Glu Lys Leu Ala Gly Ser Lys Ile Cys Ser Ser Ser
465                 470                 475
```